US009428439B2

(12) United States Patent
Frederickson et al.

(10) Patent No.: US 9,428,439 B2
(45) Date of Patent: *Aug. 30, 2016

(54) HYDROBENZAMIDE DERIVATIVES AS INHIBITORS OF HSP90

(71) Applicant: Astex Therapeutics Ltd., Cambridge (GB)

(72) Inventors: Martyn Frederickson, Cambridge (GB); John Francis Lyons, Cambridge (GB); Neil Thomas Thompson, Cambridge (GB); Mladen Vinkovic, Cambridge (GB); Brian John Williams, Cambridge (GB); Andrew James Woodhead, Cambridge (GB); Alison Jo-Anne Woolford, Cambridge (GB)

(73) Assignee: ASTEX THERAPEUTICS LTD., Cambridge (GB)

( * ) Notice: Subject to any disclaimer, the term of this patent is extended or adjusted under 35 U.S.C. 154(b) by 129 days.

This patent is subject to a terminal disclaimer.

(21) Appl. No.: 14/149,450

(22) Filed: Jan. 7, 2014

(65) Prior Publication Data

US 2014/0221394 A1 Aug. 7, 2014

Related U.S. Application Data

(62) Division of application No. 12/445,130, filed as application No. PCT/GB2007/003871 on Oct. 12, 2007, now Pat. No. 8,653,084.

(60) Provisional application No. 60/829,243, filed on Oct. 12, 2006.

(30) Foreign Application Priority Data

Oct. 12, 2006 (GB) .................... 0620259.2

(51) Int. Cl.
| C07D 209/44 | (2006.01) |
| C07C 67/317 | (2006.01) |
| C07C 67/313 | (2006.01) |
| C07C 59/08 | (2006.01) |
| C07C 69/92 | (2006.01) |
| C07C 235/60 | (2006.01) |

(52) U.S. Cl.
CPC ............ *C07C 67/317* (2013.01); *C07C 59/08* (2013.01); *C07C 67/313* (2013.01); *C07C 69/92* (2013.01); *C07C 235/60* (2013.01); *C07D 209/44* (2013.01)

(58) Field of Classification Search
CPC .. C07D 209/44; C07C 67/317; C07C 67/313
USPC .................. 514/254.08; 544/373; 560/53, 64
See application file for complete search history.

(56) References Cited

U.S. PATENT DOCUMENTS

| 4,582,909 | A | 4/1986 | Butler et al. |
| 4,760,064 | A | 7/1988 | Tominaga et al. |
| 5,310,951 | A | 5/1994 | Djuric et al. |
| 5,332,735 | A | 7/1994 | Rault et al. |
| 6,469,024 | B2 | 10/2002 | Li et al. |
| 7,208,630 | B2 | 4/2007 | Blagg et al. |
| 7,229,986 | B2 | 6/2007 | Ishihara et al. |
| 7,425,633 | B2 | 9/2008 | Jiaang |
| 7,577,114 | B2 | 8/2009 | Hseih |
| 7,700,625 | B2 | 4/2010 | Chessari et al. |
| 7,754,725 | B2 | 7/2010 | Chessari et al. |
| 8,101,648 | B2 | 1/2012 | Chessari |
| 8,106,057 | B2 | 1/2012 | Chessari et al. |
| 8,277,807 | B2 | 10/2012 | Gallagher et al. |
| 8,530,469 | B2 * | 9/2013 | Chessari ............. C07D 209/08 514/235.2 |
| 8,653,084 | B2 * | 2/2014 | Frederickson .......... C07C 59/08 514/254.08 |
| 2003/0158177 | A1 | 8/2003 | Ishihara et al. |
| 2003/0203898 | A1 | 10/2003 | Haning et al. |
| 2004/0039038 | A1 | 2/2004 | Bernardon et al. |
| 2004/0253228 | A1 | 12/2004 | Srivastava et al. |
| 2004/0259877 | A1 | 12/2004 | Muto et al. |
| 2005/0037922 | A1 | 2/2005 | Bickers et al. |
| 2006/0019958 | A1 | 1/2006 | Muto et al. |
| 2006/0019961 | A1 | 1/2006 | Mahaney |
| 2006/0084647 | A1 | 4/2006 | Wang et al. |
| 2006/0089495 | A1 | 4/2006 | Blagg et al. |

(Continued)

FOREIGN PATENT DOCUMENTS

| DE | 19955283 | 5/2001 |
| DE | 10 2004 049 078 | 4/2006 |

(Continued)

OTHER PUBLICATIONS

Abstract: JP 9-221476: Hidenori, et. al., Preparation and Formulations of Benzazepine Derivatives and Analog as Pharmaceuticals with Affinity for Vasopressin Receptors, STN Database Accession No. 127:248027.

(Continued)

*Primary Examiner* — James O Wilson
*Assistant Examiner* — Ebenezer O Sackey
(74) *Attorney, Agent, or Firm* — Vedder Price P.C.; Thomas J. Kowalski; Deborah L. Lu

(57) ABSTRACT

The invention provides an acid addition salt of a compound of the formula (1). Also provided by the invention are processes for preparing the compound of formula (1) and alkyl analogs thereof, novel intermediates for use in the process and methods for preparing the intermediates. The invention also provides new medical uses of compounds of the formula (1) and its ethyl analog.

11 Claims, 12 Drawing Sheets

(56) References Cited

U.S. PATENT DOCUMENTS

| | | | |
|---|---|---|---|
| 2006/0100257 A1 | 5/2006 | Muto et al. |
| 2006/0111409 A1 | 5/2006 | Muto et al. |
| 2006/0122243 A1 | 6/2006 | Muto et al. |
| 2006/0173188 A1 | 8/2006 | Seki et al. |
| 2006/0178381 A1 | 8/2006 | Jolidon et al. |
| 2006/0183902 A1 | 8/2006 | Baxter et al. |
| 2007/0042997 A1 | 2/2007 | Ital et al. |
| 2007/0184516 A1 | 8/2007 | Maraheil et al. |
| 2007/0185059 A1 | 8/2007 | Muto et al. |
| 2007/0259871 A1 | 11/2007 | Chessari et al. |
| 2007/0265268 A1 | 11/2007 | Kitamura et al. |
| 2008/0090880 A1 | 4/2008 | Eggenweiler et al. |
| 2008/0306054 A1 | 12/2008 | Chessari |
| 2009/0215742 A1 | 8/2009 | Funk et al. |
| 2009/0215771 A1 | 8/2009 | Graczyk et al. |
| 2009/0215772 A1 | 8/2009 | Chessari et al. |
| 2010/0152184 A1 | 6/2010 | Congreve et al. |
| 2010/0179145 A1 | 7/2010 | Gallagher et al. |
| 2011/0105501 A1 | 5/2011 | Gallagher et al. |
| 2015/0045362 A1* | 2/2015 | Chessari .............. C07D 209/08 514/235.2 |

FOREIGN PATENT DOCUMENTS

| | | |
|---|---|---|
| EP | 347168 | 12/1989 |
| EP | 353753 | 2/1990 |
| EP | 0474403 | 3/1992 |
| EP | 0486386 | 5/1992 |
| EP | 0500336 | 8/1992 |
| EP | 0722723 | 7/1996 |
| EP | 1283199 | 2/2003 |
| EP | 1352650 | 10/2003 |
| EP | 1510207 | 3/2005 |
| EP | 1510210 | 3/2005 |
| EP | 1512396 | 3/2005 |
| EP | 1514544 | 3/2005 |
| EP | 1642880 | 4/2006 |
| EP | 1704856 | 9/2006 |
| EP | 1852112 | 11/2007 |
| JP | 49010506 | 1/1974 |
| JP | 09194450 | 7/1997 |
| WO | WO 91/08205 | 6/1991 |
| WO | WO 92/17467 | 10/1992 |
| WO | WO 97/26884 | 7/1997 |
| WO | WO 97/35999 | 10/1997 |
| WO | WO 97/36876 | 10/1997 |
| WO | WO 97/39750 | 10/1997 |
| WO | WO 97/47270 | 12/1997 |
| WO | WO 98/40385 | 9/1998 |
| WO | WO 98/45255 | 10/1998 |
| WO | WO 98/47885 | 10/1998 |
| WO | WO 98/50036 | 11/1998 |
| WO | WO 99/21422 | 5/1999 |
| WO | WO 99/29705 | 6/1999 |
| WO | WO 00/59867 | 10/2000 |
| WO | WO 01/36351 | 5/2001 |
| WO | WO 01/60369 | 8/2001 |
| WO | WO 01/87834 | 11/2001 |
| WO | WO 01/87887 | 11/2001 |
| WO | WO 01/90053 | 11/2001 |
| WO | WO 02/12210 | 2/2002 |
| WO | WO 02/18319 | 3/2002 |
| WO | WO 03/051877 | 6/2003 |
| WO | WO 03/053366 | 7/2003 |
| WO | WO 03/055860 | 7/2003 |
| WO | WO 03/086282 | 10/2003 |
| WO | WO 03/103665 | 12/2003 |
| WO | WO 2004/005295 | 1/2004 |
| WO | WO 2004/007501 | 1/2004 |
| WO | WO 2004/035571 | 4/2004 |
| WO | WO 2004/072051 | 8/2004 |
| WO | WO 2004/074283 | 9/2004 |
| WO | WO 2004/096757 | 11/2004 |
| WO | WO 2005/000300 | 1/2005 |
| WO | WO 2005/000839 | 1/2005 |
| WO | WO 2005/007151 | 1/2005 |
| WO | WO 2005/009940 | 2/2005 |
| WO | WO 2005/012256 | 2/2005 |
| WO | WO 2005/012297 | 2/2005 |
| WO | WO 2005/012541 | 2/2005 |
| WO | WO 2005/016889 | 2/2005 |
| WO | WO 2005/023818 | 3/2005 |
| WO | WO 2005/037214 | 4/2005 |
| WO | WO 2005/047249 | 5/2005 |
| WO | WO 2005/000778 | 6/2005 |
| WO | WO 2005/063222 | 7/2005 |
| WO | WO 2006/015123 | 2/2006 |
| WO | WO 2006/023778 | 3/2006 |
| WO | WO 2006/047740 | 5/2006 |
| WO | WO 2006/051808 | 5/2006 |
| WO | WO 2006/055760 | 5/2006 |
| WO | WO 2006/070195 | 7/2006 |
| WO | WO 2006/077426 | 7/2006 |
| WO | WO 2006/082001 | 8/2006 |
| WO | WO 2006/088193 | 8/2006 |
| WO | WO 2006/109085 | 10/2006 |
| WO | WO 2006/117669 | 11/2006 |
| WO | WO 2006/125119 | 11/2006 |
| WO | WO 2007/050124 | 5/2007 |
| WO | WO 2008/044027 | 4/2008 |
| WO | WO 2008/044029 | 4/2008 |
| WO | WO 2008/044034 | 4/2008 |
| WO | WO 2008/044041 | 4/2008 |
| WO | WO 2008/044045 | 4/2008 |
| WO | WO 2008/044054 | 4/2008 |
| WO | WO 2008/053319 | 5/2008 |

OTHER PUBLICATIONS

Berge et al. "Pharmaceuticals Salts" J. Pharm Sci. 6691):1-19, Jan. 1977.

Bohonowych et al., Journal of Oncology, vol. 2010, pp. 1-17 (2010).

Brown "Chapter 5: Thermoptometry", Introduction to Thermal Analysis: Techniques and Applications, Second Edition, Netherlands, 2001.

Bryn et al., Solid State Chemistry of Drugs, 2nd edition, 1999, pp. 233-247.

Chemical Abstracts, Accession No. 81:120448 (Abstract of JP 49010506, Mar. 11, 1994).

Connor et al. "Antiviral Activity and RNA Polymerase Degradation Following HSP90 Inhibition in a Range of Negative Strand Viruses". Virology; 362, 2007:109-119.

Dymock, et al., Expert Opin. Ther. Patents (2004) vol. 14, p. 837-847.

Galam, et al. Bioog. Med. Chem. (2007) vol. 15, p. 1939-1946.

Golub et al., "Molecular Classification of Cancer: Class Discovery and Class Prediction by Gene Expression Monitoring" Science. Oct. 15, 1999;286(5439):531-7.

Gura, Science, Nov. 7, 1997, vol. 278, No. 5340, pp. 1041-1042.

Hunter et. al., "Cdc37: A Protein Kinase Chaperone?" Trends in Cell Biology, vol. 7, Apr. 1997, pp. 157-162.

International Search Report for PCT/GB2006/001382.

Ju huai-qiang et al: "Synthesis and in vitro anti-HSV-1 activity of a novel Hsp90 inhibitor BJ-B11.", Bioorganic & Medicinal Chemistry Letters Mar. 15, 2011, vol. 21, No. 6, p. 1675-1677.

Kubinyi et al., "3D QSAR In Drug Design: Ligand-Protein Interactions and Molecular Similarity", Springer (1988)vol. 2-3, 800 pages, TOC and pp. 243-244 provided.

Lala et al., "Role of Nitric Oxide in Tumor Progression: Lessons From Experimental Tumors" Cancer Metastasis Rev. Mar. 1998: 17 (1):91-106.

Madsen et al., "Glucose-6-Phosphatase Catalytic Enzyme Inhibitors: Synthesis and In Vitro Evaluation of Novel 4,5,6,7-tetrahydrothieno [3,2-c]-and—[2,3c]pyridines" Bioorg Med Chem. Sep. 2000;8(9):2277-89.

Mahaney et al., "Synthesis and Activity of a New Class of Pathway-Selective Estrogen Receptor Ligands: Hydroxybenzoyl-3,4-dihydroquinoxalin-2(1H)-ones" Bioorg Med Chem. May 15, 2006;14(10):3455-66.

Mutschler et al. Drug Action: Basic Principles and Therapeutic Aspects. CRC Press. 1995. pp. 515-580.

(56) References Cited

OTHER PUBLICATIONS

Nakagawa et al. "HSP90 Inhibitors Suppress HCV Replication in Replicon Cells and Humanized Liver Mice" Biochemical and Biophysical Research Communications 2007; 353:882-888.
Otani et al., "An Evaluation of Amide Group Planarity in 7-azabicyclo[2.2.1]Heptane Arnids. Low Amide Bond Barrier in Solution." J. Amer. Chem. Soc., 125(49), 15191-15199, 1983.
Roberts et al, JAMA, 292(17): 2130-2140 (2004).
Stephen Neidle Ed,. "Cancer Drug Design and Discovery", Elsevier/Academic Press, 2008, pp. 427-431.
UK Patent Office Search Report for GB 0507474.5.
UK Patent Office Search Report for GB 0604111.5.
U.S. Appl. No. 13/271,678, filed Oct. 12, 2011, and Preliminary Amendment therefor.
Vippagunta et al., Adv. Drug Delivery Reviews (2001) vol. 48, p. 3-26.
Waxman et al. "Host Cell Factor Requirement for Hepatitis C Virus Enzyme Maturation" PNAS. 2001; 98(24):13931-13935.
Wermuth, The Practice of Medicinal Chemistry, 2d ed. (2003) 768 pages, Chapters 9-10 provided.

\* cited by examiner

HYDROBENZAMIDE DERIVATIVES AS INHIBITORS OF HSP90

This application is a divisional of U.S. application Ser. No. 12/445,130 filed Nov. 15, 2010, now U.S. Pat. No. 8,653,084, which is a National Stage filing under 35 U.S.C. §371 of PCT Application No. PCT/GB2007/00387, filed Oct. 12, 2007, and published as WO 2008/044034 on Apr. 17, 2008, which claims priority to provisional applications GB 0620259.2, filed Oct. 12, 2006, and U.S. Ser. No. 60/829,243, filed Oct. 12, 2006.

This invention relates to novel crystalline and salt forms of compounds that inhibit or modulate the activity of the heat shock protein Hsp90 and to the use of the compounds in the treatment or prophylaxis of disease states or conditions mediated by Hsp90. Also provided are novel processes for making the compounds and novel chemical intermediates.

BACKGROUND OF THE INVENTION

In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major inducible form Hsp90α and minor constitutively expressed form Hsp90β and two other closely related chaperones which are restricted in their intracellular location (Endoplasmic reticulum GP96/GRP94; mitochondrial TRAP1). The term HSP90 as used here includes all these analogues unless stated. Hsp90 binds proteins at a late stage of folding and is distinguished from other Hsps in that most of its protein substrates are involved in signal transduction. Hsp90 has a distinct ATP binding site, including a Bergerat fold characteristic of bacterial gyrase, topoisomerases and histidine kinases. It has been shown that ATP bound at the N-terminal pocket of Hsp90 is hydrolysed. This ATPase activity results in a conformational change in Hsp90 that is required to enable conformational changes in the client protein.

A dimerization domain and a second ATP binding site, which may regulate ATPase activity, is found near the c-terminus of Hsp90. Dimerization of Hsp90 appears critical for ATP hydrolysis. Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind Hsp90. A simplified model has emerged in which ATP binding to the amino terminal pocket alters Hsp90 conformation to allow association with a multichaperone complex. First the client protein is bound to an Hsp70/Hsp40 complex. This complex then associates with Hsp90 via Hop. When ADP is replaced by ATP, the conformation of Hsp90 is altered, Hop and Hsp70 are released and a different set of co-chaperones is recruited including p50cdc37 and p23. ATP hydrolysis results in the release of these co-chaperones and the client protein from the mature complex. Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al., 1997. J Biol. Chem., 272: 23834-23850).

Despite Hsp90 being ubiquitously expressed, GA has a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec J. Med. Chem. 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

There is some evidence that Hsp90 is found primarily within "activated" multichaperone complexes in the tumour cells as opposed to "latent" complexes in normal cells. One component of the multichaperone complex is the cdc37 co-chaperone. Cdc37 binds Hsp90 at the base of the ATP binding site and could affect the off rates of inhibitors bound to Hsp90 in the "activated" state (Roe et. al., Cell 116, (2004), pp. 87-98). The client protein bound to the Hsp90-Hsp70 form of the chaperone complex is believed to be more susceptible to ubiquitination and targeting to the proteasome for degradation. E3 ubiquitin ligases have been identified with chaperone interacting motifs and one of these (CHIP) was shown to promote the ubiquitination and degradation of Hsp90 client proteins (Connell et al., 2001. Xu et al., 2002).

Hsp90 Client Proteins

The number of reported Hsp90 client proteins now exceeds 100. Since many of its client proteins are involved in cell signalling proliferation and survival, Hsp90 has received major interest as an oncology target. Two groups of client proteins, cell signalling protein kinases and transcription factors, in particular suggest Hsp90 regulation may have potential benefit as an anticancer therapy.

Hsp900 protein kinase client proteins implicated in cell proliferation and survival include the following:

c-Src

Cellular Src (c-Src) is a receptor tyrosine kinase, required for mitogenesis initiated by multiple growth factor receptors, including the receptors for epidermal growth factor receptor (EGFR), platelet-derived growth factor receptor (PDGFR), colony stimulating factor-1 (CSF-1R), and the basic fibroblast growth factor (bFGFR). C-Src is also overexpressed and activated in many of the same human carcinomas that overexpress EGFR and ErbB2. Src is also required for the maintenance of normal bone homeostasis through its regulation of osteoclast function.

p185erbB2

ErbB2 (Her2/neu) is a receptor tyrosine kinase overexpressed in a variety of malignancies including breast, ovarian, prostate, and gastric cancers. ErbB2 was originally identified as an oncogene and inhibition of Hsp90 results in the polyubiquitination and degradation of erbB2.

Polo Mitotic Kinase

Polo-like kinases (Plks) are important regulators of cell cycle progression during M-phase. Plks are involved in the assembly of the mitotic spindle apparatus and in the activation of CDKicyclin complexes. Plk1 regulates tyrosine dephosphorylation of CDKs through phosphorylation and activation of Cdc25C. CDK1 activation in turn leads to spindle formation and entry into M phase.

Akt (PKB)

Akt is involved in pathways that regulate cell growth by stimulating cell proliferation and suppressing apoptosis. Hsp90 inhibition by ansamycins results in a reduction in the Akt half-life through ubiquitination and proteasomal degradation. Binding of cdc37 to Hsp90 is also required for the down-regulation of Akt. Following ansamycin treatment cancer cells arrest in the G2/M phase of the cell cycle 24 hours after treatment and proceed to apoptosis 24-48 hours later. Normal cells also arrest 24 hours after ansamycin treatment, but do not proceed on to apoptosis.

c-Raf, B-RAF, Mek

The RAS-RAF-MEK-ERK-MAP kinase pathway mediates cellular responses to growth signals. RAS is mutated to an oncogenic form in approximately 15% of human cancers. The three RAF genes are serine/threonine kinases that are regulated by binding RAS.

EGFR

The epidermal growth factor receptor (EGFR) is implicated in cell growth, differentiation, proliferation, survival, apoptosis, and migration. Overexpression of EGFR has been found in many different cancers and activating mutations of its kinase domain appear to be pathogenic in a subset of adenocarcinoams of the lung.

Flt3

FMS-like tyrosine kinase 3 (FLT3) is a receptor tyrosine kinase involved in cell proliferation, differentiation and apoptosis. Flt3 activation also leads to the activation of phosphatidylinositol 3-kinase (PI3K) and RAS signal-transduction cascades.

c-Met c-met is a receptor tyrosine kinase which binds hepatocyte growth factor (HGF) and regulates both cell motility and cell growth. c-met is overexpressed in tumours, including thyroid, stomach, pancreatic and colon cancer. HGF is also detected around the tumours, including liver metastases. This suggests that c-met and HGF play an important role in invasion and metastasis.

Cdk1, Cdk2, Cdk4, Cdk6

Cdk1, Cdk2, Cdk4, and Cdk6 drive the cell cycle. The activity of CDKs is regulated by their binding to specific subunits such as cyclins, inhibitory and assembly factors. The substrate specificity and timing of CDK activities is dictated by their interaction with specific cyclins. Cdk4/cyclin D and Cdk6/cyclin D are active in the G1 phase, Cdk2/cyclin E and Cdk2/cyclin A in S phase, and Cdc2/cyclin A and Cdc2/cyclin B in G2/M phase.

Cyclin-dependent kinase type 4 (CDK4), plays a key role in allowing cells to traverse G1 to S-phase transition of the cell cycle and is constitutively activated in many human cancers. The CDK4 activator, cyclin D1, is overexpressed and a CDK4 inhibitor, p16, is deleted in a variety of human tumours.

Cdk1/Cdk2 inhibitors have been developed which reversibly block normal cells in either the G1/S-phase or at the G2/M border. G2/M arrest is generally less well tolerated by the cells and consequently, they undergo apoptotic cell death. Since Hsp90 also is known to affect cell survival pathways this effect may be further amplified with an Hsp90 inhibitor.

Wee-1

The Wee-1 protein kinase carries out the inhibitory phosphorylation of CDC2 on tyrosine 15 (Tyr15). This is required for activation of the G2-phase checkpoint in response to DNA damage.

Hsp90 transcription factors implicated in cell proliferation and survival include the following:

Mutant p53

P53 is a tumour suppressor protein that causes cell cycle arrest and induces apoptosis. P53 is mutated in approximately half of all cancers. Mutant p53 associates with Hsp90 and is down-regulated in cancer lines treated with Hsp90 inhibitors, while wild type p53 levels were unaffected.

Progesterone Receptor/Estrogen Receptor/Androgen Receptor

Approximately 70% of post-menopausal women who develop breast cancer have tumours that express the estrogen receptor. The first line treatment of these patients is directed at preventing signalling through this pathway and thus inhibiting tumour growth. This can be done by ovarian ablation, treatment with gonadotrophin releasing hormone agonists, aromatase inhibition or treatment with specific agonists which bind to the estrogen receptor but prevent further signalling. Ultimately patients develop resistance to these interventions often as a consequence of crosstalk between the estrogen receptor and growth factor receptors located on the cell membrane. In the unliganded state estrogen receptors are complexed with Hsp90 which facilitates hormone binding. Following binding to the mature receptor Hsp90 complex the liganded receptor can bind to hormone-response elements (HREs) within the regulatory regions of target genes involved in maintaining cell proliferation. Inhibition of Hsp90 initiates proteosomal degradation of the estrogen receptor thus preventing further growth signalling via this pathway. Prostate cancers are hormone-dependent malignancies that respond to therapeutic interventions which reduce circulating levels of testosterone or prevent testosterone binding to the androgen receptor. Although patients initially respond to these treatments most subsequently develop resistance via restoration of signalling via the androgen receptor. Prior to ligand binding the androgen receptor exists in a complex with Hsp90 and other co-chaperones including p23 and immunophilins. This interaction maintains the androgen receptor in a high-affinity ligand binding conformation. Inhibition of Hsp90 leads to proteosomal degradation of the androgen receptor and other co-chaperones which may sensitise the tumour to further hormonal therapies.

Mutated steroid hormone receptors that have arisen for example during anti-hormone therapy and which might be resistant to such therapies are likely to have a greater dependence on HSP90 for their stability and hormone binding function.

Hif-1a

Hypoxia inducible factor-1a (HIF-1a) is a transcription factor that controls the expression of genes which play a role in angiogenesis. HIF-1a is expressed in the majority of metastases and is known to associate with Hsp900. Ansamycin treatment of renal carcinoma cell lines leads to the ubiquitination and proteasomal degradation of HIF-1a.

Hsp90 inhibitors are capable of affecting a large number of targets significant to signal transduction in tumour cell proliferation. Signal transduction inhibitors which regulate the activities of a single target, may not be as efficacious due to signalling pathway redundancy and the rapid development of resistance.

By regulating multiple targets involved in cell signalling and cell proliferation HSP90 inhibitors may prove beneficial in the treatment of a wide spectrum of proliferative disorders.

ZAP70

ZAP-70, a member of the Syk-ZAP-70 protein tyrosine kinase family, is normally expressed in T cells and natural killer cells and has a critical role in the initiation of T-cell signalling. However, it is also expressed aberrantly in approximately 50% of cases of CLL, usually in those cases with unmutated B-cell receptor genes. The mutational status of immunoglobulin heavy-chain variable-region (IgVH) genes in the leukemic cells of chronic lymphocytic leukemia (CLL) is an important prognostic factor. The expression of ZAP-70 in CLL cells correlates with IgVH mutational status, disease progression, and survival. ZAP-70 positive CLL is more aggressive than ZAP-70 negative CLL indicating that ZAP-70 may be a key driver of malignancy in this disease. ZAP-70 is physically associated with HSP90 in B-CLL lymphoblasts thus the inhibition of Hsp90 may sensitise these cells to existing chemotherapy or monoclonal antibody therapy.

Heat Shock Proteins and Antitumour Drug Resistance

It has long been recognized that the native tertiary conformation of any given polypeptide is determined by its primary (amino acid) sequence. However, as explained above, it is now clear that the proper folding of many proteins in vivo requires the assistance of heat-shock proteins (Hsps) acting as molecular chaperones. While this chaperone function is important to normal cellular function under all conditions, it becomes crucial in cells which are stressed (for example by heat, hypoxia or acidosis).

Such conditions typically prevail in tumour cells, which exist in a hostile host environment. The upregulation of Hsps often seen in such cells is therefore likely to represent a mechanism by which malignant cells maintain the integrity of their proteomes under conditions which compromise protein folding. Thus, modulators or inhibitors of stress proteins in general (and Hsp90 in particular) represent a class of chemotherapeutics with the unique ability to inhibit multiple aberrant signaling pathways simultaneously. They can therefore exert antitumour effects whilst eliminating (or reducing the incidence of) resistance relative to other treatment paradigms.

Moreover, therapeutic anticancer interventions of all types necessarily increase the stresses imposed on the target tumour cells. In mitigating the deleterious effects of such stresses, Hsps are directly implicated in resisting the effects of cancer drugs and treatment regimens. Thus, modulators or inhibitors of stress protein function in general (and Hsp90 in particular) represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

HSP90 Inhibitors as Anti-Fungal, Anti-Protozoal and Anti-Parasitic Agents

Fungal infections have become a major cause for concern in recent years due to the limited number of antifungal agents available, and the increasing incidence of species that are resistant to established antifungal agents such as the azoles. In addition, the growing population of immunocompromised patients (e.g. patients such as organ transplant patients, cancer patients undergoing chemotherapy, burn patients, AIDS patients, or patients with diabetic ketoacidosis) has given rise to an increase in the incidence of opportunistic fungal infections by fungal agents such as *Candida, Cryptoccocus* and *Aspergillus* species and, on occasion, *Fusarium, Trichosporon* and *Dreschlera* species.

Consequently, there is a need for new anti-fungal agents that can be used to treat the growing numbers of patients with fungal infections and in particular infections due to fungi that have become resistant to existing antifungal drugs.

HSP90 is conserved across evolution being found in bacteria (e.g. HTPG in *E. coli*) and yeast (e.g. HSC82 and HSP82). Although clients have not been formally identified for the *E. coli* form, in yeast and all higher organisms the HSP90 family has been shown to function as a chaperone for many essential proteins as described above.

Infection by a range of pathogens is associated with an antibody response to HSP90. For example in *Candida albicans* infected patients the 47 kDa C-terminal fragment of HSP90 is an immunodominant epitope. Furthermore this antibody response is associated with good prognosis suggesting a protective effect against infection. Recombinant antibodies to an epitope in this polypeptide are also protective against infection in mouse models of invasive candidiasis. (See Mathews et al Antimicrobial Agents and Chemotherapy 2003 vol 47, 2208-2216 and references therein). Likewise surface expressed HSP90 serves as an antigen in Chagas' disease, *ascariasis*, leishmaniasis, toxoplamosis and infection due to *Schistosoma mansoni* and it has been postulated that antibodies to HSP90 convey protection against plamodium infection and Malaria.

Mycograb (NeuTec Pharma/Novartis) is a human recombinant monoclonal antibody against heat shock protein 90 that is being developed as a treatment for *candida* and has shown significant responses in early trials. Furthermore, the natural product HSP90 inhibitors Geldanamycin, Herbimycin and Radicicol were originally identified by their anti-fungal activity. Key essential proteins have been identified as HSP90 clients in several human pathogens (see Cowen and Lindquist, Science. 2005 Sep. 30; 309 (5744):2175-6.) Thus HSP90 can play an important role in the growth of pathogens such as *Candida* species, and HSP90 inhibitors can be useful as treatments for a range of infectious diseases including candidiasis.

It has also been found that Hsp900 increases the capacity of fungi to develop antifungal drug resistance (see Cowen L E, Lindquist S. "Hsp90 potentiates the rapid evolution of new traits: drug resistance in diverse fungi". Science. 2005 Sep. 30; 309 (5744):2185-9). Therefore, co-administration of an Hsp90 inhibitor with an antifungal drug may enhance the efficacy of the antifungal drug and reduce resistance by preventing the emergence of resistant phenotypes.

HSP90 Inhibitors in the Treatment of Pain, Neuropathic Conditions and Stroke

Cdk5 is a member of the Cdk family of serine/threonine kinases, most of which are key regulators of the cell cycle. Cdk5 activity is regulated through association with its neuron-specific activators, p35 and p39. Recent evidence suggests that CDK5 can phosphorylate tau protein and a number of other neuronal proteins such as NUDE-1, synapsin 1, DARPP32 and the Munc 18/Syntaxin1A complex. The evidence also suggests that aberrant Cdk5 activity induced by the conversion of p35 to p25 plays a role in the pathogenesis of neurodegenerative diseases such as Alzheimer's disease (AD), amyotrophic lateral sclerosis (ALS) and Niemann's Pick type-C disease (NPD). Abnormal hyperphosphorylation of tau after Aβ1-42 treatment destabilizes microtubules, contributing to neurite degeneration and the formation of paired helical filaments (PHFs) containing neurofibrillary tangles (NFTs), one of the principal lesions of AD. It has further been found that cdk5 is necessary for correct neuronal development The p35 protein which acts as a regulator of CDK5 activity has recently been identified as a client protein for HSP90 and therefore the activity of CDK5 can be regulated by changes in the level and activity of HSP90. Thus inhibition of HSP90 can lead to loss of p35, an inhibition of CDK5, a reduction of phosphorylated tau protein in susceptible individuals and will bring benefit to sufferers of Alzheimer's Disease.

Additionally inhibition of HSP90 using known agents has been shown to reduce the accumulation of tau protein aggregates in cellular systems in vitro. (Dickey et al Curr Alzheimer Res. 2005 April; 2(2):231-8).

Cdk5 has also been shown to have a role in mediating pain signalling. Both Cdk5 and p35 have been shown to be expressed in nociceptive neurons. In p35 knockout mice, which show substantially reduced Cdk5 activity, the response to painful thermal stimuli is delayed (Pareek, T. K., et al., Proceedings of the National Academy of Sciences., 103:791-796 (2006). Additionally administration of the cyclin-dependent kinase 5 (Cdk5) inhibitor roscovitine has been shown to attenuate the formalin-induced nociceptive responses in rats (Wang, Cheng-haung, et al., Acta Pharmacologica Sinica., 26:46-50 (2005). Activation of calpain is calcium dependent and is known to affected by activation of the NMDA receptor calcium channel (Amadoro, G; Proceedings of the National Academy of Sciences of the United States of America, 103, 2892-2897 (2006)). NMDA receptor antagonists are known to be clinically effective against neuropathic pain conditions (Christoph, T; et al., Neuropharmacology, 51, 12-17 (2006)). This efficacy may be linked to the effect of NMDA receptor related calcium influx on calpain activity and its subsequent effect on the activity of Cdk5. As such compounds modulating Cdk5 activity will be useful for the treatment or prevention of pain and thus modulation of the CDK5 regulator p35 by HSP90 inhibition could lead to inhibition of CDK5.

It is desirable to have an agent for the palliative treatment of pain, i.e. the direct relief of pain in addition to the relief of pain as the result of amelioration of the underlying disease or medical condition, which is the cause of the pain.

Various Cdk's (especially Cdk's 4, 5 & 6) have been shown to be involved with or mediate neuronal death following hypoxic or ischemic insult (Rashidan, J.; et al.; Proceedings of the National Academy of Sciences., 102: 14080-14085 (2005). Furthermore the Cdk inhibitor flavopiridol has been shown to significantly reduce neuronal death in a rat model of focal cerebral ischemia (Osuga, H.; et al.; Proceedings of the National Academy of Sciences., 97:10254-10259 (2000). Cdk5 inhibitors have been shown to have protective effects in both necrotic and apoptotic paradigms of neuronal cell death (Weishaupt, J.; et al.; Molecular and Cellular Neuroscience., 24:489-502 (2003).

Stroke is a cerebrovascular event, which occurs when the normal bloodflow to the brain is disrupted, and the brain receives too much or too little blood. Stroke is one of the leading causes of death worldwide, and is also one of the most common causes of neurologic disability.

Ischemic stroke, which is the most common type of stroke, results from insufficient cerebral circulation of blood caused by obstruction of the inflow of arterial blood. Normally, adequate cerebral blood supply is ensured by a system of arteries within the brain. However, various disorders, including inflammation and atherosclerosis, can cause a thrombus, i.e., a blood clot that forms in a blood vessel. The thrombus may interrupt arterial blood flow, causing brain ischemia and consequent neurologic symptoms. Ischemic stroke may also be caused by the lodging of an embolus (an air bubble) from the heart in an intracranial vessel, causing decreased perfusion pressure or increased blood viscosity with inadequate cerebral blood flow. An embolus may be caused by various disorders, including atrial fibrillation and atherosclerosis.

A second type of stroke, hemorrhagic stroke, involves a hemorrhage or rupture of an artery leading to the brain. Hemorrhagic stroke results in bleeding into brain tissue, including the epidural, subdural, or subarachnoid space of the brain. A hemorrhagic stroke typically results from the rupture of an arteriosclerotic vessel that has been exposed to arterial hypertension or to thrombosis.

One opportunity for intervention in stroke is the prevention or reduction of risk of stroke in patients at risk for stroke. There are many known risk factors for stroke, including vascular inflammation, atherosclerosis, arterial hypertension, diabetes, hyperlipidemia and atrial fibrillation. At risk patients have been treated with agents to control blood pressure or manage blood lipid level, and have been treated with antiplatelet agents (such as clopidrogel) and anticoagulants. A second opportunity is the treatment of acute stroke. However, current pharmacologic therapies for treating acute stroke are limited to restoring blood flow within a narrow therapeutic time window of less than three hours after stroke. There remains a need for agents which are effective within a longer therapeutic time window. Another opportunity is recovery or restoration after the acute stroke period, i.e. the reduction or prevention of secondary cell damage in the penumbra. There remains a need for agents which are effective in reducing or preventing secondary cell damage after stroke.

It would be desirable to obtain a single pharmaceutical agent which can be used in more than one of the above-mentioned opportunities for treating stroke. Such an agent may be administered to patients at risk for stroke, and also may be administered to patients suffering from acute stroke, or patients undergoing treatment for recovery or restoration after the acute stroke period. Such an agent may also target more than one distinct mechanism in the biochemical cascade of stroke.

HSP90 Inhibitors and the Treatment of Hepatitis C and Other Viral Diseases

Infection of a host cell with viral RNA/DNA results in a substantial redirection of cellular protein synthesis towards key viral proteins encoded by the viral nucleic acid. The increased protein synthetic burden places a stress on the cell as a consequence of increased demand for energy and synthetic precursors. Upregulation of heat shock proteins is frequently a consequence of viral infection at least in part due to this stress. One function of the HSP induction may be to assist in the stabilization and folding of the high levels of 'foreign' protein generated in preparation for virus replication. In particular recent work has suggested that HSP90 is required for stable production of functional NS2/3 protease in Hepatitis C(HCV) replicon infected cells. HSP 90 inhibitors have also been demonstrated to block viral replication in in vitro systems. (Nagkagawa, S, Umehara T, Matsuda C, et al Biochem. Biophys. Res Commun. 353 (2007) 882-888; Waxman L, Witney, M et al PNAS 98 (2001) 13931-13935).

Our earlier application PCT/GB2006/001382, the entire contents of which are incorporated herein by reference, discloses isoindoline amides of 2,4-dihydroxybenzoic acids as Hsp90 inhibitors. One of the compounds specifically disclosed and exemplified in PCT/GB2006/001382, is the compound (2,4-dihydroxy-5-isopropyl-phenyl)-[5-(4-methyl-piperazin-1-ylmethyl)-1,3-dihydro-isoindol-2-yl]-methanone which has the structure shown below. This compound may be referred to for convenience in this application as Compound 1 or the compound of formula (1).

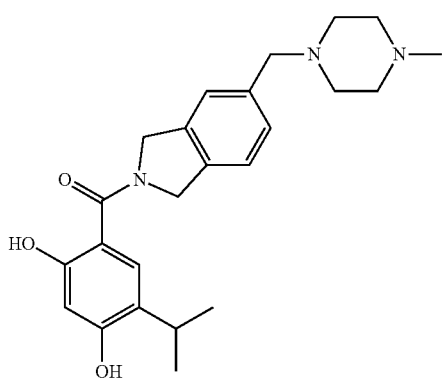

(1)

SUMMARY OF THE INVENTION

The invention provides acid salts (in particular the L-lactate salt), crystalline forms and a novel analogue of the compound of the formula (1), that have Hsp90 inhibiting or modulating activity and which will be useful in preventing or treating disease states or conditions mediated by Hsp900. The invention also provides novel processes for making the compound of formula (1) and its acid addition salts (particularly the L-lactate salt) and analogues thereof, and novel chemical intermediates. Also included within the scope of the invention are the therapeutic uses of the compounds.

GENERAL PREFERENCES AND DEFINITIONS

Figure 1:
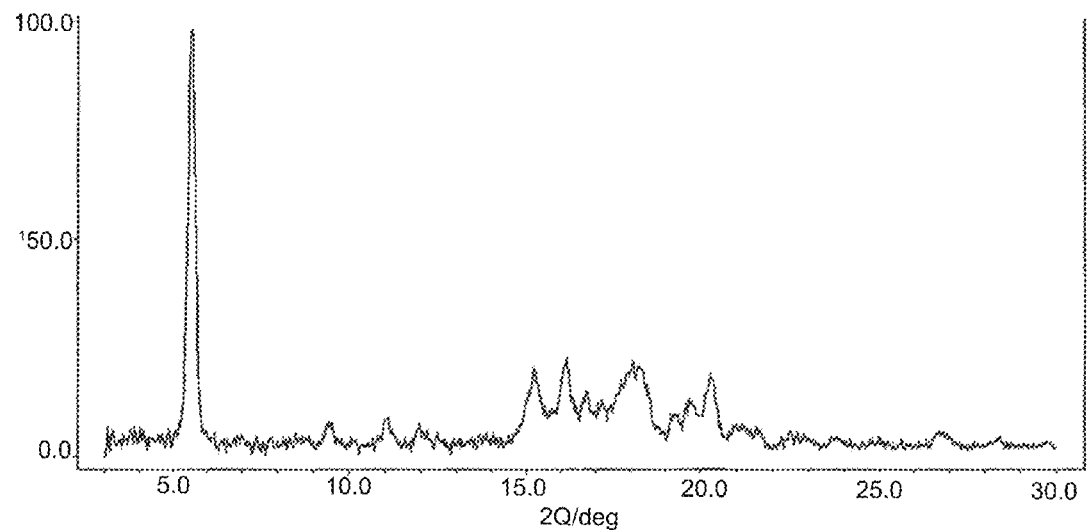
FIG. 1 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle peak (2θ/°) at 5.52.

In this specification, the terms "compounds of the invention" or "compound of the invention", unless the context indicates otherwise, refer collectively to (a) the novel compound of formula (10) and its salts, solvates, N-oxides and tautomers, (b) the acid addition salts of compound (1) (particularly the L-lactate salt), and (c) the crystalline forms of the compound of formula (1) and its acid addition salts (particularly the L-lactate).

As used herein, the term "treatment" and the related terms "treat" and "treating" refer to both prophylactic or preventative treatment as well as curative or palliative treatment of pain. Thus, the term encompasses situations where pain is already being experienced by a subject or patient, as well as situations where pain is not currently being experienced but is expected to arise. The term "treatment", "treat", "treating" and related terms also cover both complete and partial pain reduction or prevention. Thus, for example, the compounds of the invention may prevent existing pain from worsening, or they reduce or even eliminate pain. When used in a prophylactic sense, the compounds may prevent any pain from developing or they may lessen the extent of pain that may develop.

As used herein, the term "modulation", as applied to the activity of the heat shock protein Hsp90, is intended to define a change in the level of biological activity of the heat shock protein. Thus, modulation encompasses physiological changes which effect an increase or decrease in the relevant heat shock protein activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of heat shock protein activity. Thus, modulation may imply elevated/suppressed expression or over- or under-expression of the heat shock protein, including gene amplification (i.e. multiple gene copies) and/or increased or decreased expression by a transcriptional effect, as well as hyper- (or hypo-)activity and (de)activation of the heat shock protein (including (de)activation) by mutation(s). The terms "modulated", "modulating" and "modulate" are to be interpreted accordingly.

As used herein, the term "mediated", as used e.g. in conjunction with the heat shock protein as described herein (and applied for example to various physiological processes, diseases, states, conditions, therapies, treatments or interventions) is intended to operate limitatively so that the various processes, diseases, states, conditions, treatments and interventions to which the term is applied are those in which heat shock protein Hsp90 plays a biological role. In cases where the term is applied to a disease, state or condition, the biological role played by heat shock protein Hsp90 may be direct or indirect and may be necessary and/or sufficient for the manifestation of the symptoms of the disease, state or condition (or its aetiology or progression). Thus, heat shock protein Hsp90 activity (and in particular aberrant levels of heat shock protein Hsp90 activity, e.g. Hsp90 over-expression) need not necessarily be the proximal cause of the disease, state or condition: rather, it is contemplated that the heat shock protein Hsp90 mediated diseases, states or conditions include those having multifactorial aetiologies and complex progressions in which Hsp90 is only partially involved. In cases where the term is applied to treatment, prophylaxis or intervention (e.g. in the "Hsp90-mediated treatments" and "Hsp90-mediated prophylaxis" of the invention), the role played by Hsp90 may be direct or indirect and may be necessary and/or sufficient for the operation of the treatment, prophylaxis or outcome of the intervention. Thus, a disease state or condition mediated by Hsp90 includes the development of resistance to any particular cancer drug or treatment (including in particular resistance to one or more of the signalling inhibitors described herein).

As used herein, the term "modulation", as applied to the activity of cyclin dependent kinase 5 (CDK5), is intended to define a change in the level of biological activity of the kinase(s). Thus, modulation encompasses physiological changes which effect an increase or decrease in the relevant kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of cyclin dependent kinase 5 (CDK5), or at the level of enzyme (e.g. cyclin dependent kinase 5 (CDK5) activity (for example by allosteric mechanisms, competitive inhibition, active-site inactivation, perturbation of feedback inhibitory pathways etc.). Thus, modulation may imply elevated/suppressed expression or over- or under-expression of the cyclin dependent kinase 5 (CDK5) including gene amplification (i.e. multiple gene copies) and/or increased or decreased expression by a transcriptional effect, as well as hyper- (or hypo-) activity and (de)activation of the cyclin dependent kinase 5 (CDK5) including (de)activation) by mutation(s). The terms "modulated", "modulating" and "modulate" are to be interpreted accordingly.

As used herein, the term "mediated", as used e.g. in conjunction with the cyclin dependent kinase 5 (CDK5) as described herein (and applied for example to various physiological processes, diseases, states, conditions, therapies, treatments or interventions) is intended to operate limitatively so that the various processes, diseases, states, conditions, treatments and interventions to which the term is applied are those in which cyclin dependent kinase 5 (CDK5) plays a biological role. In cases where the term is applied to a disease, state or condition, the biological role played by cyclin dependent kinase 5 (CDK5) may be direct or indirect and may be necessary and/or sufficient for the manifestation of the symptoms of the disease, state or condition (or its aetiology or progression). Thus, cyclin dependent kinase 5 (CDK5) activity (and in particular aberrant levels of cyclin dependent kinase 5 (CDK5) activity, e.g. cyclin dependent kinase 5 (CDK5) over-expression) need not necessarily be the proximal cause of the disease, state or condition: rather, it is contemplated that the CDK5-mediated diseases, states or conditions include those having multifactorial antiologies and complex progressions in which CDK5. In cases where the term is applied to treatment, prophylaxis or intervention (e.g. in the "CDK5-mediated treatments" of the invention), the role played by CDK5 may be direct or indirect and may be necessary and/or sufficient for the operation of the treatment, prophylaxis or outcome of the intervention.

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
- compositions (e.g. unitary formulations) comprising the two or more compounds/agents in admixture (for example within the same unit dose);
- compositions comprising material in which the two or more compounds/agents are chemically/physicochemically linked (for example by crosslinking, molecular agglomeration or binding to a common vehicle moiety);
- compositions comprising material in which the two or more compounds/agents are chemically/physicochemically co-packaged (for example, disposed on or within lipid vesicles, particles (e.g. micro- or nanoparticles) or emulsion droplets);
- pharmaceutical kits, pharmaceutical packs or patient packs in which the two or more compounds/agents are co-packaged or co-presented (e.g. as part of an array of unit doses);

Examples of non-physically associated combined compounds/agents include:
- material (e.g. a non-unitary formulation) comprising at least one of the two or more compounds/agents together with instructions for the extemporaneous association of the at least one compound to form a physical association of the two or more compounds/agents;
- material (e.g. a non-unitary formulation) comprising at least one of the two or more compounds/agents together with instructions for combination therapy with the two or more compounds/agents;
- material comprising at least one of the two or more compounds/agents together with instructions for administration to a patient population in which the other(s) of the two or more compounds/agents have been (or are being) administered;
- material comprising at least one of the two or more compounds/agents in an amount or in a form which is specifically adapted for use in combination with the other(s) of the two or more compounds/agents.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

ACID ADDITION SALTS

In a first aspect, the invention provides an acid addition salt of a compound of the formula (1)

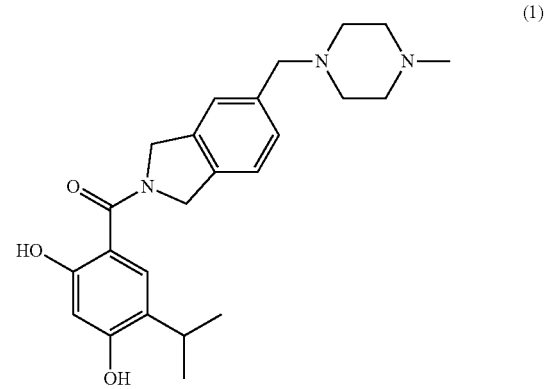 [SMILES: CC(C)c1cc(C(=O)N2Cc3ccc(CN4CCN(C)CC4)cc3C2)c(O)cc1O]

(1)

which has the chemical name (2,4-dihydroxy-5-isopropylphenyl)-[5-(4-methyl-piperazin-1-ylmethyl)-1,3-dihydro-isoindol-2-yl]-methanone.

The terms "salt" and "acid addition salt" may be used interchangeably in this application as may the terms "salts" and "acid addition salts". The terms "salt" and "salts" as used herein refer to the acid addition salts unless the context indicates otherwise.

References to the compound (2,4-dihydroxy-5-isopropylphenyl)-[5-(4-methyl-piperazin-1-ylmethyl)-1,3-dihydro-isoindol-2-yl]-methanone and its acid addition salts include within their scope all solvates, tautomers and isotopes thereof and, where the context admits, N-oxides and other ionic forms.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), aspartic (e.g. L-aspartic), benzenesulphonic, benzoic, 4-acetamidobenzoic, butanoic, camphoric (e.g. (+) camphoric), camphor-sulphonic, (+)-(1S)-camphor-10-sulphonic, capric, caproic, caprylic, carbonic, cinnamic, citric, cyclamic, dodecanoic, dodecylsulphuric, ethane-1,2- disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, isobutyric, lactic (e.g. (+)-L-lactic [which may be referred to elsewhere herein simply as L-lactic acid] and (±)-DL-lactic), laurylsulphonic, lactobionic, maleic, malic, (−)-L-malic, malonic, (±)-DL-mandelic, methanesulphonic, mucic, naphthalenesulphonic (e.g. naphthalene-2-sulphonic and naphthalene-1,5-disulphonic), 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, toluenesulphonic (e.g. p-toluenesulphonic), undecylenic, valeric acids and xinafoic acids.

Particular acid addition salts are the salts formed with hydrochloric acid, lactic acid (e.g. L-lactic acid) or sulphuric acid.

A preferred salt is the salt formed with lactic acid, i.e. the lactate salt and in particular the L-lactate salt.

The acid addition salts are typically pharmaceutically acceptable salts, and examples of pharmaceutically acceptable salts are discussed in Berge et al., 1977, "Pharmaceutically Acceptable Salts," J. Pharm. Sci., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In the solid state, the salts of the invention can be crystalline or amorphous or a mixture thereof.

In one embodiment, the salts are amorphous.

In an amorphous solid, the three dimensional structure that normally exists in a crystalline form does not exist and the positions of the molecules relative to one another in the amorphous form are essentially random, see for example Hancock et al. J. Pharm. Sci. (1997), 86, 1).

In another embodiment, the salts are substantially crystalline.

The salts of the present invention can be synthesized from the parent compound by conventional chemical methods such as methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002. Generally, such salts can be prepared by reacting the free base form of the compound of formula (1) with the appropriate acid in water or in an organic solvent, or in a mixture of the two.

In another aspect, the invention provides a method of preparing an acid addition salt of (2,4-dihydroxy-5-isopropyl-phenyl)-[5-(4-methyl-piperazin-1-ylmethyl)-1,3-dihydro-isoindol-2-yl]-methanone, which method comprises forming a solution of (2,4-dihydroxy-5-isopropyl-phenyl)-[5-(4-methyl-piperazin-1-ylmethyl)-1,3-dihydro-isoindol-2-yl]-methanone free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, (2,4-dihydroxy-5-isopropyl-phenyl)-[5-(4-methyl-piperazin-1-ylmethyl)-1,3-dihydro-isoindol-2-yl]-methanone is dissolved in a solvent comprising a volatile acid and optionally a co-solvent, thereby to form a solution of the acid addition salt with the volatile acid, and the resulting solution is then concentrated or evaporated to isolate the salt. An example of an acid addition salt that can be made in this way is the acetate salt.

The salt is typically precipitated from the organic solvent as it is formed and hence can be isolated by separation of the solid from the solution, e.g. by filtration.

One salt form of the invention can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid by one of the methods described above or elsewhere herein.

Salts such as acid addition salts have a number of advantages over the corresponding free base. For example, the salts will enjoy one or more of the following advantages over the free base in that they:
will be more soluble and hence will be better for i.v. administration (e.g. by infusion)
will have better stability (e.g. improved shelf life);
will have better thermal stability;
will be less basic and therefore better for i.v. administration;
will have advantages for production;
will have improved solubility in aqueous solution;
will have better physicochemical properties;
may have improved anti-cancer activity; and
may have an improved therapeutic index.

Particular advantages of the L-lactate salt of the compound of formula (1) are that it:
is not hydrated and therefore is easier to formulate;
has fewer polymorphic forms than the free base and other salt forms tested (i.e. the salts formed with hydrochloric acid and sulphuric acid);
is non-hygroscopic; and
has a better rate of solubility than the free base and other salts tested.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition' for example for a period of six months or more, more usually twelve months or more, for example eighteen months or more. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The terms "non-hygroscopic" and "non-hygroscopicity" and related terms as used herein refer to substances that absorb less than 5% by weight (relative to their own weight) of water when exposed to conditions of high relative humidity, for example 90% relative humidity, and/or do not undergo changes in crystalline form in conditions of high humidity and/or do not absorb water into the body of the crystal (internal water) in conditions of high relative humidity.

CRYSTALLINE FORMS

In another aspect, the invention provides a compound of the formula (1)

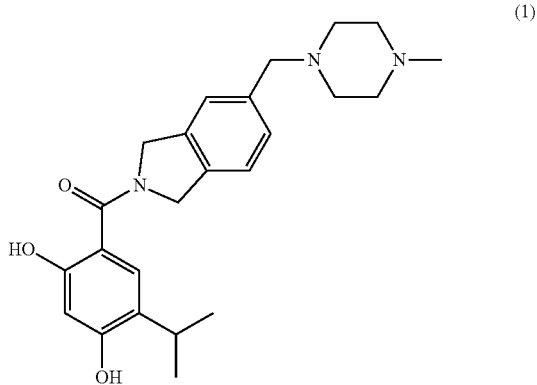

or an acid addition salt thereof in substantially crystalline form.

By "substantially crystalline" is meant that the compound of formula (1) or its acid addition salt are from 50% to 100% crystalline, and more particularly the compound of formula (1) or its salts may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

More preferably the compound of formula (1) or its salts are those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

The crystalline forms of the invention, in the solid state, can be solvated (e.g. hydrated) or non-solvated (e.g. anhydrous).

In one embodiment, the crystalline forms are non-solvated (e.g. anhydrous).

The term "anhydrous" as used herein does not exclude the possibility of the presence of some water on or in the salt (e.g. a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the crystalline forms are solvated. Where the crystalline forms are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

The crystalline forms described herein, individual crystals thereof and their crystal structures form further aspects of the invention.

The crystalline forms and their crystal structures can be characterised using a number of techniques including single crystal X-ray crystallography, X-ray powder diffraction (XRPD), differential scanning calorimetry (DSC) and infra-red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods, such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

Alternatively, the crystalline structure of a compound can be analysed by the solid state technique of X-ray Powder Diffraction (XRPD). XRPD can be carried out according to conventional methods such as those described herein and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle ($2\theta$) and interplanar spacing (d) parameters of an X-ray diffraction spectrum. These are related by Bragg's equation, $n\lambda = 2d \sin \theta$, (where n=1; $\lambda$=wavelength of the cathode used; d=interplanar spacing; and $\theta$=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of $2\theta \pm 0.2°$. The peaks mean main peaks and include peaks not larger than medium at diffraction angles other than those stated above.

The compound of formula (1) and its acid addition salts exist in a number of different crystalline forms and these are described in more detail below and are characterised in the Examples.

Crystalline Forms of the free base of (2,4-dihydroxy-5-isopropyl-phenyl)-[5-(4-methyl-piperazin-1-ylmethyl)-1,3-dihydro-isoindol-2-yl]-methanone The free base of the compound of formula (1) has been found to exist in at least six different crystalline forms of which three (the forms designated herein as FB1, FB2 and FB5) are unstable in air, and three (the forms designated herein as FB3, FB4 and FB6) are stable in air. The characteristics of the crystalline forms of the free base are described in Example 6A below.

Form FB1

In one embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle peak (2θ/°) at 5.52.

Preferably, the XRPD pattern also exhibits peaks at the diffraction angles (2θ/°) of 15.21, 16.11, 16.72, 18.21 and 20.29.

More preferably, the XRPD pattern also exhibits peaks at the diffraction angles (2θ/°) of 9.44, 11.05, 11.99, 17.09, 19.23, 19.73, 21.09 and 26.72.

Most preferably, the XRPD pattern is substantially as shown in FIG. 1 herein.

In another aspect, the invention provides a method for preparing crystalline form FB1, which method comprises dissolving (2,4-dihydroxy-5-isopropyl-phenyl)-[5-(4-methyl-piperazin-1-ylmethyl)-1,3-dihydro-isoindol-2-yl]-methanone in n-butanol to form a saturated solution and then adding di(isopropyl)ether to precipitate the crystalline form FB1.

Crystal form FB1 is unstable in air and converts to form FB3 (See below) on being left.

Accordingly, the invention also provides a method for the preparation of crystalline form FB3 as defined herein, which method comprises exposing form FB1 to air for a period sufficient to allow transformation to FB3 to take place.

Form FB2

In another embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle peak (2θ/°) at 5.35.

Preferably, the XRPD pattern also exhibits diffraction angle (2θ/°) peaks at 14.68, 17.00, 18.61, 19.86 and 20.15.

More preferably, the XRPD pattern further exhibits diffraction angle (2θ/°) peaks at 6.73, 10.40, 10.67, 18.26, 18.87, 19.24, 21.13, 21.44 and 26.86.

Figure 2:
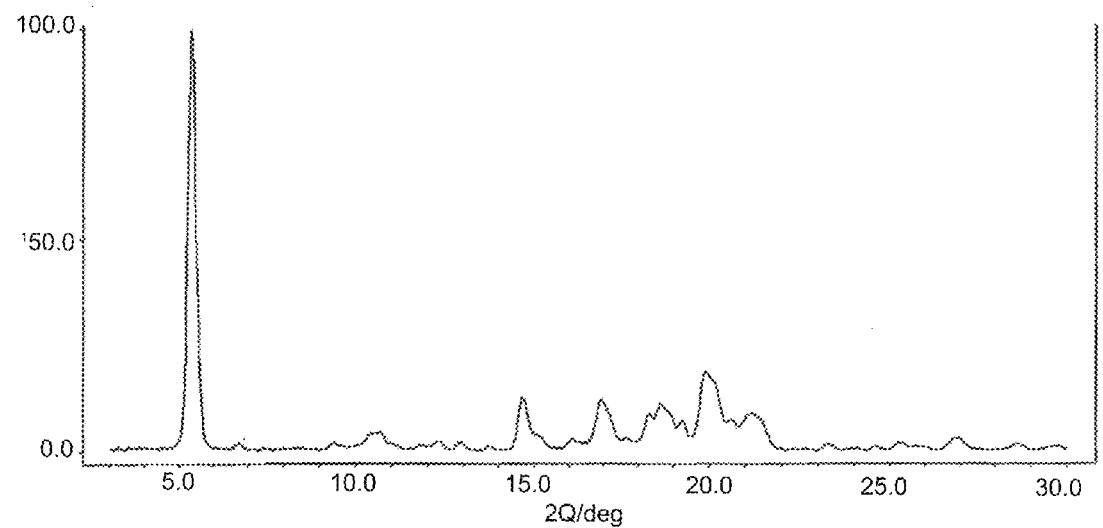
FIG. 2 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle peak (2θ/°) at 5.35.

Most preferably, the XRPD pattern is substantially as shown in FIG. 2 herein.

In another aspect, the invention provides a method for preparing crystalline form FB2, which method comprises dissolving (2,4-dihydroxy-5-isopropyl-phenyl)-[5-(4-methyl-1-piperazin-1-ylmethyl)-1,3-dihydro-isoindol-2-yl]-methanone in THF to form a saturated solution and then adding isopropyl acetate to precipitate the crystalline form FB2.

Crystal form FB2 is also unstable in air and converts to form FB3 (see below) on being left.

Accordingly, the invention also provides a method for the preparation of crystalline form FB3 as defined herein, which method comprises exposing form FB2 to air for a period sufficient to allow transformation to FB3 to take place.

Form FB3

In another embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 6.05.

Preferably, the XRPD pattern also exhibits diffraction angle (2θ/°) peaks at 12.15, 13.60, 15.77, 17.82, 18.89, 19.64, 20.20 and 20.93.

More preferably, the XRPD pattern further exhibits diffraction angle (2θ/°) peaks at 7.87, 9.15, 10.22, 16.62, 17.16, 22.19, 23.33 and 24.53.

Figure 3:
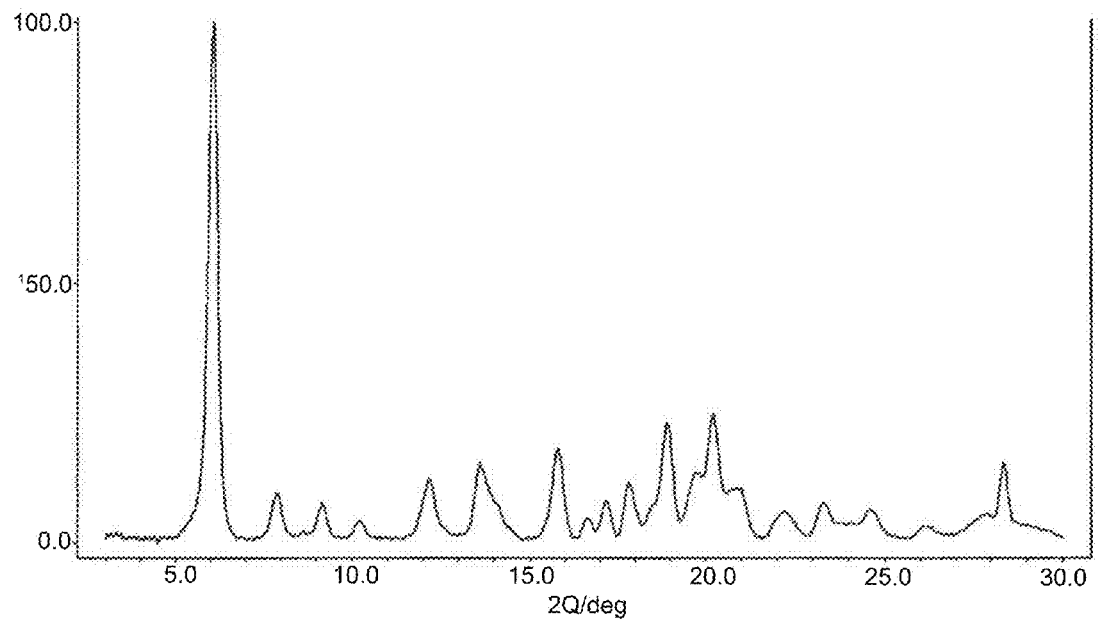
FIG. 3 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 6.05.

Most preferably, the XRPD pattern is substantially as shown in FIG. 3 herein.

Form FB3 is stable in air at 40° C. and in 75% relative humidity for at least one month and is therefore suitable for use in solid pharmaceutical compositions. Accordingly, in another aspect, the invention provides a solid pharmaceutical composition comprising 2,4-dihydroxy-5-isopropyl-phenyl)-[5-(4-methyl-piperazin-1-ylmethyl)-1,3-dihydro-isoindol-2-yl]-methanone free base in crystalline form FB3 as defined herein.

Form FB4

In another embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 6.29.

Preferably, the XRPD pattern also exhibits diffraction angle (2θ/°) peaks at 8.91, 9.96, 14.11, 16.11, 17.11, 18.48, 19.91, 21.57, 22.46, 23.59 and 24.88.

More preferably, the XRPD pattern further exhibits diffraction angle (2θ/°) peaks at 12.62, 17.40, 17.88, 19.33, 20.35 and 27.25.

Figure 4:
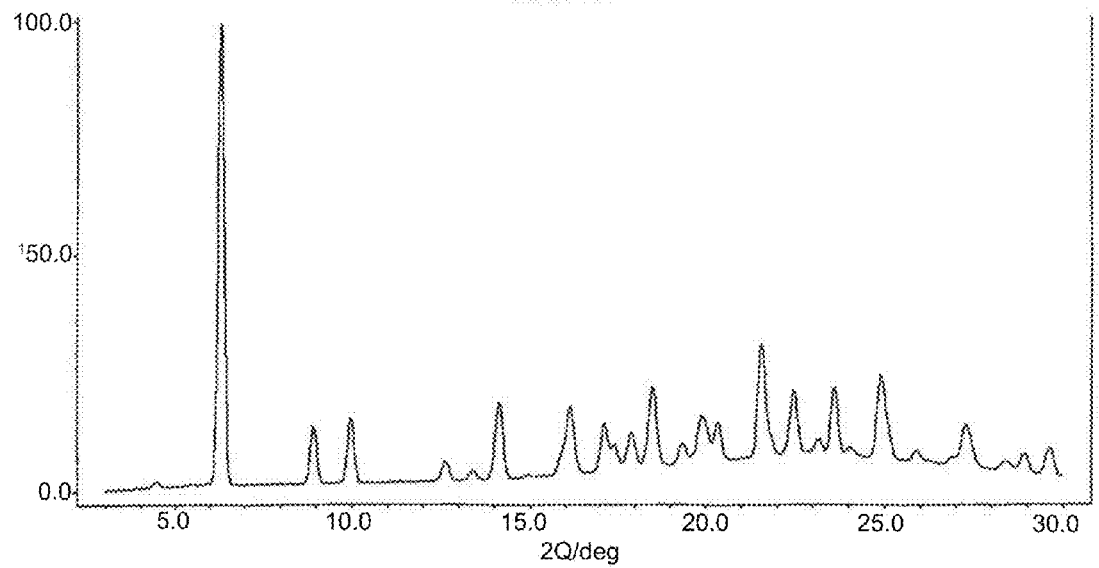
FIG. 4 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 6.29.

Most preferably, the XRPD pattern is substantially as shown in FIG. 4 herein.

From X-ray crystallography studies, it has been found that form FB4 has a crystal structure that belongs belong to the tetragonal space group P42/n and has crystal lattice parameters at 293 K a=b=28.2, c=6.0 Å, α=β=γ=90. The crystal packing diagram is shown in FIG. 5.

Figure 5:
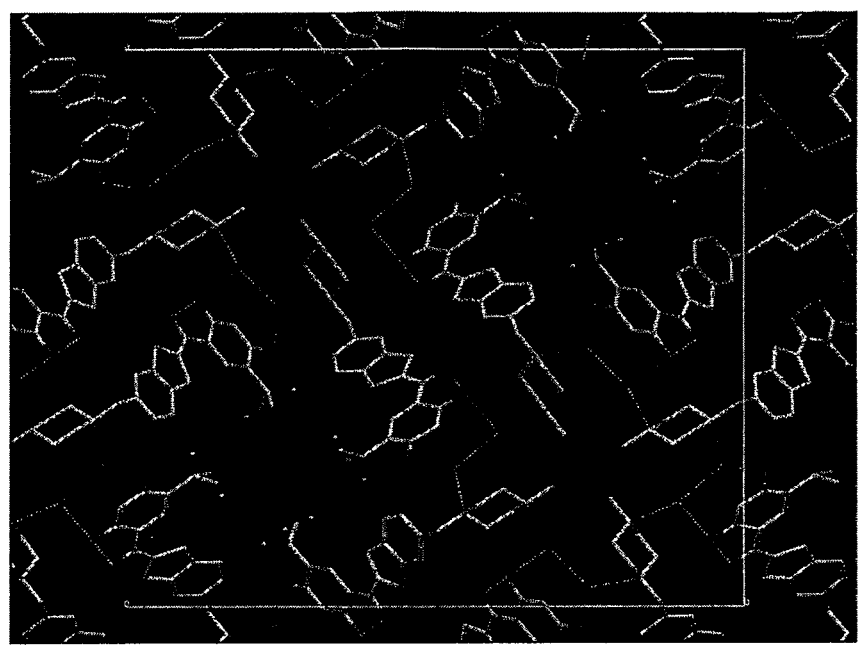
FIG. 5 depicts a crystal structure that belongs to the tetragonal space group P42/n and has crystal lattice parameters at 293 K a=b=28.2, c=6.0 Å, α=β=γ=90°.

Accordingly, in another embodiment, the invention provides (2,4-dihydroxy-5-isopropyl-phenyl)-[5-(4-methyl-piperazin-1-ylmethyl)-1,3-dihydro-isoindol-2-yl]-methanone free base which is crystalline and:

(a) has a crystal structure as set out in FIG. 5; and/or (b) has a crystal structure as defined by the coordinates in Table 5 herein; and/or (c) has crystal lattice parameters at 293 K a=b=28.2, c=6.0 Å, α=β=γ=90°; and/or (d) has a crystal structure that belongs belong to a tetragonal space group such as P42/n.

Crystalline form FB4 is a stable dihydrate and may be used for the preparation of solid pharmaceutical compositions. Accordingly, in another aspect, the invention provides a solid pharmaceutical composition comprising 2,4-dihydroxy-5-isopropyl-phenyl)-[5-(4-methyl-piperazin-1-ylmethyl)-1,3-dihydro-isoindol-2-yl]-methanone free base in crystalline form FB4 as defined herein.

In another aspect, the invention provides a method for preparing crystalline form FB4, which method comprises dissolving (2,4-dihydroxy-5-isopropyl-phenyl)-[5-(4-methyl-piperazin-1-ylmethyl)-1,3-dihydro-isoindol-2-yl]-methanone in ethanol to form a saturated solution and then adding di(isopropyl)ether to precipitate the crystalline form FB4.

Form FB5

In another embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 7.12.

Preferably, the XRPD pattern also exhibits diffraction angle (2θ/°) peaks at 9.71, 10.14, 13.73, 16.58, 18.71, 19.46, 20.15 and 22.35.

More preferably, the XRPD pattern further exhibits diffraction angle (2θ/°) peaks at 11.50, 14.60, 15.34, 16.94, 21.97, 23.43 and 26.36.

Figure 6:
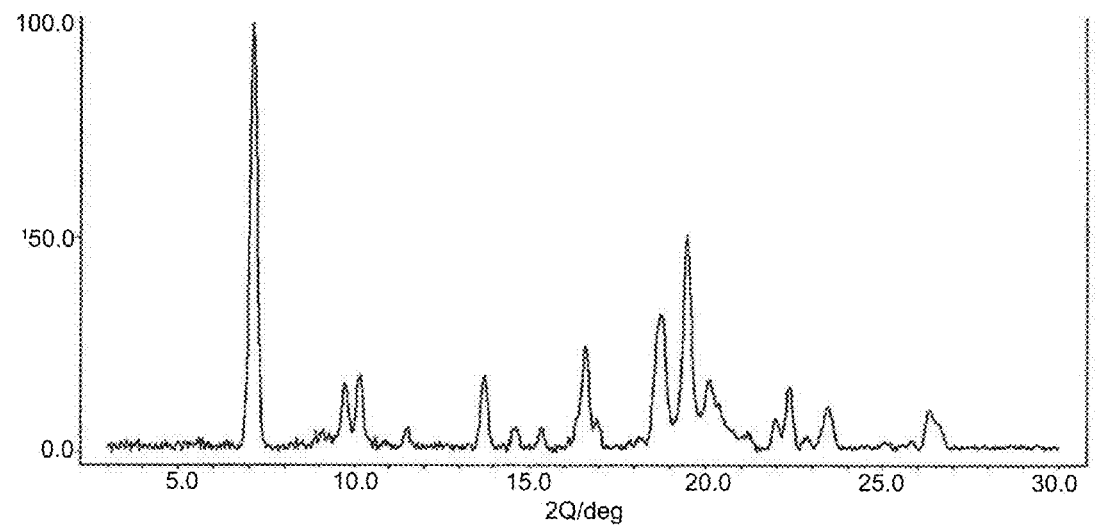
FIG. 6 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 7.12.

Most preferably, the XRPD pattern is substantially as shown in FIG. 6 herein.

In another aspect, the invention provides a method for preparing crystalline form FB5, which method comprises dissolving (2,4-dihydroxy-5-isopropyl-phenyl)-[5-(4-methyl-piperazin-1-ylmethyl)-1,3-dihydro-isoindol-2-yl]-methanone in isopropanol to form a saturated solution and then adding isopropyl acetate to precipitate the crystalline form FB5.

Form FB6

In another embodiment, the invention provides (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 18.66.

Preferably, the XRPD pattern also exhibits diffraction angle (2θ/°) peaks at 9.09, 9.68, 16.08, 16.46, 16.94, 18.13, 20.05 and 22.48.

More preferably, the XRPD pattern further exhibits diffraction angle (2θ/°) peaks at 4.60 and 26.53.

Figure 7:
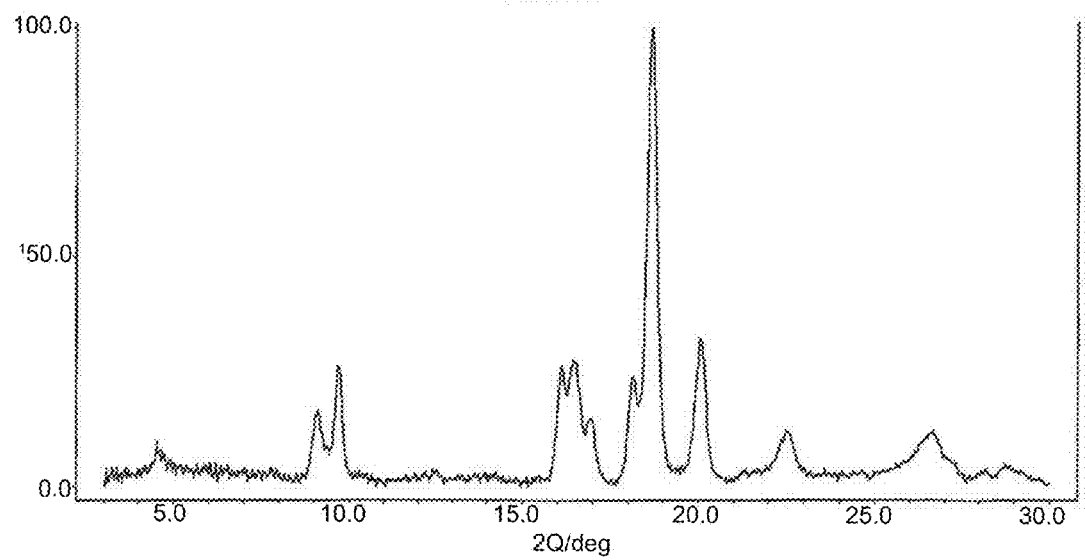
FIG. 7 depicts (2,4-dihydroxy-5-isopropyl-phenyl)-[5-(4-methyl-piperazin-1-ylmethyl)-1,3-dihydro-isoindol-2-yl]-methanone in a crystalline form characterised by an XRPD pattern having a diffraction angle (2θ/°) peak at 18.66.

Most preferably, the XRPD pattern is substantially as shown in FIG. 7 herein.

Crystalline Forms of the Salts Formed Between (2,4-dihydroxy-5-Isopropyl-phenyl)-[5-(4-methyl-piperazin-1-ylmethyl)-1,3-dihydro-isoindol-2-yl]-methanone and hydrochloric acid The hydrochloric acid salts of the compound of formula (1) have been found to exist in at least five different crystalline forms of which one (the form designated herein as FH3) is stable in air, and four (the forms designated herein as FH1, FH2, FH4 and FH5) are unstable in air.

Form FH1

In another embodiment, the invention provides (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 7.34.

Preferably, the XRPD pattern also exhibits diffraction angle (2θ/°) peaks at 5.59, 7.99, 10.33, 14.32, 15.29, 18.59 and 25.32.

More preferably, the XRPD pattern further exhibits diffraction angle (2θ/°) peaks at 11.70, 13.95, 14.72, 16.37, 16.82, 19.99, 20.40, 20.82, 21.26, 22.57, 23.01, 24.60, 25.82, 27.10, 28.27 and 28.78.

Figure 8:
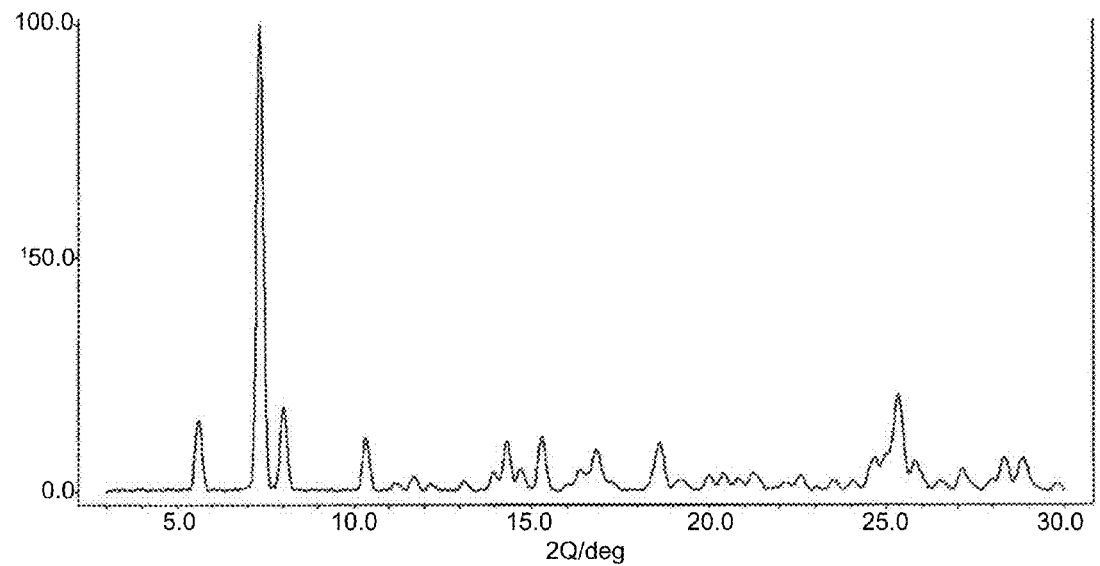
FIG. 8 depicts (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 7.34.

Most preferably, the XRPD pattern is substantially as shown in FIG. 8 herein.

In another aspect, the invention provides a method for preparing crystalline form FH1, which method comprises adding ethyl acetate/HCl and methanol to the free base of 2,4-dihydroxy-5-isopropyl-phenyl)-[5-(4-methyl-piperazin-1-ylmethyl)-1,3-dihydro-isoindol-2-yl]-methanone to give a solution and then removing the solvents to leave the di-hydrochloride salt.

Form FH2

In another embodiment, the invention provides (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 3.40.

Preferably, the XRPD pattern also exhibits diffraction angle (2θ/°) peaks at 6.81, 9.03, 11.84, 15.70, 16.10, 18.13, 20.84, 23.19, 23.94, 24.78 and 25.65.

More preferably, the XRPD pattern further exhibits diffraction angle (2θ/°) peaks at 6.04, 13.01, 13.69, 16.59, 17.17, 21.39, 21.87, 24.78, 25.97, 26.94, 27.59, 28.06 and 29.53.

Figure 9:
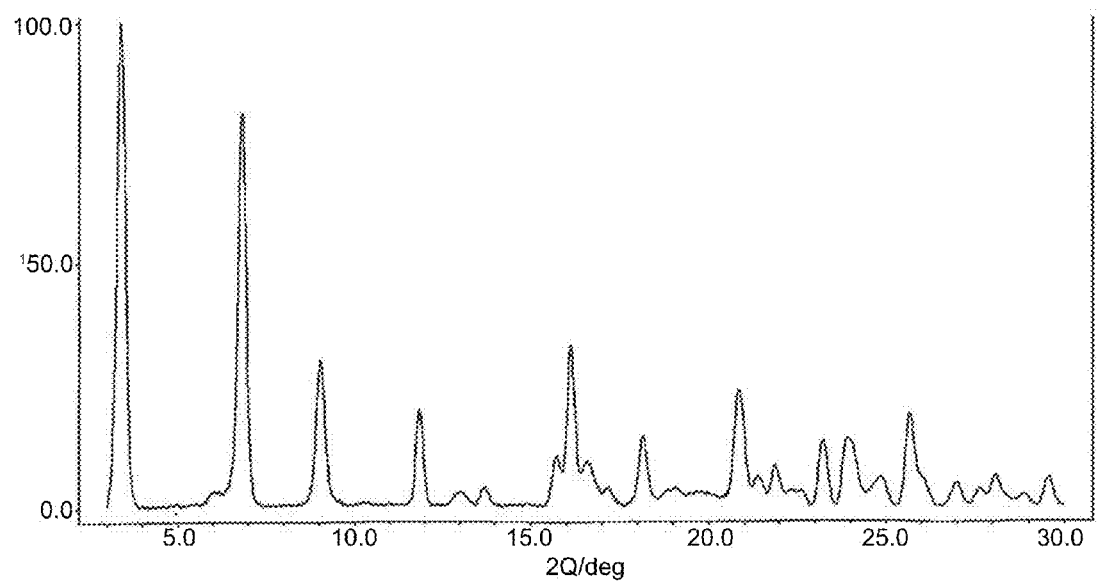
FIG. 9 depicts (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 3.40.

Most preferably, the XRPD pattern is substantially as shown in FIG. 9 herein.

Form FH2 can be prepared by precipitation from a saturated DMF solution form FH1 using acetone as the anti-solvent. Accordingly, in another aspect, the invention provides a method for preparing crystalline form FH2, which method comprises forming saturated solution of form FH1 in DMF and then adding acetone to precipitate form FH2.

Form FH3

In another embodiment, the invention provides (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 9.35.

Preferably, the XRPD pattern also exhibits diffraction angle (2θ/°) peaks at 10.40, 10.78, 12.51, 14.78, 18.74, 19.09, 21.68, 22.32, 23.07, 24.86, 25.14 and 29.02.

More preferably, the XRPD pattern further exhibits diffraction angle (2θ/°) peaks at 5.83, 10.78, 11.35, 11.71, 13.35, 13.81, 14.10, 17.18, 17.65, 19.46, 20.11, 21.18, 23.71, 26.49, 27.03, 28.09, 28.70 and 29.52.

Figure 10:
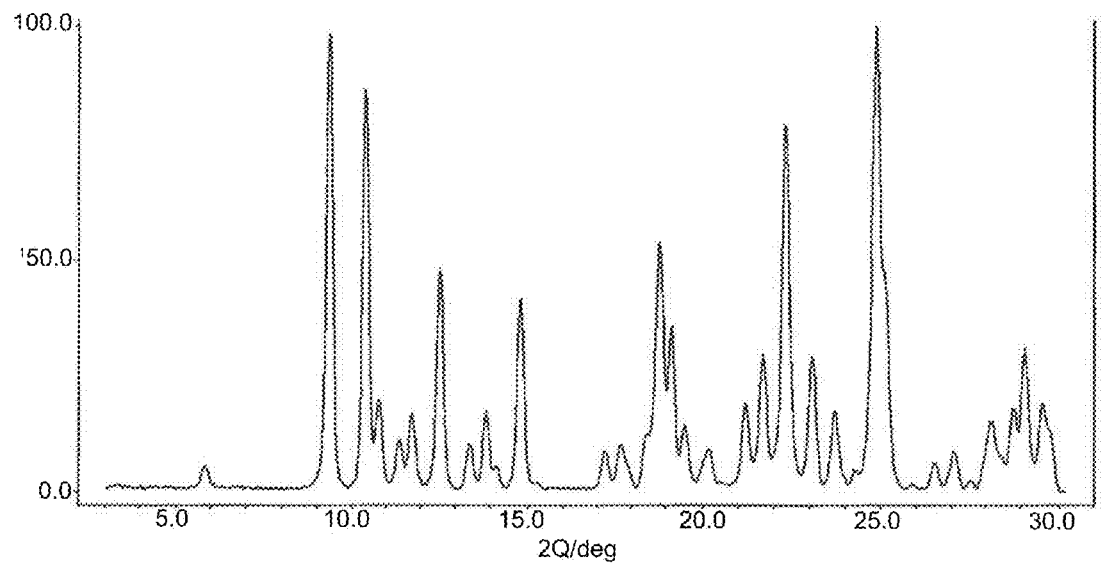
FIG. 10 depicts (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 9.35.

Most preferably, the XRPD pattern is substantially as shown in FIG. 10 herein.

Form FH3 can be prepared by adding HCl in dioxane to an ethanolic solution of (2,4-dihydroxy-5-isopropyl-phenyl)-[5-(4-methyl-piperazin-1-ylmethyl)-1,3-dihydro-isoindol-2-yl]-methanone free base. Accordingly, in another aspect, the invention provides a method of preparing the hydrochloride salt form FH3, which method comprises (i) dissolving 2,4-dihydroxy-5-isopropyl-phenyl)-[5-(4-methyl-piperazin-1-ylmethyl)-1,3-dihydro-isoindol-2-yl]-methanone free base in ethanol, (ii) adding thereto a solution of hydrogen chloride in dioxane; (iii) evaporating the resulting mixture to dryness; (iv) dissolving the residue in warm ethanol:water (9:1; 5 mL); (v) seeding the solution and stirring the solution for a period of at least two hours (e.g. at least 4 or 6 or 8 or 10 or 12 or 14 hours), and removing the precipitated form FH3.

Form FH4

In another embodiment, the invention provides (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 11.62.

Preferably, the XRPD pattern also exhibits diffraction angle (2θ/°) peaks at 7.04, 11.62, 15.54, 16.68, 18.54, 20.73, 22.26, 22.94, 23.77 and 25.07.

More preferably, the XRPD pattern further exhibits diffraction angle (2θ/°) peaks at 9.89, 12.30, 13.27, 14.14, 16.06, 17.99, 19.24, 23.36, 24.63, 25.72, 26.91 and 27.63.

Figure 11:
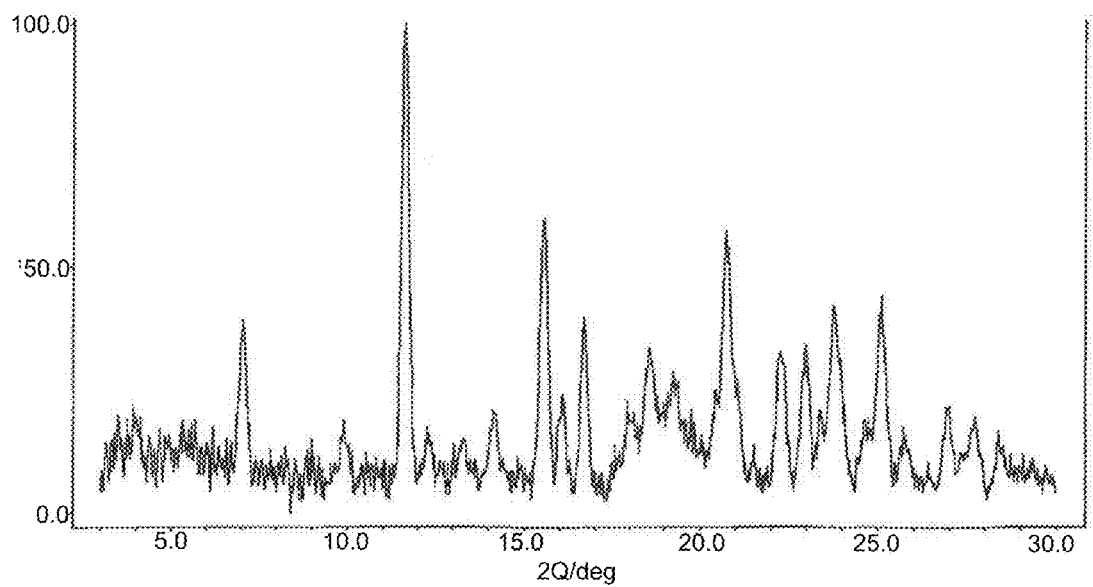
FIG. 11 depicts (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 11.62.

Most preferably, the XRPD pattern is substantially as shown in FIG. 11 herein.

Form FH4 can be prepared by precipitation from DMF solution using 1,4-dioxane as the anti-solvent. Accordingly, in another aspect, the invention provides a method for preparing crystalline form FH4, which method comprises forming saturated solution of form FH1 in DMF and then adding 1,4-dioxane to precipitate form FH4.

Form FH5

In another embodiment, the invention provides (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 2.32.

Preferably, the XRPD pattern also exhibits diffraction angle (2θ/°) peaks at 6.15, 11.79, 15.79, 20.81, 22.76 and 23.76.

Figure 12:
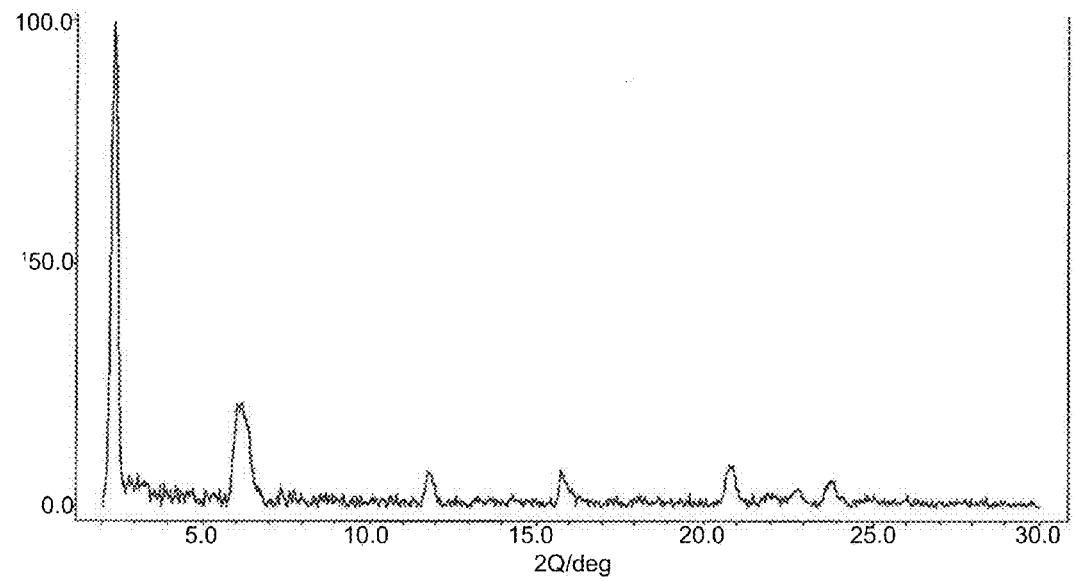
FIG. 12 depicts (2,4-dihydroxy-5-isopropyl-phenyl)-[5-(4-methyl-piperazin-1-ylmethyl)-1,3-dihydro-isoindol-2-yl]-methanone hydrochloride salt in a crystalline form characterised by an XRPD pattern having a diffraction angle (2θ/°) peak at 2.32.

Most preferably, the XRPD pattern is substantially as shown in FIG. 12 herein.

Form FH5 can be prepared by precipitation from a saturated methanol solution using acetone as the anti-solvent.

Crystalline forms of the salts formed between (2,4-dihydroxy-5-isopropyl-phenyl)-[5-(4-methyl-piperazin-1-ylmethyl)-1,3-dihydro-isoindol-2-yl]-methanone and L-lactic acid The lactic acid salts of the compound of formula (1) exist in one unstable form (FL3) and two stable forms (FL1 and FL2).

Form FL1

In another embodiment, the invention provides (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 16.81.

Preferably, the XRPD pattern also exhibits diffraction angle (2θ/°) peaks at 6.53, 13.10, 14.13, 14.40, 17.22, 18.65, 19.52, 19.82, 22.33, 22.84 and 23.09.

More preferably, the XRPD pattern further exhibits diffraction angle (2θ/°) peaks at 6.18, 8.39, 11.08, 15.21, 16.21, 20.49, 20.76, 21.13, 22.02, 23.94, 25.19, 26.41, 26.95 and 27.81.

Figure 13:
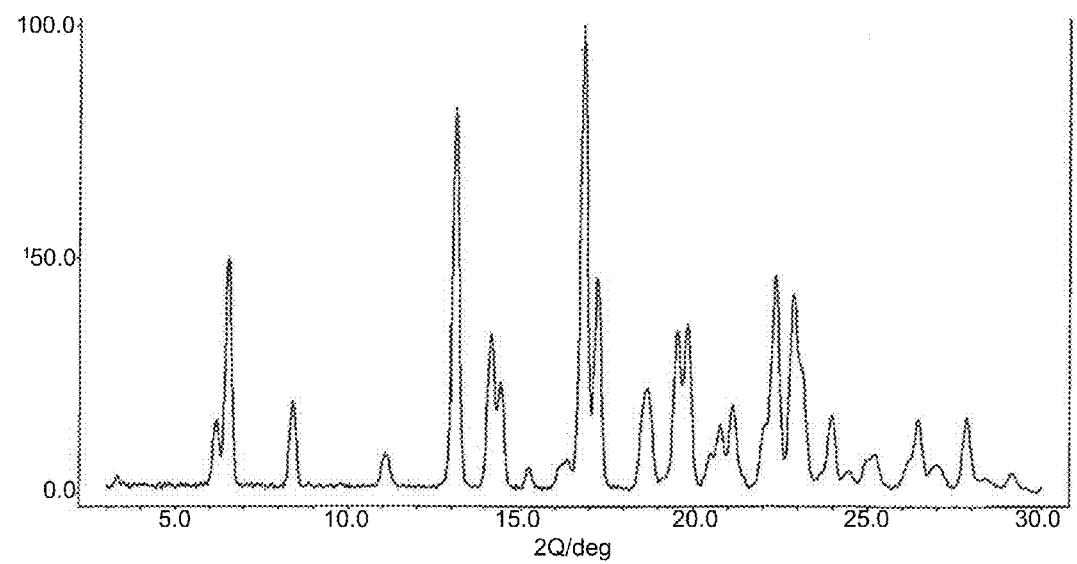
FIG. 13 depicts (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 16.81.

Most preferably, the XRPD pattern is substantially as shown in FIG. 13 herein.

Form FL1 can be prepared by suspending (2,4-dihydroxy-5-isopropyl-phenyl)-[5-(4-methyl-piperazin-1-ylmethyl)-1,3-dihydro-isoindol-2-yl]-methanone free base in a mixture of ethanol and EtOAc (e.g. in a volume ratio of 3:5); adding L-lactic acid to the mixture (e.g. wherein the L-lactic acid is in the form of a solution in ethanol); clarifying the mixture (e.g. by heating until clear and/or filtering off any remaining solid); stirring the clarified mixture with seeding and removing crystallised form FL1, e.g. by filtration.

Form FL2

In another embodiment, the invention provides (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 22.34.

Preferably, the XRPD pattern also exhibits diffraction angle (2θ/°) peaks at 8.03, 10.71, 11.98, 13.13, 15.39, 16.09, 16.61, 17.26, 18.17, 18.82, 20.40, 21.01, 21.53, 22.34, 22.56, 23.71 and 27.70.

More preferably, the XRPD pattern further exhibits diffraction angle (2θ/°) peaks at 24.30, 24.65, 26.56 and 28.29.

Figure 14:
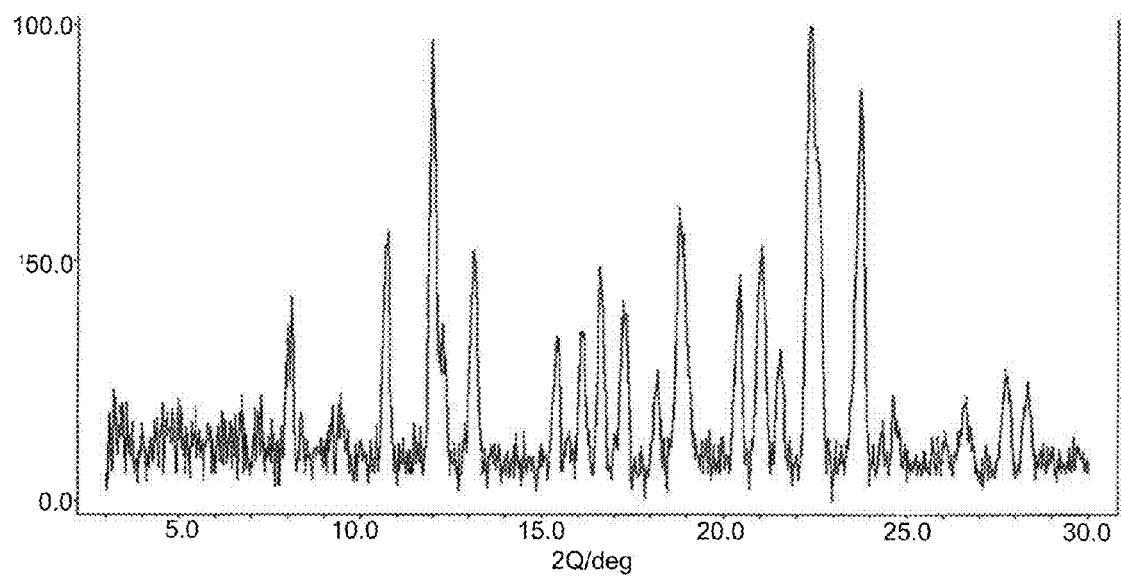
FIG. 14 depicts (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 22.34.

Most preferably, the XRPD pattern is substantially as shown in FIG. 14 herein.

Figure 15:
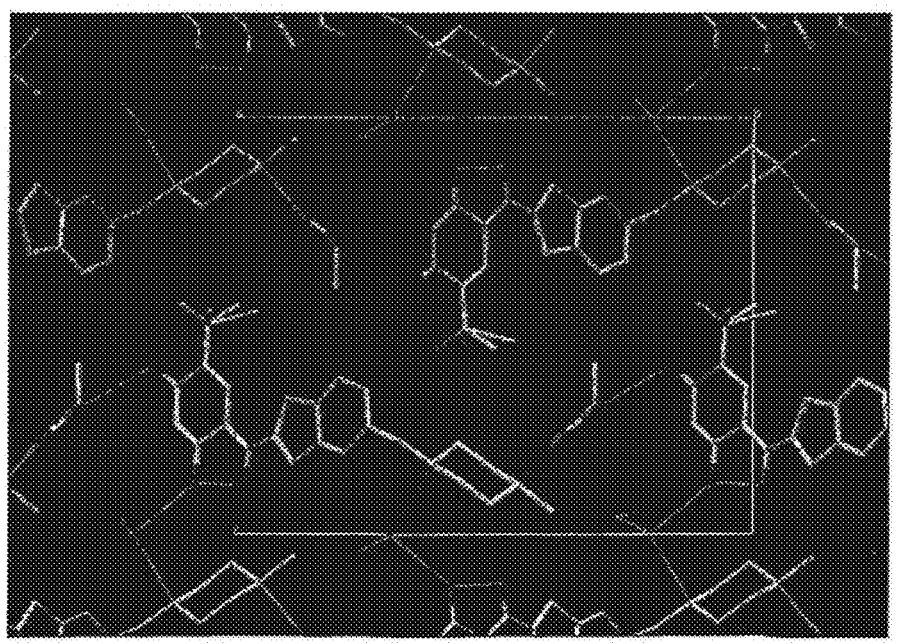
FIG. 15 depicts a crystal structure that belongs belong to the monoclinic space group P21 and has crystal lattice parameters at 293 K a=5.8 b=16.6, c=14.9 Å, β=98 α=γ=90°.

From X-ray crystallography studies, it has been found that form FL2 has a crystal structure that belongs belong to the monoclinic space group P21 and has crystal lattice parameters at 293 K a=5.8 b=16.6, c=14.9 Å, β=98 α=γ=90°. The crystal packing diagram for FL2 is shown in FIG. 15 herein.

Accordingly, in another embodiment, the invention provides (2,4-dihydroxy-5-isopropyl-phenyl)-[5-(4-methyl-piperazin-1-ylmethyl)-1,3-dihydro-isoindol-2-yl]-methanone L-lactate which is crystalline and:
(a) has a crystal structure as set out in FIG. 15; and/or
(b) has a crystal structure as defined by the coordinates in Table 16 herein; and/or
(c) has crystal lattice parameters at 293 K a=5.8 b=16.6, c=14.9 Å, β=98 α=γ=90°; and/or
(d) has a crystal structure that belongs belong to a monoclinic space group such as P21.

Crystalline form FL2 is a stable hydrate which is nominally a trihydrate since there are three crystal; water positions in the asymmetric unit but they are not 100% occupied at room temperature and humidity. Form FL2 may be used for the preparation of solid pharmaceutical compositions. Accordingly, in another aspect, the invention provides a solid pharmaceutical composition comprising 2,4-dihydroxy-5-isopropyl-phenyl)-[5-(4-methyl-piperazin-1-ylmethyl)-1,3-dihydro-isoindol-2-yl]-methanone L-lactate in crystalline form FL2 as defined herein.

Form FL2 can be prepared by precipitation from a saturated aqueous methanolic solution using acetone as the anti-solvent. Accordingly, in another aspect, the invention provides a method for preparing crystalline form FL2, which method comprises forming saturated solution of form FL in methanol:water (preferably in a 9:1 ratio) and then adding acetone to precipitate form FL2.

Form FL3

In another embodiment, the invention provides (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 5.53.

Preferably, the XRPD pattern also exhibits diffraction angle (2θ/°) peaks at 11.07, 13.16, 16.69, 17.17, 18.00, 18.49, 19.28, 21.05, 22.47 and 22.84.

More preferably, the XRPD pattern further exhibits diffraction angle (2θ/°) peaks at 8.36, 13.85, 19.79, 20.34, 21.47, 21.93, 24.56, 26.28, 27.06, 27.47 and 29.11.

Figure 16:
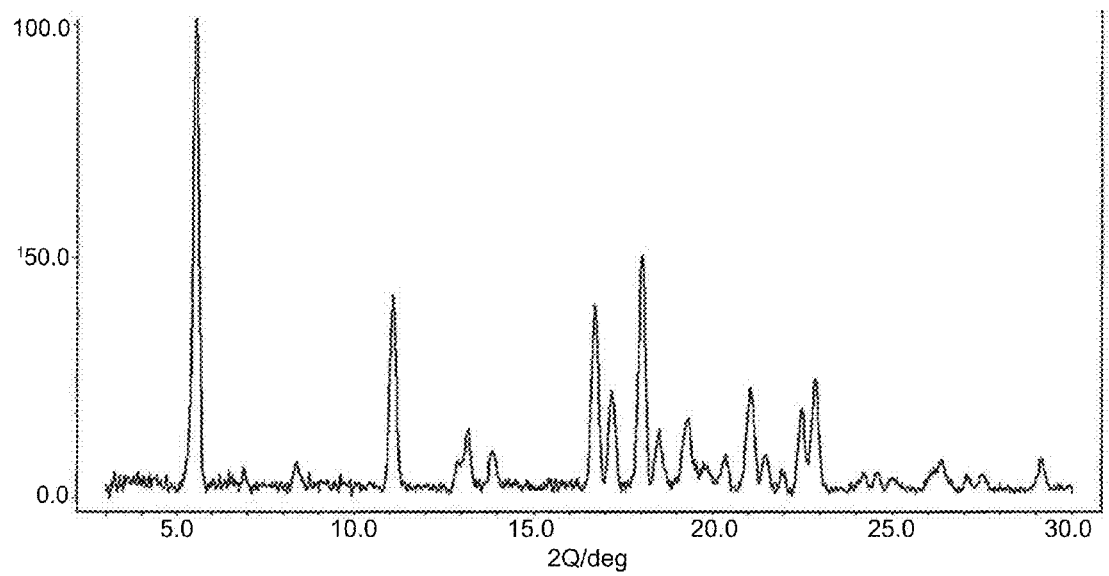
FIG. 16 depicts (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 5.53.

Most preferably, the XRPD pattern is substantially as shown in FIG. 16 herein.

Form FL3 is an unstable form that can be made by precipitation from a saturated THF solution using heptane as the anti-solvent. Accordingly, in another aspect, the invention provides a method for preparing crystalline form FL3, which method comprises forming a saturated solution of form FL1 in THF and then adding heptane to precipitate form FL3.

Crystallline forms of the salts formed between (2,4-dihydroxy-5-isopropyl-phenyl)-[5-(4-methyl-piperazin-1-ylmethyl)-1,3-dihydro-isoindol-2-yl]-methanone and sulphuric acid The sulphuric acid salts exist in two unstable forms (FS1 and FS2) and four stable forms (FS3, FS4. FS5 and FS6).

A 1:1 salt can be prepared by dissolving (2,4-dihydroxy-5-isopropyl-phenyl)-[5-(4-methyl-piperazin-1-ylmethyl)-1, 3-dihydro-isoindol-2-yl]-methanone free base in sulphuric acid and then evaporating to dryness.

Form FS1

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ%) peak at 4.79.

Preferably, the XRPD pattern also exhibits diffraction angle (2θ/°) peaks at 10.02, 11.28, 14.38, 15.27, 16.91, 18.29, 20.12, 21.76 and 22.32.

More preferably, the XRPD pattern further exhibits diffraction angle (2θ/°) peaks at 10.68, 12.89, 17.64, 18.86, 19.28, 20.82, 21.21, 22.89, 23.83, 24.22, 24.42, 25.13 and 29.04.

Figure 17:
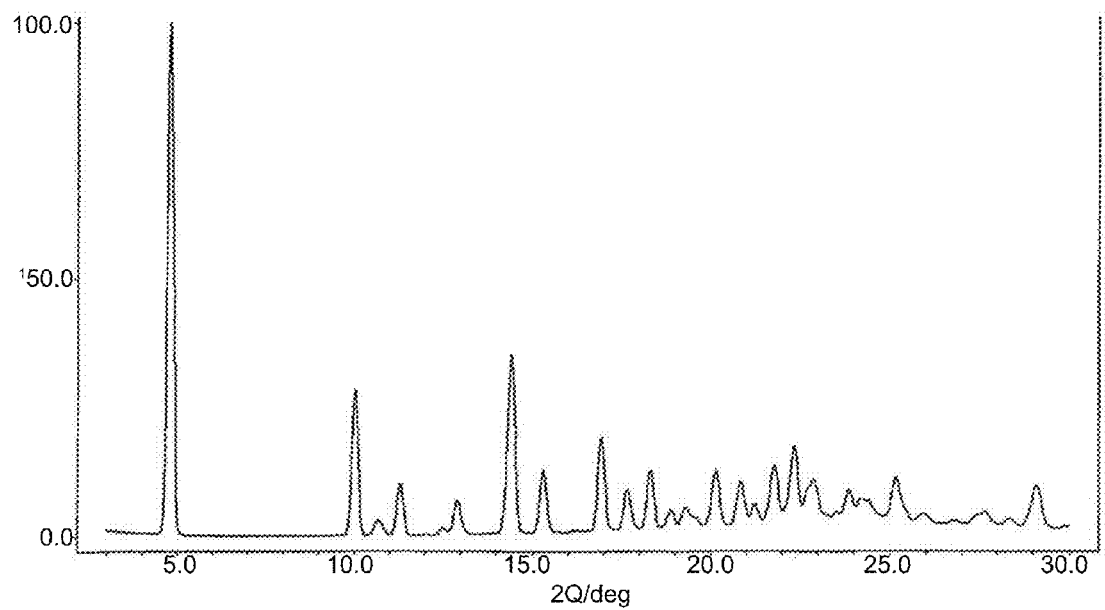
FIG. 17 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 4.79.

Most preferably, the XRPD pattern is substantially as shown in FIG. 17 herein.

Form FS1 can be prepared by preparing a saturated solution of the 1:1 salt (see above) in water at room temperature and then slowly adding acetonitrile to precipitate the form FS1.

Accordingly, in another aspect, the invention provides a method for preparing crystalline form FS1, which method comprises forming a saturated solution of form the 1:1 salt in water and then adding acetonitrile to precipitate form FS1.

Form FS2

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle ($2\theta$/°) peak at 7.43.

Preferably, the XRPD pattern also exhibits diffraction angle ($2\theta$/°) peaks at 7.03, 8.67, 11.76, 13.84, 17.50 and 23.20.

More preferably, the XRPD pattern further exhibits diffraction angle ($2\theta$/°) peaks at 4.17, 8.09, 9.27, 9.65, 10.41, 10.98, 12.53, 14.55, 15.39, 16.24, 16.89, 18.05, 18.93, 19.47, 24.21, 25.21, 25.75, 26.62 and 27.67.

Figure 18:
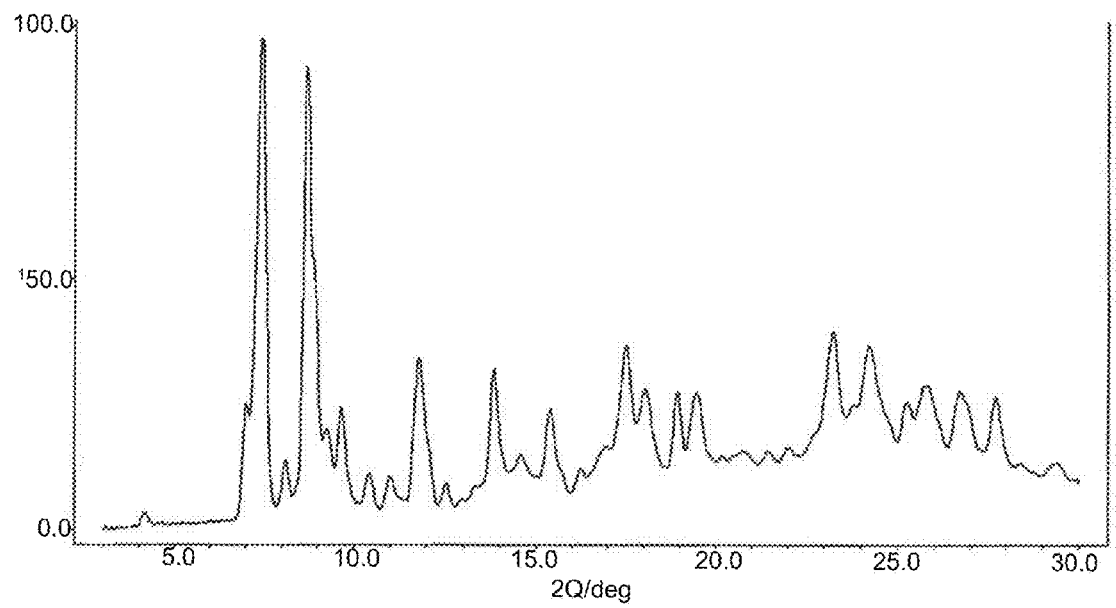
FIG. 18 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 7.43.

Most preferably, the XRPD pattern is substantially as shown in FIG. 18 herein.

In another aspect, the invention provides a method for making Form FS2, which method comprises dissolving Compound (1) in concentrated $H_2SO_4$ and adding acetonitrile (e.g. 4 volumes relative to the $H_2SO_4$) to precipitate the form FS2.

Form FS3

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle ($2\theta$/°) peak at 5.43.

Preferably, the XRPD pattern also exhibits diffraction angle ($2\theta$/°) peaks at 10.30, 11.24, 14.26, 14.91, 16.41, 17.53, 18.38, 18.61, 19.01, 19.92, 21.77, 22.67, 24.23 and 25.36.

More preferably, the XRPD pattern further exhibits diffraction angle ($2\theta$/°) peaks at 4.81, 12.94, 13.98, 15.62, 19.38, 20.27, 20.71, 21.19, 23.79, 27.38 and 28.82.

Figure 19:
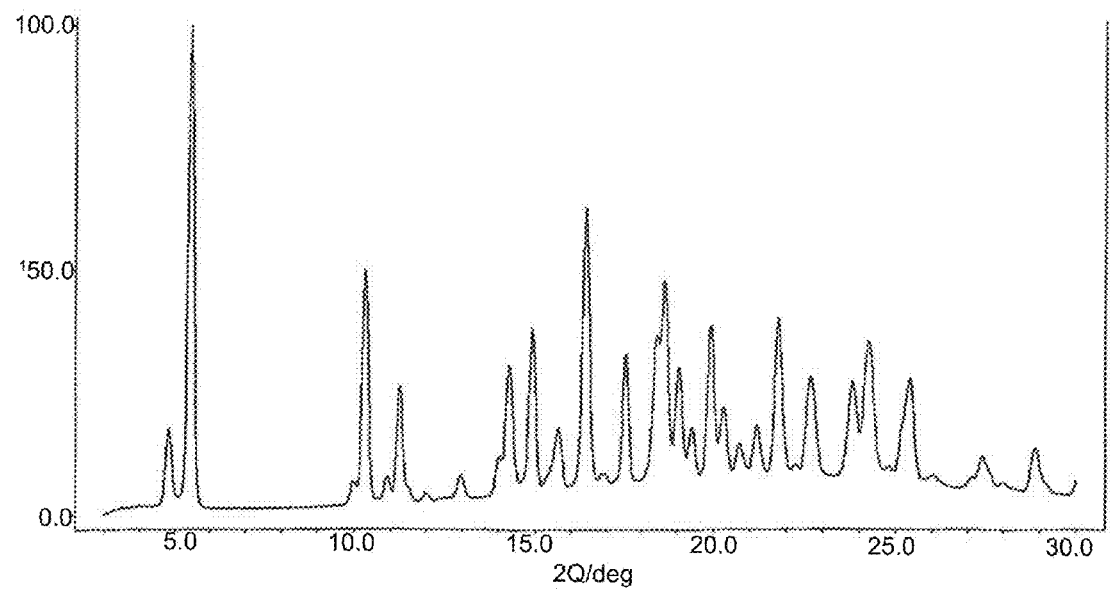
FIG. 19 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 5.43.

Most preferably, the XRPD pattern is substantially as shown in FIG. 19 herein.

Form FS3 can be prepared by allowing form FS1 to dry for 2 days in air.

Form FS4

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle ($2\theta$/°) peak at 7.48.

Preferably, the XRPD pattern also exhibits diffraction angle ($2\theta$/°) peaks at 7.16, 7.97, 8.82, 9.09, 9.37, 10.45, 11.77, 14.36, 16.21, 16.99, 17.28, 17.59, 18.90, 23.13, 23.68 and 23.96.

More preferably, the XRPD pattern further exhibits diffraction angle ($2\theta$/°) peaks at 4.64, 8.42, 13.25, 13.54, 15.03, 17.96, 19.43, 19.83, 21.36, 24.77, 25.64, 26.19, 26.73, 27.20, 27.76 and 28.64.

Figure 20:
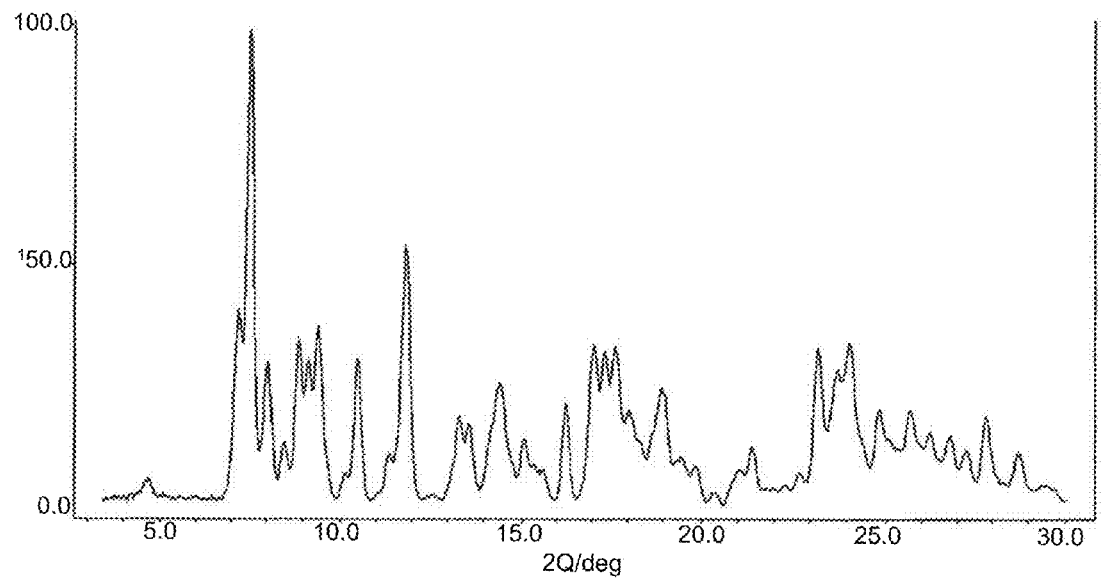
FIG. 20 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 7.48.

Most preferably, the XRPD pattern is substantially as shown in FIG. 20 herein.

Form FS4 can be prepared by incubating form FS2 for several weeks at 40° C. and 75% RH.

Form FS5

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle ($2\theta$/°) peak at 7.99.

Preferably, the XRPD pattern also exhibits diffraction angle ($2\theta$/°) peaks at 7.11, 9.33, 9.57, 10.45, 11.64, 13.27, 14.28, 15.60, 16.98, 17.65, 18.01, 18.80, 23.21, 23.51, 23.92, 25.06 and 26.24.

More preferably, the XRPD pattern further exhibits diffraction angle ($2\theta$/°) peaks at 4.70, 14.65, 15.12, 19.32, 19.83, 21.08, 24.30, 27.28 and 28.67.

Figure 21:
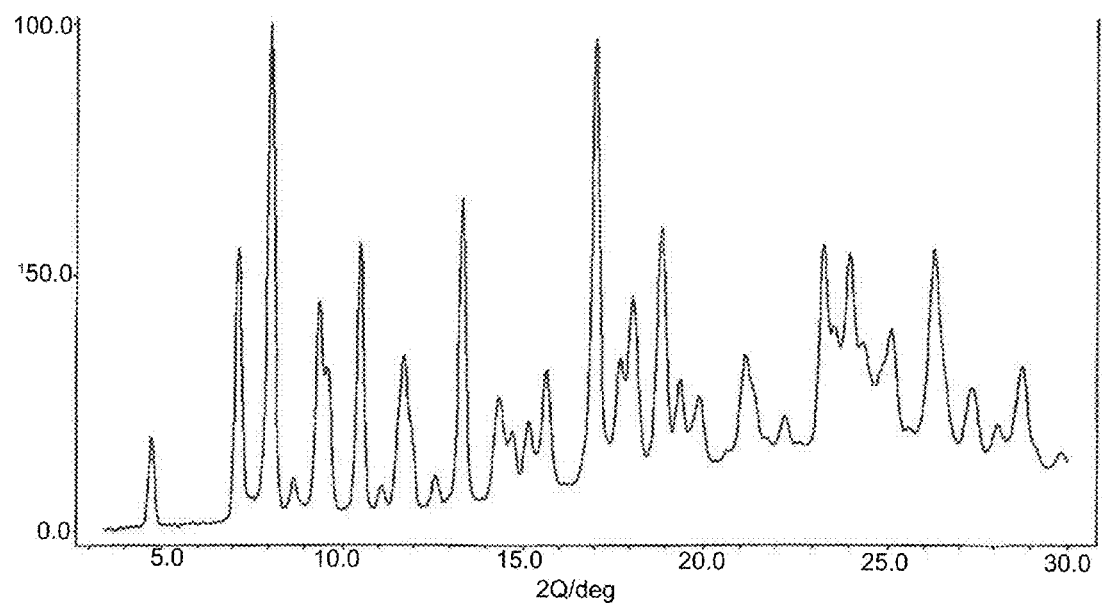
FIG. 21 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 7.99.

Most preferably, the XRPD pattern is substantially as shown in FIG. 21 herein.

Form FS5 can be prepared by preparing by allowing form FS2 to dry in air.

Form FS6

In another embodiment, the invention provides (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle ($2\theta$/°) peak at 4.82.

Preferably, the XRPD pattern also exhibits diffraction angle ($2\theta$/°) peaks at 9.98, 14.45, 15.38, 16.97, 18.18, 20.23, 20.93 and 22.29.

More preferably, the XRPD pattern further exhibits diffraction angle ($2\theta$/°) peaks at 11.35, 12.92, 17.52, 19.42, 21.31, 21.66, 21.89, 22.84, 23.04, 23.94, 24.51, 25.26 and 29.18.

Figure 22:
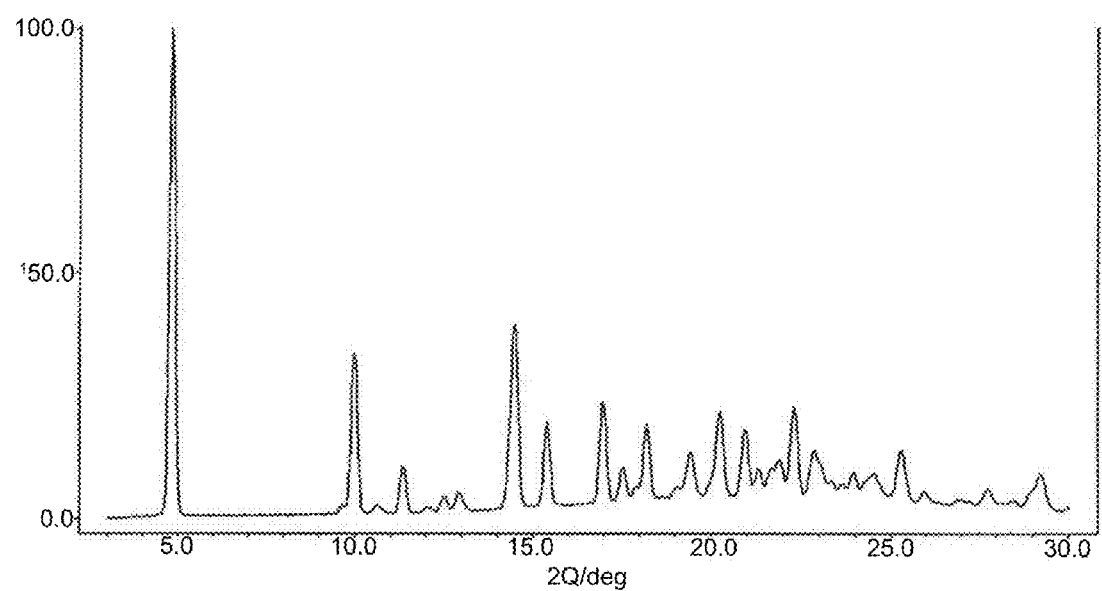
FIG. 22 depicts (2,4-dihydroxy-5-isopropyl-phenyl)-[5-(4-methyl-piperazin-1-ylmethyl)-1,3-dihydro-isoindol-2-yl]-methanone sulphate salt in a crystalline form characterised by an XRPD pattern having a diffraction angle (2θ/°) peak at 4.82.

Most preferably, the XRPD pattern is substantially as shown in FIG. 22 herein.

Form FS6 can be prepared by preparing a saturated solution of the 1:1 salt (see above) in DMF and then adding toluene to precipitate the form FS6.

PHARMACEUTICAL USES OF THE ACID ADDITION SALTS AND CRYSTALLINE FORMS OF COMPOUND (1)

In other aspects, the invention provides:

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in the prophylaxis or treatment of a disease state or condition mediated by Hsp90.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for the prophylaxis or treatment of a disease state or condition mediated by Hsp90.

A method for the prophylaxis or treatment of a disease state or condition mediated by Hsp90, which method comprises administering to a subject in need thereof an acid addition salt (e.g. an L-lactate salt) of a compound of the formula (1) as defined herein, or a crystalline form of a compound of the formula (1) or an acid addition salt (e.g. an L-lactate salt) thereof as defined herein.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in alleviating or reducing the incidence of a disease state or condition mediated by Hsp90.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for alleviating or reducing the incidence of a disease state or condition mediated by Hsp90.

A method for alleviating or reducing the incidence of a disease state or condition mediated by Hsp90, which method comprises administering to a subject in need thereof an acid addition salt (e.g. an L-lactate salt) of a compound of the formula (1) as defined herein, or a crystalline form of a compound of the formula (1) or an acid addition salt (e.g. an L-lactate salt) thereof as defined herein.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in treating a disease or condition comprising or arising from abnormal cell growth in a mammal.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for treating a disease or condition comprising or arising from abnormal cell growth in a mammal.

A method for treating a disease or condition comprising or arising from abnormal cell growth in a mammal, which method comprises administering to the mammal an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective in inhibiting abnormal cell growth.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in alleviating or reducing the incidence of a disease or condition comprising or arising from abnormal cell growth in a mammal.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, as defined herein for the manufacture of a medicament for alleviating or reducing the incidence of a disease or condition comprising or arising from abnormal cell growth in a mammal.

A method for alleviating or reducing the incidence of a disease or condition comprising or arising from abnormal cell growth in a mammal, which method comprises administering to the mammal an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective in inhibiting abnormal cell growth.

A method for treating a disease or condition comprising or arising from abnormal cell growth in a mammal, the method comprising administering to the mammal an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective to inhibit Hsp90 activity.

A method for alleviating or reducing the incidence of a disease or condition comprising or arising from abnormal cell growth in a mammal, the method comprising administering to the mammal an acid addition salt (e.g. an L-lactate salt) of a compound of the formula (1) as defined herein, or a crystalline form of a compound of the formula (1) or an acid addition salt (e.g. an L-lactate salt) thereof as defined herein, an amount effective to inhibit Hsp90 activity.

A compound of the formula (10) as defined herein for use as an inhibitor of Hsp90.

A method of inhibiting Hsp900, which method comprises contacting the Hsp90 with an Hsp90-inhibiting acid addition salt (e.g. an L-lactate salt) of a compound of the formula (1) as defined herein, or a crystalline form of a compound of the formula (1) or an acid addition salt (e.g. an L-lactate salt) thereof as defined herein.

An acid addition salt (e.g. an L-lactate salt) of a compound of the formula (1) as defined herein, or a crystalline form of a compound of the formula (1) or an acid addition salt (e.g. an L-lactate salt) thereof as defined herein, herein for use in modulating a cellular process (for example cell division) by inhibiting the activity of Hsp90.

A method of modulating a cellular process (for example cell division) by inhibiting the activity of Hsp90 using an acid addition salt (e.g. an L-lactate salt) of a compound of the formula (1) as defined herein, or a crystalline form of a compound of the formula (1) or an acid addition (e.g. an L-lactate salt) salt thereof as defined herein, as defined herein.

A an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in the prophylaxis or treatment of a disease state as described herein.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament, wherein the medicament is for any one or more of the uses defined herein.

A pharmaceutical composition comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier.

A pharmaceutical composition comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for oral administration.

A pharmaceutical composition comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for parenteral administration, for example by intravenous (i.v.) administration.

A pharmaceutical composition comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for intravenous (i.v.) administration by injection or infusion.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in medicine.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for any of the uses and methods set forth above, and as described elsewhere herein.

An acid addition salt (e.g. an L-lactate salt) of a compound of the formula (1) as defined herein, or a crystalline form of a compound of the formula (1) or an acid addition salt (e.g. an L-lactate salt) thereof as defined herein, for use in treatment or prophylaxis of a disease state or condition in a patient who has been screened and has been determined as suffering from, or being at risk of suffering from, a disease or condition which would be susceptible to treatment with a compound having activity against Hsp90.

The use of an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90.

A method for the diagnosis and treatment of a disease state or condition mediated by Hsp900, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient an acid addition salt (e.g. an L-lactate salt) of a compound of the formula (1) as defined herein, or a crystalline form of a compound of the formula (1) or an acid addition salt (e.g. an L-lactate salt) thereof as defined herein.

NOVEL PROCESSES

The invention also provides novel processes for preparing a compound of the formula (1), analogues thereof, and their acid addition salts (e.g. an L-lactate salt) and also novel processes for preparing key intermediates in the synthesis of the compound of formula (1).

Accordingly, in another aspect, the invention provides a process for the preparation of a compound of the formula (2):

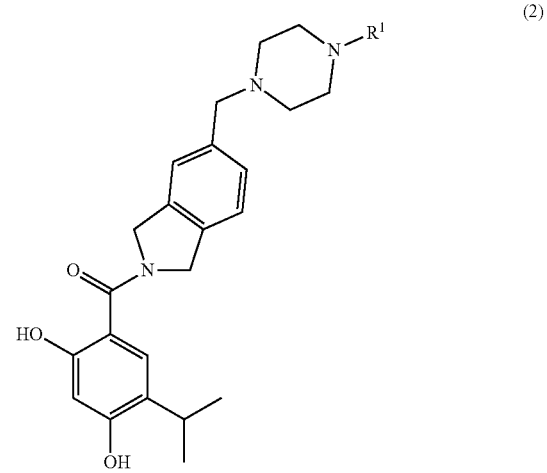

wherein R1 is $C_{1-4}$ alkyl; which process comprises subjecting to catalytic hydrogenation a compound of the formula (3):

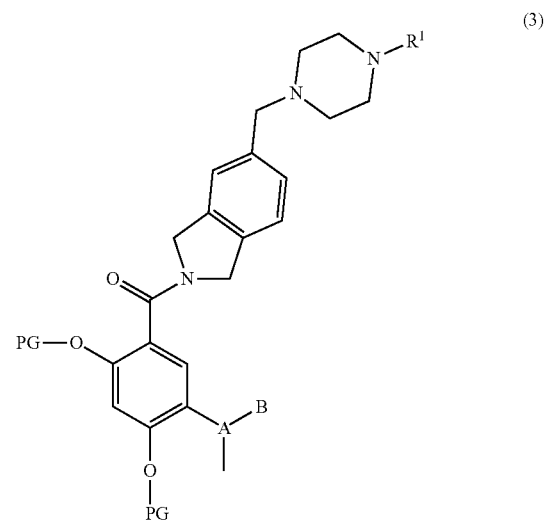

wherein PG is a protecting group removable under hydrogenation conditions and A-B is CH—$CH_3$ or C=$CH_2$ and, when the product of the process is a free base, thereafter optionally converting the compound of formula (2) into an acid addition salt (e.g. an L-lactate salt).

The protecting group PG is preferably a benzyl group.
The moiety A-B can be either CH—$CH_3$ or C=$CH_2$.
In one embodiment, the moiety A-B is C=$CH_2$.
In another embodiment, the moiety A-B is CH—$CH_3$.
The catalytic hydrogenation is typically carried out using a palladium catalyst, for example palladium on carbon (palladium on charcoal).

The above process may be used to prepare a compound of formula (1) or its ethyl, propyl and butyl homologues. Preferably the process is used to prepare compounds wherein $R^1$ is methyl or ethyl.

In one embodiment, $R^1$ is methyl, i.e. the process is used to prepare the compound formula (1).

In another embodiment, $R^1$ is ethyl.

Compounds of the formula (3) can be prepared by the reaction of a compound of the formula (3a):

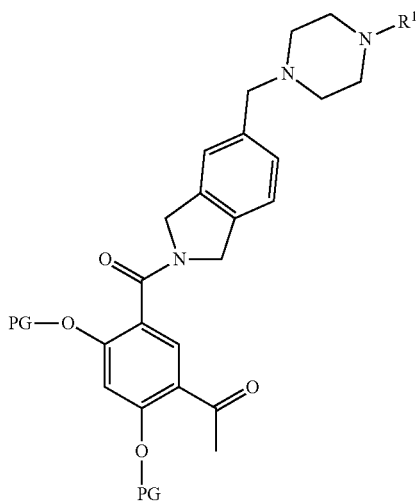
(3a)

with a Wittig reagent or other reagent suitable for converting the group —C(=O)—CH$_3$ into a group —C(=CH$_2$)—CH$_3$. For example, the acetophenone compound (3a) can be reacted with the Wittig reagent MePPh3Br in the presence of a base such as butyl lithium or potassium tert-butoxide in THF to give a compound of formula (3) wherein A-B is C=CH$_2$.

Thus, in another aspect, the invention provides a process for the preparation of a compound of the formula (3) as defined herein, which process comprises the reaction of a compound of the formula (3a) as hereinbefore defined with a Wittig reagent or other reagent suitable for converting the group —C(=O)—CH$_3$ into a group —C(=CH$_2$)—CH$_3$.

Alternatively, and more preferably, compounds of the formula (3) can be prepared by the reaction of a substituted benzoic acid of the formula (4) below, or an activated form or derivative thereof, with an isoindoline of the formula (5) below.

Accordingly, in a further aspect, the invention provides a process for the preparation of a compound of the formula (3) as defined herein, which process comprises:

(a-i) the reaction of a compound of the formula (4), or an activated form or derivative thereof with a compound of the formula (5):

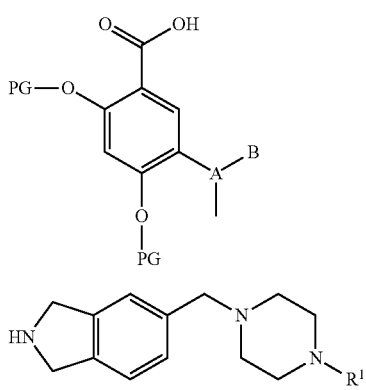

(4)

(5)

under amide forming conditions.

The invention further provides a process for the preparation of a compound of the formula (2) as defined herein, which process comprises:

(a-i) the reaction of a compound of the formula (4) as defined herein, or an activated form or derivative thereof with a compound of the formula (5) as defined herein, under amide forming conditions to give a compound of the formula (3); and (b) subjecting the compound of formula (3) to catalytic hydrogenation to remove the protecting groups PG and, when A-B is C=CH$_2$, reduce the group A-B to an isopropyl group and, when the product of the process is a free base, thereafter optionally converting the compound of formula (2) into an acid addition salt (e.g. an L-lactate salt).

Prior to reacting the benzoic acid (4) with the isoindoline (5), the benzoic acid may first be converted to an acid chloride by treatment with thionyl chloride, or by reaction with oxalyl chloride in the presence of a catalytic amount of dimethyl formamide, or by reaction of a potassium salt of the acid with oxalyl chloride. The acid chloride can then be reacted with the isoindoline (5) in the presence of a non-interfering base such as triethylamine. The reaction may be carried out at around room temperature in a polar solvent such as dioxan.

As an alternative to using the acid chloride method described above, the benzoic acid (4) can be reacted with the isoindoline (5) in the presence of amide coupling reagents of the type commonly used in the formation of amide or peptide linkages. Examples of such reagents include 1,1'-carbonyldiimidazole (CDI), 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.,* 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino) phosphonium hexafluorophosphate (PyBOP) (Castro et al, *Tetrahedron Letters,* 1990, 31, 205). Carbodiimide-based coupling agents are advantageously used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.* 103, 708, 2024-2034). Preferred coupling reagents include EDC (EDAC) and DCC in combination with HOAt or HOBt.

One particular coupling reagent comprises EDC in combination with HOBt.

A preferred coupling agent is 1,1'-carbonyldiimidazole (CDI).

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room. The reaction may be carried out in the presence of a non-interfering base, for example a tertiary amine such as triethylamine or N,N-diisopropylethylamine.

The compounds of formula (4) wherein A-B is C=CH$_2$ can be prepared by the sequence of reactions shown in Scheme 1.

Scheme 1

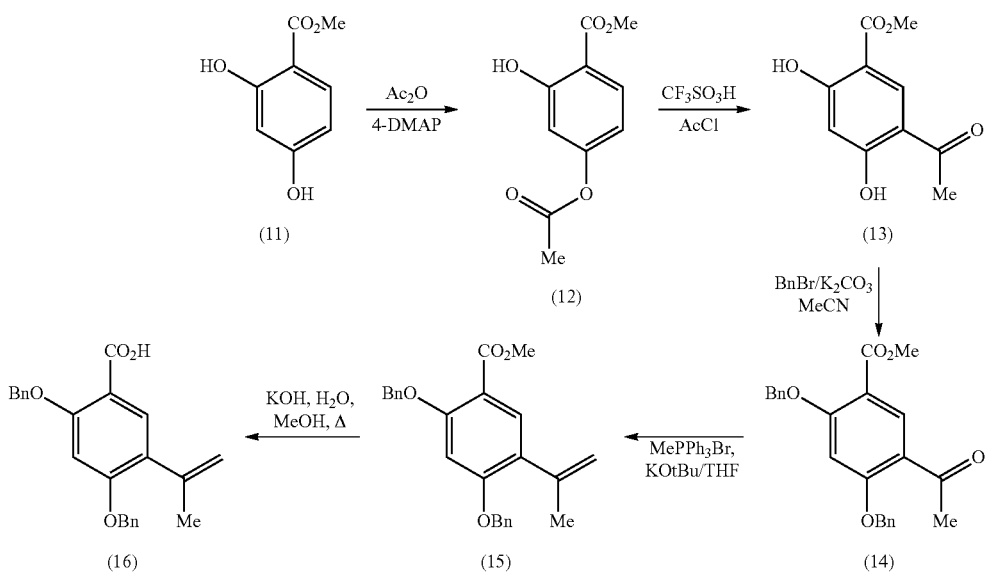

The starting material for Scheme 1 is 2,4-dihydroxybenzoic acid methyl ester (11) which is monoacetylated by reaction with acetic anhydride in the presence of N,N-dimethyl-4-aminopyridine to give the di-ester (12). Conversion of the di-ester (12) to the substituted acetophenone (13) is achieved by reacting compound (12) with trifluoromethanesulphonic acid and optionally acetyl chloride to give the acetophenone (13). The acetophenone (13) is treated with benzyl bromide in the presence of a base such as potassium carbonate to give the dibenzyl compound (14) which is then reacted with the Wittig reagent MePPh3Br in the presence of a base such as butyl lithium or potassium tert-butoxide in THF to give the isopropenyl compound (15). The ester hydrolysis to the carboxylic acid (16) is typically carried out by treatment with an aqueous alkali metal hydroxide such potassium sodium hydroxide. The hydrolysis reaction may be carried out using an organic co-solvent such as an alcohol (e.g. methanol) and the reaction mixture is typically heated to a non-extreme temperature, for example up to about 50-90° C.

Compounds of the formula (4) where A-B is CH—CH3 can be prepared as described in Scheme 1 except that the isopropenyl compound (15) is reduced to the corresponding isopropyl compound by catalytic hydrogenation, and the resulting dihydroxy-compound is then re-benzylated by reaction with benzyl bromide in the presence of a base as described above.

The reaction sequence illustrated in Scheme 1 above gives rise to yields that are significantly better than the yields in the corresponding steps in Scheme 4 of PCT/GB2006/001382 and make use of reagents and conditions that are better suited to manufacturing scale synthesis. Furthermore, and most importantly from the perspective of large scale synthesis, the reaction sequence shown in Scheme 1 avoids the need for chromatographic purification Accordingly, the invention provides a process ("Intermediate Process A") for the preparation of a compound of the formula (13):

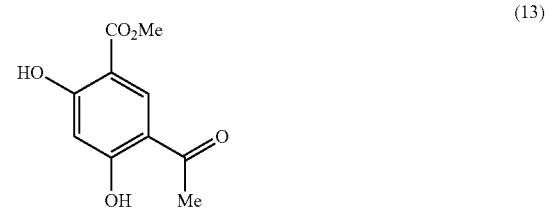 [SMILES: COC(=O)c1cc(C(C)=O)c(O)cc1O]

which process comprises:

(i) the reaction of a compound of the formula (1):

with (a) acetic anhydride in the presence of 4-dimethylaminopyridine (typically with heating, e.g. to a temperature of up to about 60°), followed by (b) trifluoromethanesulphonic acid and optionally acetyl chloride (typically at room temperature); or (ii) the reaction of a compound of the formula (11) with acetyl chloride in the presence of a cationic ion-exchange resin such as Amberlyst™ 15 resin.

Intermediate Process A gives yields of compound (13) that are better than the yields disclosed for the corresponding process in PCT/GB2006/001382.

The invention also provides a process ("Intermediate Process B") for the preparation of a compound of the formula (15):

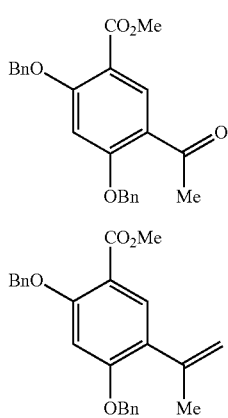

by reacting a compound of the formula (14) with a Wittig reagent MePPh3Br in the presence of potassium tert-butoxide in THF.

Intermediate Process B gives a significantly better yield of product than yield disclosed for the corresponding process step in PCT/GB2006/001382 where n-butyl lithium is used as the base in the Wittig reaction. In addition, the potassium tert-butoxide base is better suited to a manufacturing scale process than n-butyl lithium and the reaction can be carried out at room temperature or with only moderate cooling whereas the use of n-butyl lithium typically requires the reaction mixture to be cooled to temperatures of 0° C. or lower. Chromatographic purification is not required.

In a further aspect, the invention provides a process for making a compound of the formula (16) as defined herein, which process comprises Intermediate Process B followed by hydrolysis of the methyl ester group in compound (15) using an alkali metal hydroxide such as potassium hydroxide to give the compound of formula (16).

The isoindoline compounds (5) can be prepared by the synthetic route illustrated in Scheme 2.

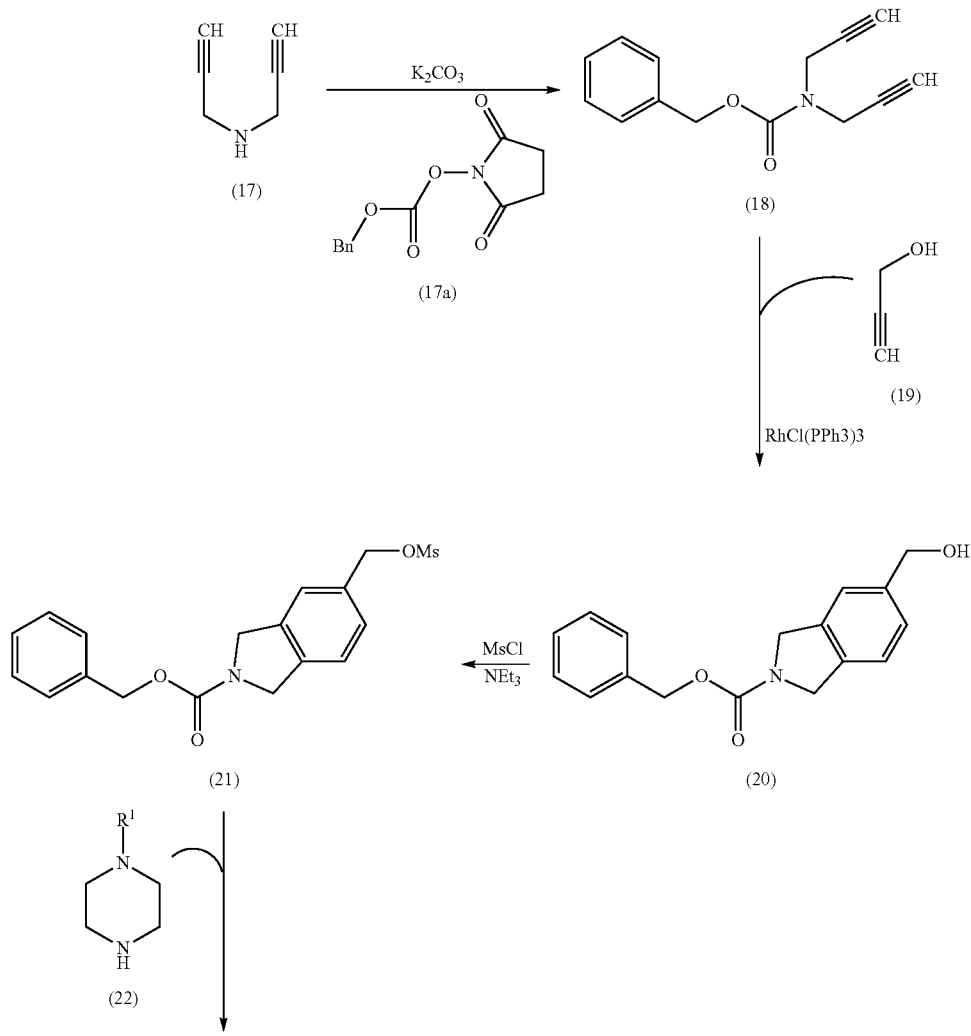

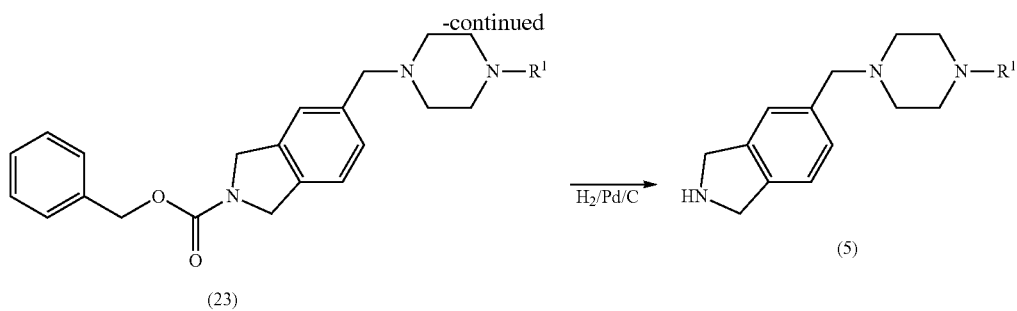

In Scheme 2, the dipropargylamine (17) is reacted with N-(benzyloxycarbonyloxy) succinimide (17a) in ethyl acetate in the presence of potassium carbonate to give the Z-protected dipropargylamine (18) (the term "Z" referring to a benzyloxycarbonyl group). As an alternative to N-(benzyloxycarbonyloxy) succinimide, benzyl chloroformate may be used to introduce the benzyloxycarbonyl protecting group. Compound (18) is then reacted with propargyl alcohol (19) in the presence of Wilkinson's catalyst in a 2+2+2 cycloaddition reaction to give the Z-protected isoindoline (20). The hydroxymethyl group on the isoindoline (20) is then converted to a mesyloxy group by reaction with methanesulphonyl chloride in a polar solvent such as THF in the presence of a non-interfering base such as triethylamine to give the mesyl compound (21). The mesyl compound (21) is reacted with alkylpiperazine (22) in acetone solution to give the Z-protected isoindoline (23). Removal of the benzyloxycarbonyl group to give the unprotected isoindoline compound (5) is then accomplished by hydrogenation over a palladium on charcoal catalyst.

A variation on the reaction sequence shown in Scheme 2 is illustrated in Scheme 2a.

Scheme 2a

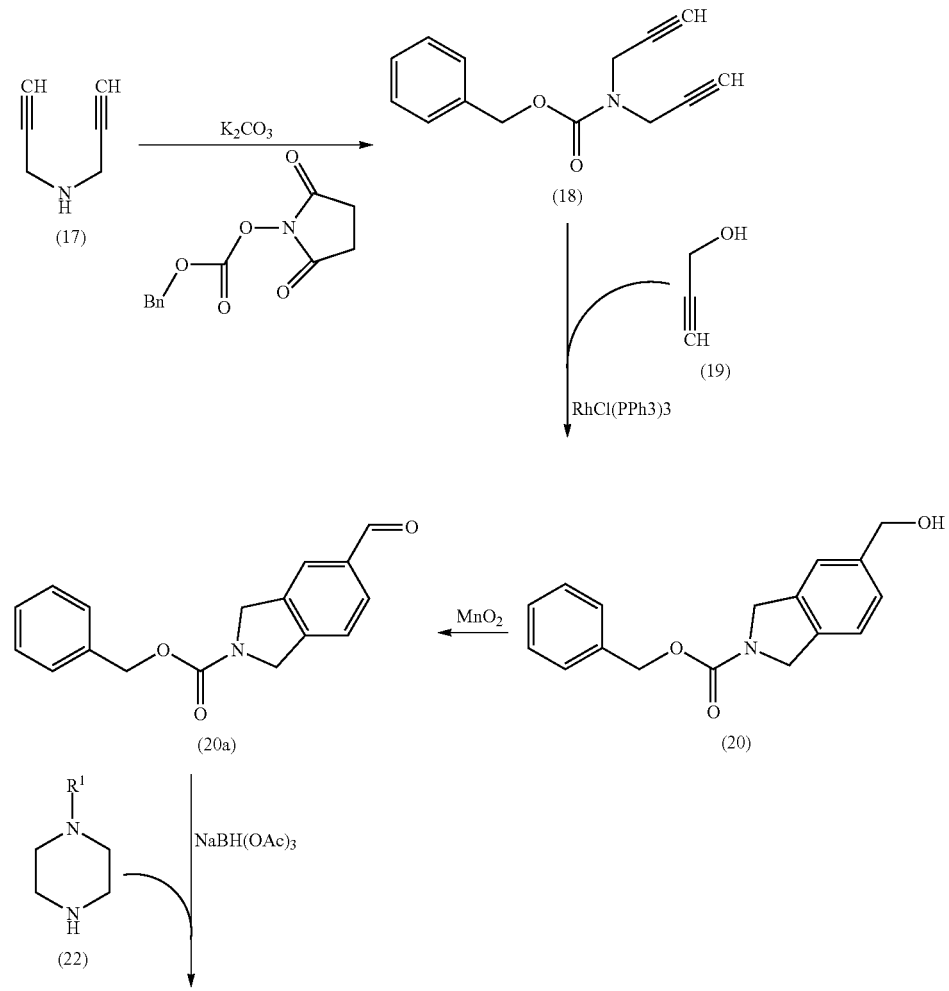

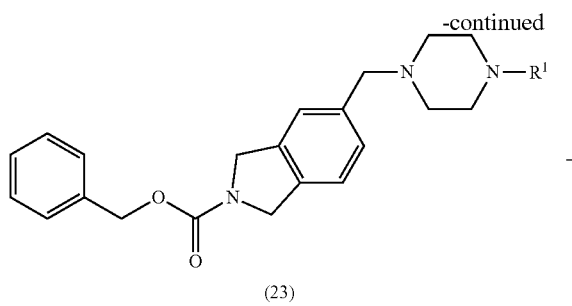

(23)

In Scheme 2a, rather than being converted to the mesylate (21), the hydroxymethylindoline (20) is oxidised to the corresponding aldehyde (21a) using manganese dioxide in dichloromethane, and the aldehyde is then converted to a compound of the formula (23) by reaction with a compound of the formula (22) under reductive amination conditions, e.g. in the presence of sodium triacetoxyborohydride. The Z-group is then removed by hydrogenation as described above in respect of Scheme 2 to give the intermediate (5).

Accordingly, in another aspect, the invention provides a process for the preparation of a compound of the formula (5) as defined herein, which process comprises:

(i) the reaction of a compound of the formula (24):

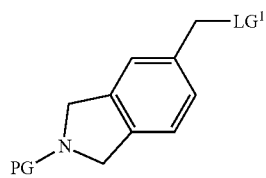

(24)

wherein PG is a protecting group (such as benzyloxycarbonyl) and LG1 is a leaving group (such as mesyloxy), with a compound of the formula (22) as defined herein; or (ii) the reaction of a compound of the formula (25):

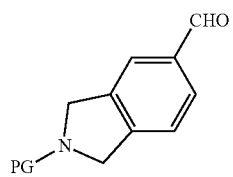

(25)

wherein PG is a protecting group (such as benzyloxycarbonyl), with a compound of the formula (22) as defined herein under reductive amination conditions (e.g. in the presence of sodium triacetoxyborohydride;

and thereafter removing the protecting group PG, e.g. by hydrogenation when PG is a benzyloxycarbonyl group.

In Schemes 2 and 2a, the intermediate (20) is prepared by means of a 2+2+2 cycloaddition reaction in the presence of a transition metal catalyst. As an alternative to the 2+2+2 cycloaddition reaction, the intermediate (20) can be prepared by the sequence of reactions shown in Scheme 3.

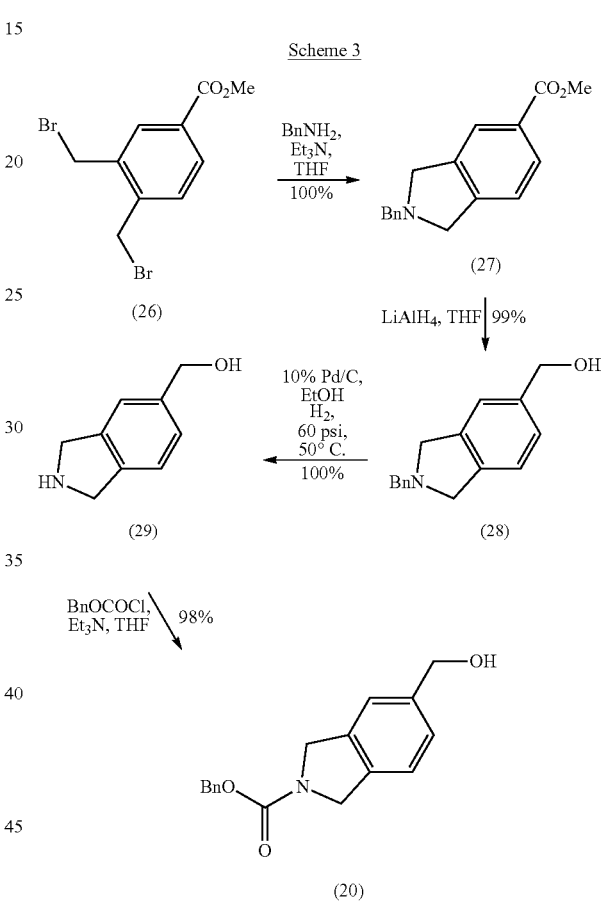

In Scheme 3, the bis-bromomethyl benzoic acid ester (26) is reacted with benzylamine in a polar aprotic solvent such as tetrahydrofuran (THF) in the presence of a non-interfering base such as triethylamine to give the N-benzyl dihydroisoindole intermediate (27). The ester group in intermediate (27) is then reduced to the corresponding alcohol using lithium aluminium hydride in THF to give the hydroxymethyldihydroisoindole intermediate (28). Debenzylation of the hydroxymethyldihydroisoindole intermediate (28) is then carried out by hydrogenation over palladium on charcoal catalyst in an alcohol (e.g. ethanol) solvent at a mildly elevated temperature (e.g. up to about 50°) to give the intermediate (29). Intermediate (29) is then converted to intermediate (20) by reaction with a reagent suitable for introducing a benzyloxycarbonyl ("Z") group onto the nitrogen atom of the dihydroisoindole ring. For example, the intermediate (29) can be reacted with benzyl chloroformate in a polar non-protic solvent such as THF in the presence of a non-interfering base such as triethylamine to give intermediate (20).

A substantial advantage of the synthetic routes shown in Schemes 2, 2a and 3 is that the various intermediate products formed along the route have excellent physicochemical properties that are highly beneficial in large scale synthesis. Thus, when combined with the sequence of steps in Scheme 1, the result is a synthetic route that has significant advantages over the corresponding synthetic routes in our earlier application PCT/GB2006/001382. In particular, the main advantages include:

higher yields
easier purification (chromatographic purification not required)
improved physicochemical properties of intermediates leading to easier handling
easier to scale up to a manufacturing process In another aspect, the invention provides a process for the preparation of a compound of the formula (6):

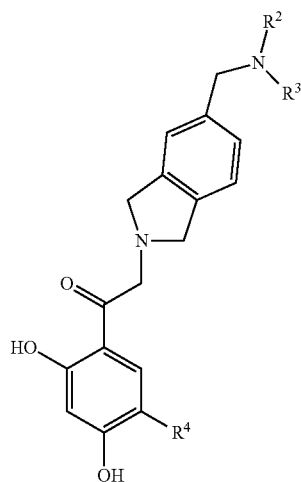

(6)

wherein $R^2$ and $R^3$ are the same or different and each is $C_{1-4}$ alkyl or $NR^2R^3$ forms a 4 to 7 membered saturated heterocyclic ring optionally containing a further heteroatom selected from O, N and S and optionally substituted by one or two $C_{1-4}$ alkyl groups; and $R^4$ is selected from hydrogen, halogen, $C_{1-5}$ alkyl and $C_{3-4}$ cycloalkyl groups;

which process comprises:

(a-ii) the reaction of a compound of the formula (7):

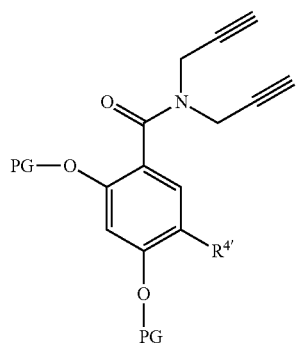

(7)

wherein PG is a protecting group removable under hydrogenation conditions and $R^{4'}$ is selected from hydrogen, halogen, $C_{1-5}$ alkyl, $C_{2-5}$ alkenyl and $C_{3-4}$ cycloalkyl groups; with a compound of the formula (8):

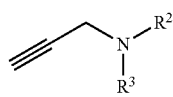

(8)

in the presence of a transition metal catalyst to give a compound of the formula (9);

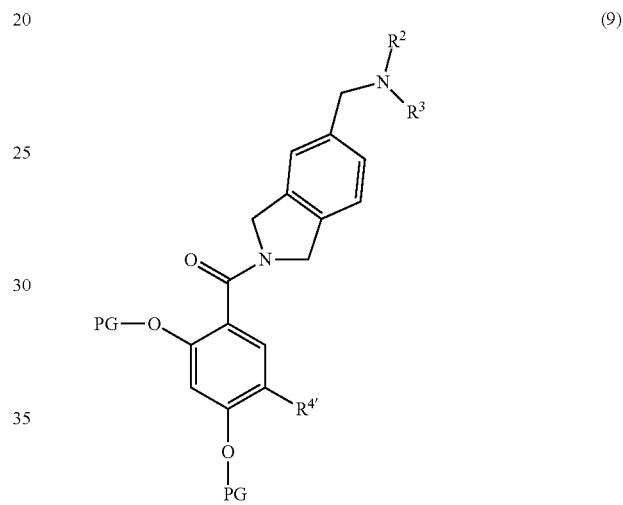

(9)

and (b) subjecting the compound of formula (9) to catalytic hydrogenation to remove the protecting groups PG and, when $R^{4'}$ is $C_{2-5}$ alkenyl, reduce the group $R^{4'}$ to $C_{2-5}$ alkyl;

and thereafter, where the compound of formula (6) is prepared in the form of a free base, optionally converting the free base to an acid addition salt.

The invention further provides a process for the preparation of a compound of the formula (9) as defined herein, which process comprises:

(a-ii) the reaction of a compound of the formula (7) as defined herein, with a compound of the formula (8) as defined herein, in the presence of a transition metal catalyst.

The reaction of the compound of formula (7) with the compound of formula (8) is an example of a 2+2+2 cycloaddition (see the review by C. P. Dell, J. Chem. Soc., Perkin Trans. I, 1998, 3873-3905 and the references therein). The reaction is typically carried out in an inert solvent such as toluene, with heating (e.g. to a temperature in the range room temperature to 100° C.) in the presence of a transition metal catalyst. A preferred catalyst is Wilkinson's catalyst-chlorotris (triphenylphosphine) rhodium ($RhCl(PPh_3)_3$).

In one particular embodiment, the compound of formula (8) is a compound of the formula (8a):

(8a)

wherein $R^1$ is as defined herein, and preferably is methyl or ethyl.

The compound of formula (8a) can be prepared by reacting propargyl bromide with a compound of the formula (22) (see Scheme 2) in a polar solvent such as acetone in the presence of a base such potassium carbonate.

In one embodiment, $R^1$ is methyl, i.e. the process is used to prepare the compound of formula (1).

In another embodiment, $R^1$ is ethyl.

In formulae (7) and (9), $R^{4'}$ is selected from hydrogen, halogen, $C_{1-5}$alkyl, $C_{2-5}$ alkenyl and $C_{3-4}$ cycloalkyl groups. In one preferred embodiment, $R^{4'}$ is isopropyl or isopropenyl, and more particularly is isopropenyl.

NOVEL CHEMICAL INTERMEDIATES

Chemical intermediates of the formula (3), (3a), (5), (7), (9), (14), (15), (16), (20), (20a), (21) and (23) above are believed to be novel and, as such, each form a further aspect of the invention.

A NOVEL HSP90 INHIBITOR COMPOUND

In another aspect, the invention provides a novel compound of the formula (2) as defined herein wherein $R^1$ is ethyl. The novel compound can be represented by the formula (10):

(10)

Also embraced by formula (10) are any salts, solvates, crystalline forms, tautomers, N-oxides and isotopic variations thereof.

The invention further provides inter alia:

A compound of the formula (10) as defined herein for use in the prophylaxis or treatment of a disease state or condition mediated by Hsp90.

The use of a compound of the formula (10) as defined herein for the manufacture of a medicament for the prophylaxis or treatment of a disease state or condition mediated by Hsp90.

A method for the prophylaxis or treatment of a disease state or condition mediated by Hsp900, which method comprises administering to a subject in need thereof a compound of the formula (10) as defined herein.

A compound of the formula (10) as defined herein for use in alleviating or reducing the incidence of a disease state or condition mediated by Hsp90.

The use of a compound of the formula (10) as defined herein for the manufacture of a medicament for alleviating or reducing the incidence of a disease state or condition mediated by Hsp90.

A method for alleviating or reducing the incidence of a disease state or condition mediated by Hsp90, which method comprises administering to a subject in need thereof a compound of the formula (10) as defined herein.

A compound of the formula (10) as defined herein for use in treating a disease or condition comprising or arising from abnormal cell growth in a mammal.

The use of a compound of the formula (10) as defined herein for the manufacture of a medicament for treating a disease or condition comprising or arising from abnormal cell growth in a mammal.

A method for treating a disease or condition comprising or arising from abnormal cell growth in a mammal, which method comprises administering to the mammal a compound of the formula (10) as defined herein in an amount effective in inhibiting abnormal cell growth.

A compound of the formula (10) as defined herein for use in alleviating or reducing the incidence of a disease or condition comprising or arising from abnormal cell growth in a mammal.

The use of a compound of the formula (10) as defined herein for the manufacture of a medicament for alleviating or reducing the incidence of a disease or condition comprising or arising from abnormal cell growth in a mammal.

A method for alleviating or reducing the incidence of a disease or condition comprising or arising from abnormal cell growth in a mammal, which method comprises administering to the mammal a compound of the formula (10) as defined herein in an amount effective in inhibiting abnormal cell growth.

A method for treating a disease or condition comprising or arising from abnormal cell growth in a mammal, the method comprising administering to the mammal a compound of the formula (10) as defined herein in an amount effective to inhibit Hsp90 activity.

A method for alleviating or reducing the incidence of a disease or condition comprising or arising from abnormal cell growth in a mammal, the method comprising administering to the mammal a compound of the formula (10) as defined herein in an amount effective to inhibit Hsp90 activity.

A compound of the formula (10) as defined herein for use as an inhibitor of Hsp90.

A method of inhibiting Hsp90, which method comprises contacting the Hsp90 with an Hsp90-inhibiting compound of the formula (10) as defined herein.

A compound of the formula (10) as defined herein for use in modulating a cellular process (for example cell division) by inhibiting the activity of Hsp90.

A method of modulating a cellular process (for example cell division) by inhibiting the activity of Hsp90 using a compound of the formula (10) as defined herein.

A compound of the formula (10) as defined herein for use in the prophylaxis or treatment of a disease state as described herein.

The use of a compound of the formula (10) as defined herein for the manufacture of a medicament, wherein the medicament is for any one or more of the uses defined herein.

A pharmaceutical composition comprising a compound of the formula (10) as defined herein and a pharmaceutically acceptable carrier.

A pharmaceutical composition comprising a compound of the formula (10) as defined herein and a pharmaceutically acceptable carrier in a form suitable for oral administration.

A pharmaceutical composition comprising a compound of the formula (10) as defined herein and a pharmaceutically acceptable carrier in a form suitable for parenteral administration, for example by intravenous (i.v.) administration.

A pharmaceutical composition comprising a compound of the formula (10) as defined herein and a pharmaceutically acceptable carrier in a form suitable for intravenous (i.v.) administration by injection or infusion.

A compound of the formula (10) as defined herein for use in medicine.

A compound as defined herein for any of the uses and methods set forth above, and as described elsewhere herein.

A compound of the formula (10) as defined herein for use in treatment or prophylaxis of a disease state or condition in a patient who has been screened and has been determined as suffering from, or being at risk of suffering from, a disease or condition which would be susceptible to treatment with a compound having activity against Hsp90.

The use of a compound of the formula (10) as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90.

A method for the diagnosis and treatment of a disease state or condition mediated by Hsp900, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient a compound of the formula (10) as defined herein.

A reference to a compound of the formula (10) thereof also includes ionic forms, salts, solvates, tautomers, isotopes and protected forms thereof, for example, as discussed below.

Formula (10) includes compounds with one or more isotopic substitutions, and a reference to a particular element includes within its scope all isotopes of the element. For example, a reference to hydrogen includes within its scope $^1H$, $^2H$ (D), and $^1H$ (T). Similarly, references to carbon and oxygen include within their scope respectively $^{12}C$, $C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by formula (10) are any polymorphic forms of the compounds, solvates (e.g. hydrates), complexes (e.g. inclusion complexes or clathrates with compounds such as cyclodextrins, or complexes with metals) of the compounds

BIOLOGICAL ACTIVITY AND THERAPEUTIC USES

The compounds of the formulae (10) and (1) and the salts (particularly the L-lactate) and crystalline forms thereof are inhibitors of Hsp90 and consequently will be beneficial in the treatment of wide spectrum of proliferative disorders. Examples of such proliferative disorders are not limited to but can be selected from a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkett's lymphoma; a hematopoieitic tumour of myeloid lineage, for example acute chronic myelogenous leukaemias, Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoacanthoma; thyroid follicular cancer, or Kaposi's sarcoma. A further example of a tumour of mesenchymal origin is Ewing's sarcoma.

The cancers may be cancers which are sensitive to Hsp90 inhibition, and such cancers may be determined by a method as set out in the section headed "Methods of Diagnosis".

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma) and optionally further includes chronic myelogenous leukaemia and multiple myeloma.

A preferred sub-set of cancers consists of ErbB2-positive breast, prostate, lung, and gastric cancer; chronic myeloid leukemia; androgen receptor dependent prostate cancer; Flt3-dependent acute myeloid leukaemia; melanoma associated with Braf mutation; multiple myeloma; velcade refractory multiple myeloma; and gastrointestinal stromal tumours (GIST).

Of these, particularly preferred cancers are multiple myelomas and velcade refractory tumour types as defined herein.

Another preferred sub-set of cancers consists of hormone refractory prostate cancer, metastatic melanoma, HER2 positive breast cancer, mutant EGFR positive non-small cell lung carcinoma and Gleevec resistant gastrointestinal stromal tumours.

The Hsp90 inhibitor compounds of the formulae (10) and (1) and the salts (particularly the L-lactate) and crystalline forms thereof could also be used to treat other conditions such as viral infections, parasitic disease, autoimmune diseases (e.g. multiple sclerosis and lupus erythematosus), neuro-degenerative disorders (e.g. Alzheimer's disease), inflammation, Type I and II diabetes, atherosclerosis and cardiac disease.

The Hsp90 inhibitor compounds of the formulae (10) and (1) and the salts (particularly the L-lactate) and crystalline forms thereof could also have clinical benefit in transplantation and immunosuppression.

The Hsp90 inhibitor compounds of the formulae (10) and (1) and the salts (particularly the L-lactate) and crystalline forms thereof may also have clinical benefit in the previously described diseases when used in combination with existing or new therapeutic agents.

Based on the activities of Hsp90 client proteins and experimental evidence, the following disorders may be particularly sensitive to treatment by the Hsp90 inhibitor compounds of the formulae (10) and (1) and the salts (particularly the L-lactate) and crystalline forms thereof.

ErbB2-Positive Breast, Prostate, Lung, and Gastric Cancer

Overexpression of ErbB2 (HER-2) occurs in approximately 30% of breast cancers and ErbB2 receptor downregulation by herceptin sensitized cells to Taxol. ErbB2 over-expression is linked to poor prognosis and drug resistance (Tsugawa et. al., 1993. Oncology 1993; 50: 418).

Mutant EGFR in Lung Cancer

Somatic mutations in the kinase domain of the epidermal growth factor receptor (EGFR), including L858R and exon 19 deletions, underlie responsiveness to gefitinib and erlotinib in non-small cell lung cancer (NSCLC). Acquired resistance to these tyrosine kinase inhibitors is in some cases mediated by a second mutation, T790M. Ansamycin antibiotics, such as geldanamycin, potently inhibit heat shock protein 90 (Hsp90), promoting ubiquitin-mediated degradation of oncogenic kinases that require the chaperone for proper conformational folding. Exposure of EGFR-mutant cell lines to geldanamycin induced marked depletion of phospho-Akt and cyclin D1 as well as apoptosis. These data suggest mutational activation of EGFR is associated with dependence on Hsp90 for stability and that Hsp90 inhibition may represent a novel strategy for the treatment of EGFR-mutant NSCLC.

Chronic Myeloid Leukemia

The aberrant BCR-Abl protein is created through a chromosomal translocation and results in a constitutively active Abl kinase domain. This translocation event has been shown to be causal for CML. P210BcrAbl is a known client protein for Hsp90. Treatment of the BCR-Abl cell line K562 with an hsp90 inhibitor induced apoptosis. The Bcr-Abl inhibitor GleevecA) also induces apoptosis in K562 cells; however Gleevec® resistant K562 cells still retain sensitivity towards Hsp90 inhibitors (Gorre et. al. 2002, Blood 100: 3041-3044).

Androgen Receptor Dependent Prostate Cancer

The androgen receptor kinase is an Hsp90 client protein. Hormone replacement therapy is usually adopted where surgery does not resolve the cancer. The cancer may become refractory to hormone manipulation through receptor mutation. Hsp90 regulation of the receptor would still be viable post-mutation.

The same would apply to estrogen-dependent breast cancers.

Flt3-Dependent Acute Myeloid Leukaemia

Internal duplication of the tyrosine kinase receptor Flt3 leads to its constitutive activation and oncogenesis. These internal duplications are observed in 20% of all reported cases of AML and are an indication of poor prognosis. Much like the activation of the ABL kinase in CML, this represents another example of a single genetic lesion giving rise to a malignancy. Hsp90 inhibitors are predicted to be of clinical benefit to these patients as Flt3 is an Hsp90 client protein (Bali et. al., 2004 Cancer Res. 64(10):3645-52).

Melanoma Associated with Braf Mutation

Braf encodes for a serine/threonine kinase which is mutated in 70% of all melanomas. 80% of these represent a single V599E point mutation that confers elevated kinase activity to BRAF. This mutation is also transforming in NIH3T3 cells (Bignell et. al., 2002 Nature. 417(6892):949-54).

Multiple Myeloma

The Hsp90 inhibitor 17-AAG potently inhibits proliferation of Bortezomib refractory multiple myeloma cell lines. Cell surface levels of IGF-1R and IL-6R were also diminished in 17-aag treated MM-1 cells (Mitsiades et. al., Blood 107:1092-1100, 2006). Autocrine stimulation of multiple myeloma cells, as well as paracrine stimulation of bone marrow stromal cells with IL-6 is also diminished through downregulation of the Hsp90 client IKK.

Velcade Refractory Multiple Myeloma

The Hsp90 inhibitor compounds of the formulae (10) and (1) and the salts (particularly the L-lactate) and crystalline forms thereof can be used in the treatment of velcade refractory tumour types including treatment of patients with second line mantle cell lymphoma, indolent non-Hodgkin's lymphoma, stage IIIB and IV Bronchioloalveolar carcinoma, advanced non-small cell lung cancer, breast, prostate and ovarian cancers and non-Hodgkin's lymphoma.

Gastrointestinal Stromal Tumours (GIST)

GIST disease particularly disease dependent on growth factor activation or overexpression (e.g. c-kit)

Other conditions or disorders for which an Hsp90 inhibitor may be of clinical benefit include, but are not limited to:

Neurodegenerative Disorders

Huntington's disease (HD) is a progressive neurodegenerative disorder with no effective treatment. GA inhibition of Hsp90 and the resulting up-regulation of Hsps are effective in preventing huntington protein aggregation in neuronal cells. (Sittler et. al., 2001, Human Molecular Genetics, Vol. 10, No. 12 1307-1315). Up-regulation of HSP may also be of clinical benefit in other diseases of protein misfolding e.g., CJD and Alzheimer's.

Inflammatory Disease, Including Rheumatoid Arthritis, Asthma, Chronic Obstructive Pulmonary Disease, and Inflammatory Bowel Disease GA has been shown to dissociate HSF-1 from Hsp90 leading to the activation and nuclear translocation of HSF-1. HSF-1 subsequently acts as a transcription factor to induce HSP90 and Hsp70. The induction of Hsp70 has been implicated in the resolution of inflammation in an induced mouse model of edema (Ianaro et al., 2004 Human Molecular Genetics, 2001, Vol. 10, No. 12 1307-1315). Additionally GA treatment inhibited IkappaB kinase (IKK) activation by TNF-a or PMA. IkBa is a regulator of Nf-kB and Ap-1. (Broemer et. al. 2004). Ap-1 and Nf-kB is a major transcription factor leading to the production of pro-inflammatory cytokines (Yeo et. al., 2004 Biochem Biophys Res Commun. 30; 320(3):816-24). The stability of pro-inflammatory cytokine transcripts is also regulated through inhibition of p38 MapK (Wax et. al., 2003. Rheumatism Vol. 48, No. 2, pp 541-550).

Atherosclerosis

It is known that inflammatory and immune cells play a central role in the initiation and progression of human atherosclerosis (Riganò et al., Ann. N.Y. Acad. Sci., 2007, 1107:1-10) and it has been proposed that Hsp90 acts as an autoantigen in carotid atherosclerosis. Riganò et al. found specific antibodies and cells against Hsp90 in the sera of 60% of patients tested who were suffering from carotid atherosclerotic plaques but no specific antibodies and T cells against Hsp90 in the sera of healthy patients. Therefore, the Hsp90 inhibitor compounds of the formulae (10) and (1) and the salts (particularly the L-lactate) and crystalline forms thereof should be useful in the treatment or prevention of atherosclerosis.

Angiogenesis Related Disease, Including but not Limited to: Tumour Angiogenesis, Psoriasis, Rheumatoid Arthritis, and Diabetic Retinopathy Induction of angiogenesis is regulated by Hsp90 client proteins eNOS and Akt in endothelial cells (Sun and Liao, 2004 Arterioscler Thromb Vase Biol. 24(12):2238-44). Suppression of hypoxia-inducible factor (HIF)-1a can also impair the growth, angiogenesis and vessel maturation of gastric tumours in a mouse model. (Stoeltzing et. al., 2004 J Natl Cancer Inst; 96:946-956).

Type I and Type II Diabetes

Hsp900 inhibition has a profound effect on Akt signalling as well as e-nos. These are two key regulators in high glucose induced endothelial cell apoptosis in type I diabetes (Lin et. al., 2005 J Cell Biochem. 1; 94(1):194-201) and the development of hypertension in type II diabetes (Kobayashi et. al., 2004 Hypertension. 44(6):956-62).

Immunosuppression and Transplantation

Hsp90 inhibition has been shown to down regulate Lck, a T-cell specific tyrosine kinase required for T-cell activation. (Yorgin et. al., 2000 J. Immunol. 15; 164(6):2915-23)

Cardiac Disease

Cardiac ischemic is the most common cause of death in the western world. Hsps, and notably Hsp70 (induced by radicicol treatment) have demonstrated cardioprotective activity in rat cardiomyocytes (Griffin et. al., 2004). Inhibition of Hsp90 results in the release of HSF-1 from the chaperone complex and its subsequent activation of Hsp genes. Inhibition of Hsp90 also leads to the down-regulation of HIF-1, which has been implicated in the pathogenesis of ischemic heart disease and stroke.

Infectious Disease

Hepatitis C viral NS2/3 protease is an Hsp90 client protein and Hsp900 activity is required for viral processing and replication (Whitney et. al., 2001. Proc Natl Acad Sci USA. 20; 98(24): 13931-5).

Parasitic Disease

GA has reported antimalarial activity against an Hsp90 ortholog of *Plasmodium falciparum*. *Plasmodium* growth was inhibited with GA at an IC50 similar to that observed with chloroquine. GA was also effective against chloroquine resistant strains of *Plasmodium falciparum* (Kamar et. al., 2003. Malar J. 15; 2(1):30).

Inhibition, Prevention or Reversal of the Development of Drug Resistance

As discussed above, modulators or inhibitors of stress protein function in general (and Hsp90 in particular) represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

Accordingly, the invention further provides:

A method for the prophylaxis or treatment (or alleviation or reduction of the incidence) of a disease state or condition mediated by Hsp90, which method comprises administering to a subject in need thereof a compound of the invention, wherein the disease state or condition mediated by Hsp90 is the development of resistance to a cancer drug.

A method for: (i) sensitizing malignant cells to an anticancer drug; (ii) alleviating or reducing the incidence of resistance to an anticancer drug; (iii) reversing resistance to an anticancer drug; (iv) potentiating the activity of an anticancer drug; (v) delaying or preventing the onset of resistance to an anticancer drug, which method comprises administering to a subject in need thereof a compound of the invention.

A method for the treatment of a cancer which method comprises administering to a subject in need thereof a compound of the invention, which method is characterized by the absence of drug resistance.

A method for the prophylaxis or treatment (or alleviation or reduction of the incidence) of a disease state or condition mediated by Hsp90 in a subject undergoing treatment with a therapeutic agent (such as an anticancer agent), which method comprises administering to the subject a compound of the invention, wherein the disease state or condition mediated by Hsp90 is the development of resistance to the said therapeutic agent.

A method for: (i) sensitizing malignant cells to an anticancer agent; (ii) alleviating or reducing the incidence of resistance to an anti-cancer agent; (iii) reversing resistance to an anti-cancer agent; (iv) potentiating the activity of an anti-cancer agent; (v) delaying or preventing the onset of resistance to an anti-cancer agent, which method comprises administering to a subject undergoing treatment with said anti-cancer agent a compound of the invention.

A method for the treatment of a cancer in a subject undergoing treatment with an anti-cancer agent, which method comprises administering to a subject in need thereof a compound of the invention, which method is characterized by the absence of drug resistance to the anti-cancer agent.

Biological Activity

The biological activity of the compounds of the formulae (10) and (1) and the salts (particularly the L-lactate) and crystalline forms thereof, e.g. as inhibitors of Hsp90, can be measured using the assays set forth in the examples below, for example the isothermal titration calorimetry (ITC) experiments described in Example 6 and the anti-proliferative activity assays described in Example 7. The level of activity exhibited by a given compound in the ITC assay can be defined in terms of the $K_d$ value, and compounds of the present invention have a $K_d$ value of less than 1 micromolar. In the anti-proliferative activity assays, the level of activity exhibited by a given compound in an assay can be defined in terms of the $IC_{50}$ value, and the compounds of the invention each have an $IC_{50}$ value of less than 0.1 micromolar.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345 (6277):672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

The compound of the formula (1) has low hERG activity and a good separation between Hsp90 inhibitory activity and hERG activity. In particular, the compound of formula (1) has a mean IC50 value against hERG that is greater than 30 times the IC50 values of the compound in cellular proliferation assays. The compound of formula (1) has a mean IC50 value against hERG that is greater than 15 µM.

The compounds of the invention have advantageous ADME properties and in particular better tumour distribution.

TREATMENT OF PAIN, NEUROPATHIES, STROKE AND RELATED CONDITIONS

The compounds of the invention have Hsp90 inhibiting or modulating activity and hence are useful in for use in treating, alleviating or preventing certain cdk5 mediated diseases and conditions.

Accordingly, in a first aspect, the invention provides the use of a compound of the invention as defined herein for the manufacture of a medicament for the treatment of pain.

In another aspect, the invention provides the use of a compound of the invention as defined herein thereof for the manufacture of a medicament for the prophylaxis or treatment of stroke.

In a further aspect, the invention provides the use of a compound of the invention as defined herein for the manufacture of a medicament for use as a neuroprotective agent.

In other aspects, the invention provides:

A compound of the invention as defined herein for use in the treatment of pain.

A compound of the invention as defined herein for use in the reduction or elimination of pain in a patient (e.g. a mammal such as a human) suffering from pain.

The use of a compound of the invention as defined herein for the manufacture of a medicament for use in the reduction or elimination of pain in a patient (e.g. a mammal such as a human) suffering from pain.

The use of a compound of the invention as defined herein for the manufacture of a medicament for the treatment of any one or more of nociception, somatic pain, visceral pain, acute pain, chronic pain, hyperalgesia, allodynia, post-operative pain, pain due to hypersensitivity, headache, inflammatory pain (rheumatic, dental, dysmenorrhoea or infection), neurological pain, musculoskeletal pain, cancer related pain or vascular pain.

A compound of the invention as defined herein for use in treating any one or more of nociception, somatic pain, visceral pain, acute pain, chronic pain, hyperalgesia, allodynia, post-operative pain, pain due to hypersensitivity, headache, inflammatory pain (rheumatic, dental, dysmenorrhoea or infection), neurological pain, musculoskeletal pain, cancer related pain or vascular pain.

A method of treating pain in a patient such as a mammal (e.g. human), which method comprises administering to the patient a therapeutically effective amount of a compound of the invention as defined herein.

A method for the reduction or elimination of pain in a patient (e.g. a mammal such as a human) suffering from pain, which method comprises administering to the patient an effective pain-reducing or pain-eliminating amount of a compound of the invention as defined herein.

A method for the treatment of any one or more of nociception, somatic pain, visceral pain, acute pain, chronic pain, hyperalgesia, allodynia, post-operative pain, pain due to hypersensitivity, headache, inflammatory pain (rheumatic, dental, dysmenorrhoea or infection), neurological pain, musculoskeletal pain, cancer related pain or vascular pain, which method comprises administering to the patient a therapeutically effective amount of a compound of the invention as defined herein.

A compound of the invention as defined herein for use in the prophylaxis or treatment of stroke.

A method for the prophylaxis or treatment of stroke in a patient such as a mammal (e.g. human), which method comprises administering to the patient a therapeutically effective amount of a compound of the invention as defined herein.

A compound of the invention as defined herein for use as a neuroprotective agent.

A method of preventing or reducing neuronal damage in a patient suffering from stroke, which method comprises administering to the patient an effective neuroprotective amount of a compound of the invention as defined herein.

The use of a compound of the invention as defined herein for the manufacture of a medicament for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A compound of the invention as defined herein for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A method for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation, which method comprises administering to the patient an effective therapeutic amount of a compound of the invention as defined herein.

A compound of the invention as defined herein for use in the prophylaxis or treatment of a disease state or condition mediated by a cyclin dependent kinase 5.

The use of a compound of the invention as defined herein for the manufacture of a medicament for the prophylaxis or treatment of a disease state or condition mediated by a cyclin dependent kinase 5.

A method for the prophylaxis or treatment of a disease state or condition mediated by a cyclin dependent kinase 5, which method comprises administering to a subject in need thereof a compound of the invention as defined herein.

A method for alleviating or reducing the incidence of a disease state or condition mediated by a cyclin dependent kinase 5, which method comprises administering to a subject in need thereof a compound of the invention as defined herein.

The use of a compound of the invention as defined herein for the manufacture of a medicament for the prophylaxis or treatment of a disease state or condition mediated by cdk5 or p35.

The use of a compound of the invention as defined herein for the manufacture of a medicament for the prophylaxis or treatment of a disease state or condition mediated by cdk5 or p35, said disease state or condition being other than Alzheimer's disease, Huntington's disease or Creutzfeldt-Jakob disease.

The use of a compound of the invention as defined herein for the manufacture of a medicament for the prophylaxis or treatment of a disease state or condition mediated by cdk5 or p35, said disease state or condition being other than a neurodegenerative disease.

The use of a compound of the invention as defined herein for the manufacture of a medicament for the prophylaxis or treatment of a disease state or condition characterised by elevated levels of cdk5 or p35.

A compound of the invention as defined herein for use in the prophylaxis or treatment of a disease state or condition mediated by cdk5 or p35, said disease state or condition being other than Alzheimer's disease, Huntington's disease or Creutzfeldt-Jakob disease.

A compound of the invention as defined herein for use in the prophylaxis or treatment of a disease state or condition mediated by cdk5 or p35, said disease state or condition being other than a neurodegenerative disease.

A compound of the invention as defined herein for use in the prophylaxis or treatment of a disease state or condition characterised by elevated levels of cdk5 or p35.

A method of prophylaxis or treatment of a disease state or condition mediated by cdk5 or p35, said disease state or condition being other than Alzheimer's disease, Huntington's disease or Creutzfeldt-Jakob disease, which method comprises administering to a patient in need thereof a therapeutically effective amount of a compound of the invention as defined herein.

A method of prophylaxis or treatment of a disease state or condition mediated by cdk5 or p35, said disease state or condition being other than a neurodegenerative disease, which method comprises administering to a patient in need thereof a therapeutically effective amount of a compound of the invention as defined herein.

A method of prophylaxis or treatment of a disease state or condition characterised by elevated levels of cdk5 or p35, which method comprises administering to a patient in need thereof a therapeutically effective amount of a compound of the invention as defined herein.

A compound of the invention as defined herein for use in the prophylaxis or treatment of a neuropathy, such as a peripheral neuropathy, other than Alzheimer's disease, Huntington's disease or Creuzfeldt-Jakob disease.

The use of a compound of the invention as defined herein for the manufacture of a medicament for the prophylaxis or treatment of a neuropathy, such as a peripheral neuropathy, other than Alzheimer's disease, Huntington's disease or Creuzfeldt-Jacob disease.

A method of prophylaxis or treatment of a neuropathy, such as a peripheral neuropathy, other than Alzheimer's disease, Huntington's disease or Creuzfeldt-Jacob disease, which method comprises administering to a patient in need thereof a therapeutically effective amount of a compound of the invention as defined herein.

ANTI-FUNGAL, ANTI-PROTOZOAL, ANTI-VIRAL AND ANTI-PARASITIC ACTIVITY

Compounds of the present invention and their acid addition salts and crystalline forms thereof have antifungal activity, anti-protozoal activity and anti-parasitic activity.

In particular, compounds of the invention are useful in treating infection by pathogenic fungi, protozoa and parasites where infection by the pathogen is normally associated with an antibody response to HSP90.

In one embodiment, the invention provides compounds of the formula (1) and sub-groups thereof as defined herein for use as anti-fungal agents.

Examples of fungi include those that are pathogenic in man and other animals, for example:

*Candida* species such as *Candida albicans* and *Candida tropicalis;*

*Cryptococcus* species such as *Cryptococcus neobnrmans* and *Cryptoocccal meningitis;*

*Aspergillus* species such as *Aspergillus fumigatus, Aspergillus flavus* and *Aspergillus niger;*

*Microsporum* species such as *Microsporum canis* and *Microsporum gvpseunm;*

*Epidermophyton* species;

*Trichophyton* species such as *Trichophyton equinumn, Trichophyton mentagrophytes* and *Trichophyton rubrum;*

*Epidermophyton floccosum;*

*Exophiala werneckii;*

*Fusarium* species such as *Fusarium solani;*

*Sporothrix schenckii;*

*Penicillium* species such as *Penicillium rubrunm;*

*Alternaria* species;

*Ceratocystis pilifera;*

*Chrysosporiumn pruinosum;*

*Helminthsporium* species;

*Paecilomyces variotti;* yeasts, for example *Saccharomyces cerevisiae* and *Pityrosporum* species such as *Pityrosporum orbiculare* and *Pityrosporum ovale;*

*Histoplasma* species such as *Histoplasma capsulatum;*

*Coccidiodes* species;

*Paracoccidioides* species; and

*Blastomyces* species.

In another embodiment, the invention provides compounds of the formula (1) and sub-groups thereof as defined herein for use as anti-protozoal agents.

Examples of protozoa include:

*Tirpanosoma cruzi;*

*Leishmania* species; for example the *L. donovani* complex (*L. donovani, L. infantum,* and *L. chagasi*); the *L. mexicana* complex (3 main species—*L. mexicana, L. amazonensis,* and *L. venezuelensis*); *L. tropica; L. major; L. aethiopica;* and the subgenus *Viannia* with four main species (*L. (V.) braziliensis, L. (V.) guyanensis, L. (V.) panamensis,* and *L. (V.) peruviana*);

*Toxoplasma gondii;* and

*Trichomonas vaginalis.*

In a further embodiment, the invention provides compounds of the formula (1) and sub-groups thereof as defined herein for use as anti-parasitic agents.

Examples of parasites include parasitic worms such as:

parasitic roundworms such as *Ascaris lumbricoides;* parasitic flatworms such as the parasitic trematode worms, e.g. *Schistosoma mansoni*

The invention also provides inter alia:

A compound of the invention as defined herein for use in the prophylaxis or treatment of a fungal, protozoal or parasitic disease state or condition (other than a disease state or condition due to *Plasmodium falciparum*), for example a disease state or condition characterised by an antibody response to Hsp90.

The use of a compound of the invention as defined herein for the manufacture of a medicament for the prophylaxis or treatment of a fungal, protozoal or parasitic disease state or condition (other than a disease state or condition due to *Plasmodium falciparum*), for example a disease state or condition characterised by an antibody response to Hsp90.

A method for the prophylaxis or treatment of a fungal, protozoal or parasitic disease state or condition (other than a disease state or condition due to *Plasmodium falciparum*), for example a disease state or condition characterised by an antibody response to Hsp90, which method comprises administering to a subject in need thereof a compound of the invention as defined herein.

A compound of the invention as defined herein for use in the prophylaxis or treatment of a fungal disease state or condition, for example a disease state or condition characterised by an antibody response to Hsp90.

The use of a compound of the invention as defined herein for the manufacture of a medicament for the prophylaxis or treatment of a fungal disease state or condition, for example a disease state or condition characterised by an antibody response to Hsp90.

A method for the prophylaxis or treatment of a fungal disease state or condition, for example a disease state or condition characterised by an antibody response to Hsp90, which method comprises administering to a subject in need thereof a compound of the invention as defined herein.

A compound of the invention as defined herein for use in preventing, arresting or reversing the infection of an animal (such as a mammal, e.g. a human) by pathogenic fungi.

The use of a compound of the invention as defined herein for the manufacture of a medicament for preventing, arresting or reversing the infection of an animal (such as a mammal, e.g. a human) by pathogenic fungi.

A method for preventing, arresting or reversing the infection of an animal (such as a mammal, e.g. a human) by pathogenic fungi, which method comprises administering to a subject in need thereof a compound of the invention as defined herein.

A compound of the invention as defined herein for any of the uses and methods set forth above, and as described elsewhere herein.

The use of a compound of the invention as defined herein for the manufacture of a medicament for the prophylaxis or treatment of any of the disease states or conditions described herein.

A combination of a compound of the invention as defined herein with an ancillary compound which is an anti-fungal agent (e.g. an azole antifungal agent).

A pharmaceutical composition comprising a compound of the invention as defined herein with an ancillary compound which is an antifungal agent (e.g. an azole antifungal agent).

A compound of the invention as defined herein for use in preventing, reducing or reversing the development of resistance to an anti-fungal agent, anti-protozoal agent or anti-parasitic agent (preferably an anti-fungal agent) coadministered therewith.

The use of a compound of the invention as defined herein for the manufacture of a medicament for coadministration with an anti-fungal agent, anti-protozoal agent or anti-parasitic agent (preferably an anti-fungal agent) to prevent, reduce or reverse the development of resistance to the anti-fungal agent, anti-protozoal agent or anti-parasitic agent.

A method of preventing or reducing development of resistance to an anti-fungal agent in a patient (e.g. a human patient), which method comprises administering to the patient a combination of an anti-fungal agent, anti-protozoal agent or anti-parasitic agent (preferably an anti-fungal agent) and a compound of the invention as defined herein.

A method for the prophylaxis or treatment (or alleviation or reduction of the incidence) of a disease state or condition mediated by Hsp90, which method comprises administering to a subject in need thereof a combination of a compound of the invention as defined herein with an anti-fungal, anti-protozoal or anti-parasitic drug, wherein the disease state or condition mediated by Hsp90 is the development of resistance to the anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoal or anti-parasitic drug; (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject in need thereof a combination of a compound of the invention as defined herein with the said anti-fungal, anti-protozoal or anti-parasitic drug.

A method for the treatment of a fungal, protozoal or parasitic disease or condition, which method comprises administering to a subject in need thereof a combination of compound of the invention as defined herein with an anti-fungal, anti-protozoal or anti-parasitic drug, which method is characterized by the absence of drug resistance.

A method for the prophylaxis or treatment (or alleviation or reduction of the incidence) of a disease state or condition mediated by Hsp90 in a subject undergoing treatment with an anti-fungal, anti-protozoal or anti-parasitic drug, which method comprises administering to the subject a compound of the invention as defined herein, wherein the disease state or condition mediated by Hsp90 is the development of resistance to said anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoal or anti-parasitic drug (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject undergoing treatment with said ancillary compound a compound of the invention as defined herein.

A method for the treatment of a fungal, protozoal or parasitic disease in a subject undergoing treatment with an anti-fungal, anti-protozoal or anti-parasitic drug, which method comprises administering to a subject in need thereof a compound of the invention as defined herein, which method is characterized by the absence of drug resistance e.g. to said anti-fungal, anti-protozoal or anti-parasitic drug).

As described above in the introductory part of this application, compounds having Hsp90 inhibitory activity have been found to exhibit potent anti-fungal activity and prevent the development of resistance to anti-fungals and in particular Hsp90 dependent resistance to anti-fungals. Moreover, it has been found that inhibition of Hsp90 activity can reduce the development of resistance to commonly used anti-fungal drugs such as the azoles. The compounds of the invention will therefore be useful in the prophylaxis or treatment of a range of fungal diseases and conditions and will also be useful, when coadministered with other anti-fungal drugs such as the azoles, in enhancing the activity of the anti-fungal drugs.

The antifungal activity of the compounds of the present invention may be evaluated by determining the minimum fungistatic (inhibition) concentration (m.i.c.). This test is usually performed by preparing a series of plates or tubes containing a suitable nutrient medium, each plate or tube also containing a different concentration of the test compound and then inoculating the medium with the fungal species. After an incubation period the plates are examined visually for the presence or absence of fungal growth. The m.i.c. is the minimum concentration required to prevent fungal growth.

The compounds may be used in animal medicine (for example in the treatment of mammals such as humans).

Fungal infections in animals against which compound of the invention as defined herein may be used include:

Superficial mycoses—i.e. fungal infections limited to the outermost layers of the skin and hair;

Cutaneous mycoses—i.e. fungal infections that extend deeper into the epidermis but are typically restricted to the keratinized layers of the skin, hair, and nails;

Subcutaneous mycoses—i.e. fungal infections involving the dermis, subcutaneous tissues, muscle, and fascia;

Systemic mycoses due to primary pathogens (these typically originate primarily in the lungs and may spread to other organ systems); and Systemic mycoses due to opportunistic pathogens (infections of patients with immune deficiencies who would otherwise not be infected).

Particular examples of fungal disease states for which compounds of the invention as defined herein may be used include:

Dermatophyte infections such as tinea versiColour (a superficial fungal infection of the skin), tinea pedis (Athletes' Foot), tinea capitis (superficial fungal infection on the head), tinea barbae (fungal infection of bearded areas), tinea corporis (fungal infection of smooth skin areas).

Mucosal Candidiasis such as Oral Candidiasis, esophagitis and Vaginal candidiasis.

Invasive or deep organ candidiasis (e.g., fungemia, endocarditis, and endophthalmitis).

Crytpococcal infections such as Cryptococcal meningitis.

Histoplasmosis.

Blastomycosis, a fungal infection of the lungs and occasionally the skin.

Invasive Fungal Infections in patients with weakened immune systems or under treatment with anti-cancer or anti-AID drugs, for example Invasive Candidiasis and Invasive Aspergillosis.

Aspergilloses such as Allergic Bronchopulmonary Aspergillosis.

Aspergilloma.

Intertrigo infections (fungal infections occurring in folds of skin e.g. between the toes or fingers, in the underarm area, or in the groin area).

Maduramycosis (fungal invasion of the tissue of the foot, also known as madura foot).

Coccidioidomycosis.

Mucormycosis.

Blastomycosis

Geotrichosis.

Chromoblastomycosis.

Conidiosporosis.

Histoplasmosis.

Rhinosporidosis.

Nocaidiosis.

Para-actinomycosis.

Penicilliosis.

Monoliasis.

Sporotrichosis.

Fungal infections of particular interest are Candidiasis and Aspergillosis.

Compounds of the invention also have anti-protozoal activity and anti-parasitic activity. The antiprotozoal activity of the compounds of the present invention may be assessed by conventional methods, for example by determining the minimum inhibition concentration (m.i.c.) or 50% inhibition level ($IC_{50}$).

Examples of protozoal and parasitic diseases or conditions for which compounds of the invention may prove useful include:

Chagas disease ((trypanosomiasis)—an infection caused by the parasite *Trypanosonma cruzi*.

*Ascariasis*—a human disease caused by the parasitic roundworm *Ascaris lumbricoides*.

Leishmaniasis—a disease caused by parasites of the genus *Leishmania*.

Toxoplasmosis—a parasitic disease caused by the protozoan *Toxoplasma gondii*.

Schistosomiasis (Bilharzia)—a disease caused by the parasite Schistoma mansoni.

Trichomoniasis—a sexually transmitted disease caused by the parasitic protozoan *Trichomonas vaginalis*.

ANTI-VIRAL ACTIVITY

As discussed above in the introductory sections of this application, infection of a host cell with viral RNA/DNA results in a substantial redirection of cellular protein synthesis towards key viral proteins encoded by the viral nucleic acid, and this frequently gives rise to upregulation of heat shock proteins. It is believed that one function of the HSP induction may be to assist in the stabilization and folding of the high levels of 'foreign' protein generated in preparation for virus replication and it has been shown (Nagkagawa et al.) that HSP 90 inhibitors can block viral replication. Accordingly, the compounds of the invention are useful in combatting viral infections, for example by blocking or inhibiting viral replication.

Therefore, in another aspect, the invention provides a compound of the invention as defined herein for use in the prophylaxis or treatment of a viral infection (or viral disease).

In further aspects, the invention provides:

The use of a compound of the invention as defined herein for the manufacture of a medicament for the prophylaxis or treatment of a viral infection (or viral disease).

A method for the prophylaxis or treatment of a viral infection (or viral disease), which method comprises administering to a subject in need thereof a compound of the invention as defined herein.

A compound of the invention as defined herein for use in blocking or inhibiting viral replication in a host organism (e.g. an animal such as a mammal (e.g. human)).

The use of a compound of the invention as defined herein for the manufacture of a medicament for use in blocking or inhibiting viral replication in a host organism (e.g. an animal such as a mammal (e.g. human)).

A method of blocking or inhibiting viral replication in a host organism (e.g. an animal such as a mammal (e.g. human)), which method comprises administering to the host organism a compound of the invention as defined herein.

Examples of viral infections that may be treated with the compounds of the invention include infections due to any one or more of the following viruses:

Picornaviruses such as rhinoviruses (common cold virus), Coxsackie virus (e.g. Coxsackie B virus); and foot and mouth disease virus;

Hepatitis viruses such as hepatitis A virus (HAV), hepatitis B virus (HBV), hepatitis C virus (HCV), hepatitis D virus (HDV) and hepatitis E virus (HEV), Coronaviruses (e.g. common cold virus and Severe acute respiratory syndrome (SARS) virus)

Adenoviruses such as Human Adenoviruses (a cause of respiratory and conjunctival infections);

Astroviruses (a cause of flu-like symptoms);

Flaviviruses such as the Yellow Fever virus;

Orthomyxoviruses such as influenza viruses (e.g. influenza A, B and C viruses);

Parainfluenza viruses;

Respiratory syncytial virus;

Enteroviruses such as Poliovirus (Poliomyelitis virus);

Paramyxoviruses such as the Measles (rubeola) virus, mumps virus, respiratory syncytial virus (RSV) and canine distemper virus (CDV);

Togaviruses such as the Rubella (German Measles) virus and Sindbis virus;

Herpes viruses such as:

Herpes simplex virus (HSV), for example HSV-1 which causes fever blisters (cold sores), gingivostomatitis, herpes keratitis, eczema herpeticum and HSV encephalitis); and HSV-2 which causes genital lesions, neonatal infections, HSV meningitis, HSV proctitis;

Varicella zoster virus (VZV), which causes chickenpox, congenital varicella syndrome and shingles;

Epstein-Barr Virus (EBV), which causes infectious mononucleosis, Burkitt's lymphoma and nasopharyngeal cancer Cytomegalovirus (CMV), e.g. human cytomegalovirus (HCMV);

Human herpes virus 6 (HHV-6), which causes exanthum subitum or roseola infantum

Human herpes virus 8 (HHV-8) or Kaposi's sarcoma-associated herpes virus (KSHV), which is found in the saliva of many AIDS patients and associated with Kaposi's sarcoma;

Papovaviridae such as polyoma virus and human papilloma virus (HPV);

Parvoviruses;

Poxviruses such as Variola virus (human smallpox virus);

Rhabdoviruses such as rabies virus and vesicular stomatitis virus (VSV); and

Retroviruses such as Human immunodeficiency virus (HIV) which is responsible for acquired immune deficiency syndrome (AIDS); and Human T-lymphotrophic virus (HTLV).

Particular viral infections against which the compounds of the invention may be used include herpes virus, pox virus, Epstein-Barr virus, Sindbis virus, adenovirus, HIV (for prevention of AIDS development in HIV-infected individuals), HPV, HCV and HCMV viruses.

The viral infection may be other than an infection with hepatitis C virus (HCV).

The activity of the compounds of the invention as agents for blocking or preventing viral replication in host organisms or host cells can be determined in accordance with standard procedures well known to the skilled person.

The compounds of the invention may be used as the sole antiviral agent or they may be used in conjunction with other anti-viral agents such as acyclovir, ganciclovir, oseltamivir (Tamiflu®) and zanamavir (Relenza®), amantidine, rimantadine, adefovir dipivoxil, interferons (e.g. interferon alfa-2b and pegylated interferon alfa-2a), lamivudine, entecavir, ribavirin, famciclovir, valcicylovir, valacyclovir, azidothymidine (AZT—Retrovir®), atazanavir, fosamprenavir, lamivudine, lamivudine+abacavir, tenofovir disoproxil fumarate, tenofovir disoproxil fumarate+emtricitabine, tipranavir, nelfinavir, indinavir, raltegravir, ritonavir, lopinavir+ritonavir, darunavir, amprenavir, enfuvirtide, saquinavir, hydroxyurea, VGV-1 and anti-viral vaccines.

Accordingly, the invention further provides:

A combination of a compound of the invention as defined herein with an ancillary compound which is an antiviral agent.

A pharmaceutical composition comprising a compound of the invention as defined herein with an ancillary compound which is an antiviral agent.

PHARMACEUTICAL FORMULATIONS

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy.

Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compound of the invention as defined herein and in particular compounds of the formulae (10) and (1) and crystalline and salt forms thereof as defined herein in the form of pharmaceutical compositions.

The pharmaceutical compositions can be in any form suitable for oral, parenteral, topical, intranasal, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of the invention or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (1) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound. Thus, unit-dose suppositories or pessaries may be prepared by admixture of the active ingredient with one or more conventional solid carriers, for example coca butter, and shaping the resulting mixture. Further examples of mouldable waxy materials include polymers such as high molecular weight polyalkylene glycols, e.g. high molecular weight polyethylene glycols.

Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Further examples of topical compositions include dressings such as bandages and adhesive plasters impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

METHODS OF TREATMENT

The compounds of the invention will be useful in the prophylaxis or treatment of a range of disease states or conditions mediated by Hsp90 client proteins. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (1) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required.

The compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined.

Examples of other therapeutic agents or treatments that may be administered together (whether concurrently or at different time intervals) with the compounds of the invention include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies, e.g. HDAC or HAT modulators
Radiotherapy; and
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid itself and agents such as megestrol acetate which can be used for the treatment of side-effects including oedema and thromboembolic episodes.

For the case of Hsp90 inhibitors combined with other therapies, the two or more treatments may be given in individually varying dose schedules and via different routes.

Where the compound is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

METHODS OF DIAGNOSIS

Prior to administration of a compound, a patient may be screened to determine whether a disease or condition from which the patient is or may be suffering is one which would be susceptible to treatment with a compound having activity against Hsp90.

For example, a biological sample taken from a patient may be analysed to determine whether a condition or disease, such as cancer, that the patient is or may be suffering from is one which is characterised by a genetic abnormality or abnormal protein expression which leads to the mutation or over-activation of an Hsp90 client protein. Examples of such abnormalities that result in activation of Hsp90 client proteins include; Bcr-ABL translocation, Flt-3 internal duplication, and mutation of Braf, or over-expression of ErbB2.

Thus, the patient may be subjected to a diagnostic test to detect a marker characteristic of up-regulation. The term diagnosis includes screening. By marker we include genetic markers including, for example, the measurement of DNA composition to identify mutations of Braf, BCR-abl, and Flt3 or other affected client proteins. The term marker also includes proteins such as ErbB2, including levels or concentrations of the protein or some fragments or degradation product and for enzymes the enzymic activity. The protein (e.g. phosphorylated or not) and mRNA levels of the aforementioned proteins could also be assessed to characterise a change in activity. For example the level of phosphorylated AKT can be an indicator of sensitivity to HSP90 inhibitors The diagnostic tests are typically conducted on a biological sample selected from for example tumour biopsy samples, blood samples (isolation and enrichment of shed tumour cells), stool biopsies, sputum, chromosome analysis, pleural fluid, peritoneal fluid, buccal spears or biopsy or from urine.

The screening process will typically involve direct sequencing, oligonucleotide or protein microarray analysis, proteomic analysis by mass spectrometry, immunohistochemical techniques or detection using a specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR), in-situ hybridisation or immunoblotting.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Commercially available FISH probes also exist for cytogenetic detection of chromosome rearrangements, which can be used to detect Flt3 and Bcr-Abl translocations within leukeamia cell populations. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al., BMC Cancer 2003, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of the "philadelphia chromosome" indicative of BCR-ABL translocation.

Therefore, all of these techniques could also be used to identify tumours particularly suitable for treatment with the compounds of the invention.

EXAMPLES

The invention will now be illustrated, but not limited, by reference to the specific embodiments described in the following examples.

In the examples, the following abbreviations may be used.
AcOH acetic acid
BOC tert-butyloxycarbonyl
Bn benzyl
CDI 1,1-carbonyldiimidazole
DMAW90 Solvent mixture: DCM: MeOH, AcOH, $H_2O$ (90:18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
Et3N triethylamine
EtOAc ethyl acetate
Et2O diethyl ether
h hour(s)
HOAt 1-hydroxyazabenzotriazole
HOBt 1-hydroxybenzotriazole
MeCN acetonitrile
MeOH methanol
min. minutes
Ms mesyl
MsO mesylate
P.E. petroleum ether
PG protecting group
r.t. room temperature
SiO2 silica
TBTU N,N,N',N'-tetramethyl-O-(benzotriazol-1-yl)uronium tetrafluoroborate
THF tetrahydrofuran Proton magnetic resonance ($^1$H NMR) spectra were recorded on a Bruker AV400 instrument operating at 400.13 MHz, in DMSO-$d_6$ or MeOH-$d_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

In the examples, the compounds prepared were characterised by liquid chromatography and mass spectroscopy using the system and operating conditions set out below. Where atoms with different isotopes are present and a single mass quoted, the mass quoted for the compound is the monoisotopic mass (i.e. 35Cl; 79Br etc.). Different systems were used, as described below, and these were equipped with, and were set up to run under, closely similar operating conditions. The operating conditions used are also described below.

System Description:
System 1 (Analytical System):
HPLC System: Waters 2795
Mass Spec Detector: Micromass Platform LC
PDA Detector: Waters 2996 PDA
System 2 (Preparative and Analytical System):
HPLC System: Waters Fractionlynx system
Mass Spec Detector: Waters ZQ
PDA Detector: Waters 2996 PDA
System 3 (Preparative and Analytical System):
HPLC System: Agilent 1100 system
Mass Spec Detector: LCIMSD
UV Detector: Agilent MWD
Operating Conditions:
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes (over 15 minutes w/column 2)
Flow: 0.8 ml/min
Column 1: Phenomenex Synergi 4µ MAX-RP 80A, 2.0×50 mm
Column 2: Phenomenex Synergi 4µ MAX-RP 80A, 2.0×150 mm
Basic Analytical Conditions:
Eluent A: $H_2O$ (10 mM $NH_4HCO_3$ buffer adjusted to pH=9.2 with $NH_4OH$)
Eluent B: $CH_3CN$
Gradient: 5-95% eluent B over 3.5 minutes
Flow: 0.8 ml/min
Column: Phenomenex Gemini 5µ 2.0×50 mm
MS Conditions (Waters Systems):
Capillary voltage: 3.6 kV (3.40 kV on ES negative)
Cone voltage: 25 V
Source Temperature: 120° C.
Scan Range: 125-800 amu
Ionisation Mode: ElectroSpray Positive, Negative or Positive & Negative
MS Conditions (Agilent Systems):
Capillary voltage: 4000 V (3500 V on ES Negative)
Fragmentor/Gain: 150/1
Drying gas Temp/flow: 350° C./13.0 Lmin$^{-1}$
Nebuliser pressure: 50 psig
Scan Range: 125-800 amu
Ionisation Mode: ElectroSpray Positive or Negative The starting materials for each of the Examples are commercially available unless otherwise specified.

Example 1

Step 1

4-Acetoxy-2-hydroxy-benzoic acid methyl ester

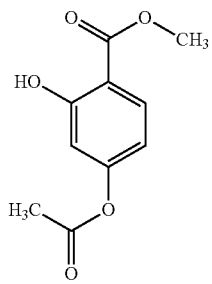

Resorcinol methyl ester (50 g, 0.298 mol) and N,N-dimethyl-4-aminopyridine (0.27 g, 0.0022 mol, 0.74 mol %) were added to toluene 0.2 L followed by acetic anhydride (30 mL, 0.318 mol). The solution was heated to 50° C. for 2 h. The solvent was removed by evaporation at 50° C. to a small volume and the residue was azeotroped once with toluene. To the residual oil was immediately added toluene (100 mL) whilst still warm and the solution used for Step 2 without further purification.

Step 2

5-Acetyl-2,4-dihydroxy-benzoic acid methyl ester

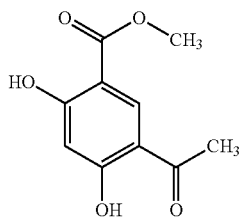

The toluene solution from Step 1 was cooled in an ice bath under $N_2$ and triflic acid (26 mL) added slowly over 30 min. On stirring a fine white solid was formed which dissolved on stirring for 16 h at RT to give a yellow solution. To the solution was added acetyl chloride (2 mL) and the solution stirred at RT for a further 1 h. This solution was cannulated into a stirred cooled (0° C.) solution of EtOAc (600 mL) and NaOAc.3H$_2$O (40 g) dissolved in water (400 mL). The organic phase was washed with water (twice, 200 mL), saturated brine and was evaporated to a small volume without drying. The residue was azeotroped with heptane (twice, 100 mL) and heptane (100 mL) was added and the crystalline solid removed by filtration, washed well on sinter with heptane and dried to give 49.5 g (79%).

Final Purification of Combined Batches

The combined batches of solid (96.3 g) was heated to boiling with 10% IPA/heptane (250 mL) then cooled to RT and finally to 0° C., filtered and the residue dried 72 h (oil pump) to give (88.04 g, 91.5%), pure by hplc, tlc and NMR. $^1$H NMR (DMSO-d$_6$) 12.58 (1H, s), 11.22 (1H, s), 8.33 (1H, s), 6.45 (1H, s), 3.90 (3H, s), 2.62 (3H, s).

Step 3

5-Acetyl-2,4-dihydroxy-benzoic acid methyl ester (Alternative procedure)

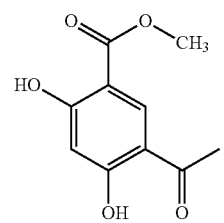

Resorcinol methyl ester (50 g, 0.298 mol) and Amberlyst 15 resin (40 g) were suspended in toluene 150 mL (under a nitrogen atmosphere) and the solution was heated in an oil bath at 70° C. (internal temp 56° C.). Acetyl chloride (22 mL, 308 mmol) was added in 5 mL portions over 30 mins giving evolution of gaseous HCl (which was scrubbed by passing the nitrogen stream through aqueous NaOH). The solution was stirred at 70° C. for 4.5 h then heated in an oil bath temp (internal temperature 96° C.) for 3.5 h. The solution was cooled to 50° C. and EtOAc (100 mL) was added and the solution filtered whilst at this temperature. The residual resin was washed with EtOAc (50 mL) and the combined filtrates were concentrated to slurry of crystalline solid (total weight of 128 g for solid plus solvent). To the slurry was added heptane (100 mL) and after 10 mins at RT the solid was removed by filtration. The residue was washed with heptane:toluene (2:1, 60 mL) then with petroleum ether bp 40-60° C. and dried in vacuo to give crop 1 29 g (46.4%) (NMR showed 3% of material resulting from saponification of the methyl ester).

The filtrate was evaporated to a small volume and 20% EtOAc in heptane (100 mL) was added. After standing at RT 16 h a second crop of 4.75 g (7.6%) was obtained (NMR identical to crop 1).

Step 4

5-Acetyl-2,4-bis-benzyloxy-benzoic acid methyl ester

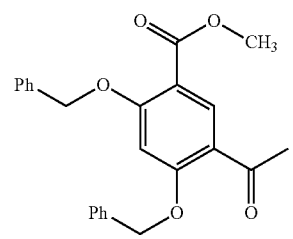

Benzyl bromide (70 ml, 0.59 mol) was added to a stirred mixture of methyl 5-acetyl-2,4-dihydroxybenzoate (60.7 g, 0.29 mol) and anhydrous potassium carbonate (87.8 g, 0.64 mol) in acetonitrile (800 ml) and the mixture was stirred and held at reflux for 16 hours. Upon cooling to room temperature the mixture was poured onto water (3 L) and stirred vigorously for 2 hours. The solids were collected by filtration, rinsed with water (2 L), sucked dry under reduced pressure and dried to constant mass in a vacuum oven at 60° C. overnight to afford methyl 5-acetyl-2,4-bis-benzyloxy-benzoate (112.1 g. 99%) as a cream solid. $^1$H NMR (DMSO-$d_6$) 8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]$^+$ 391.

Step 5

2,4-Bis-benzyloxy-5-isopropenyl-benzoic acid methyl ester

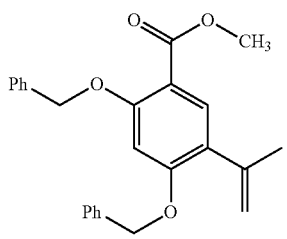 [SMILES: C=C(C)c1cc(C(=O)OC)c(OCc2ccccc2)cc1OCc1ccccc1]

Potassium tert-butoxide (29.1 g, 0.26 mol) was added to a stirred suspension of methyltriphenylphosphonium bromide (92.8 g, 0.26 mol) in anhydrous tetrahydrofuran (1 L) and the mixture was stirred at room temperature for 10 minutes whereupon methyl 5-acetyl-2,4-bis-benzyloxybenzoate (78.0 g, 0.2 mol) was added and the mixture stirred at room temperature for a further 30 minutes. Methanol (100 ml) was added to quench excess phosphorus ylide and the solvent was removed in vacuo to afford an orange oil that crystallized on standing. The residue was recrystallized from methanol (330 ml). The solids were collected by suction filtration, washed with methanol (50 ml) and sucked dry under reduced pressure to afford methyl 2,4-bis-benzyloxy-5-isopropenyl-benzoate as pale yellow needles. The mother liquor deposited a second crop of material upon standing overnight (combined yield: 56.55 g, 73%) $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]$^+$ 389.

A further crop of the ester could be obtained as follows. The crystallization residues were evaporated to dryness in vacuo and the oily solid was treated with 5% ethyl acetate in heptane (250 ml). Ethyl acetate was added in small portions to the vigorously stirred mixture until the residue deposited a large quantity of solid triphenylphosphine oxide. The solids were removed by filtration and the filtrate evaporated to dryness in vacuo to afford an orange oil. Recrystallization from methanol (as described above) afforded further methyl 2,4-bis-benzyloxy-5-isopropenyl-benzoate as a pale yellow crystalline solid (total yield 85-90%).

Step 6

2,4-Bis-benzyloxy-5-isopropenyl-benzoic acid

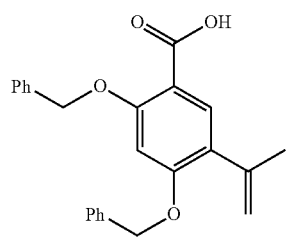 [SMILES: C=C(C)c1cc(C(=O)O)c(OCc2ccccc2)cc1OCc1ccccc1]

Potassium hydroxide (10.96 g, 0.19 mmol) was added to a stirred suspension of methyl 2,4-bis-benzyloxy-5-isopropenyl-benzoate (61.0 g, 0.16 mol) in methanol (750 ml) and water (250 ml) and the mixture was stirred and held at reflux for 16 hours. Upon cooling the organic solvent was removed in vacuo and the mixture acidified to pH 2 or below by the addition of 2M hydrochloric acid (200 ml). The mixture was diluted with water (2 L) and extracted with ethyl acetate (2 L), the organic layer was separated and the solvent removed in vacuo to afford 2,4-bis-benzyloxy-5-isopropenyl-benzoic acid (58.8 g, 100%) as a colourless solid. $^1$H NMR (DMSO-$d_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]$^+$ 375.

Step 7

Di-prop-2-ynyl-carbamic acid benzyl ester

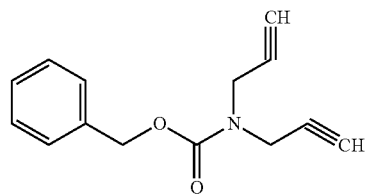 [SMILES: C#CCN(CC#C)C(=O)OCc1ccccc1]

To a cooled (0° C.) solution of dipropargylamine (46.7 g, 502 mmol) in EtOAc (200 mL) and 10% aqueous $K_2CO_3$ (700 mL, 507 mmol) was slowly added a solution of N-(benzyloxycarbonyloxy)succinimide (125 g, 502 mmol) in EtOAc (500 mL) over 20 mins. The solution was stirred at 0° C. for 2 h then at RT 16 h. The phases were separated and the organic phase was washed with 10% aqueous $K_2CO_3$ (700 mL, 507 mmol) and then with saturated brine (500 mL) and was diluted to 1000 mL with EtOAc to give a 0.5M solution.

Step 8

5-Hydroxymethyl-1,3-dihydro-isoindole-2-carboxylic acid benzyl ester

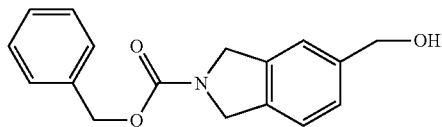 [SMILES: O=C(OCc1ccccc1)N1Cc2ccc(CO)cc2C1]

A solution of propargyl alcohol (26.4 mL, 424 mmol) in toluene (120 mL) was degassed. The 0.5M-diyne solution above (440 mL, 220 mmol) was evaporated and the residue dissolved in toluene (80 mL). This protected diyne solution and Wilkinson's catalyst (2.26 g, 2.44 mmol, 1.11% were added in 14 equal portions over a 2 h period with constant monitoring of the internal temperature such that the temperature remained 50-100° C. The solution was allowed to cool to 50° C. over 30 min when the solution was evaporated (to remove excess propargyl alcohol). The residue was heated with toluene (500 mL) and charcoal (Darco 4-12 mesh, 20 g) at 100° C. for 30 min and then filtered hot through a bed of Celite and the brown solution was evaporated. The residue was dissolve in EtOAc (400 mL) at 80° C. when silica gel (chromatography grade 65 g) was added and heating continued for 20 mins. The solution was filtered whilst hot and then evaporated (with seeding) to give a pale brown solid. 10% EtOAc/heptane (v/v, 100 mL) was added and the solid removed by filtration. The solid was washed on the sinter with heptane (100 mL) and the dried (50° C., oil pump, 16 h) to give the title compound 59.0 g (95%). $^1$H NMR (400 MHz, Me-d$_3$-OD): 7.51-7.16 (m, 8H), 5.21 (s, 2H), 4.74 (s, 2H), 4.70 (s, 2H), 4.61 (s, 2H).

Step 9

5-Methanesulfonyloxymethyl-1,3-dihydro-isoindole-2-carboxylic acid benzyl ester

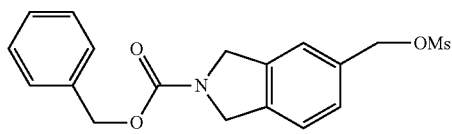 [SMILES: CS(=O)(=O)OCc1ccc2c(c1)CN(C(=O)OCc1ccccc1)C2]

To a solution of 5-hydroxymethyl-1,3-dihydro-isoindole-2-carboxylic acid benzyl ester (65.75 g, 0.232 mol) in THF (470 mL) and EtOAc (770 mL) was added Et-3N (39 mL, 0.28 mol). The solution was cooled in an ice-bath and a solution of methanesulphonyl chloride (19 mL, 0.245 mol) dissolved in EtOAc (50 mL) was added (so that the internal temp <12° C.). After stirring for 2 h in the ice-bath further additions of methanesulphonyl chloride (1.9 mL and 0.95 mL) and Et3N (3.9 mL) were made (so that by tlc there was no remaining starting material after a further 1 h of stirring). NaHCO$_3$ (550 mL) was added and the solution stirred for 20 mins then saturated brine (200 mL) was added and the phases were separated. The organic phase was dried (MgSO$_4$) and evaporated with seeding to give a damp solid which was used in the next step without thorough drying.

Step 10

5-(4-Methyl-piperazin-1-ylmethyl)-1,3-dihydro-isoindole-2-carboxylic acid benzyl ester dihydrochloride salt

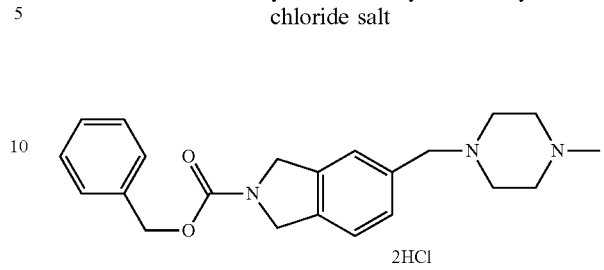

The solid from Step 9 (assume 0.232 mol) was dissolved in acetone (700 mL) and this solution was added over 45 mins to a cooled (internal temp 15-17° C.) suspension of K$_2$CO$_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried (MgSO$_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. $^1$H NMR (400 MHz, Me-d$_3$-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Alternative Step 10A 5-(4-Methyl-piperazin-1-ylmethyl)-1,3-dihydro-isoindole-2-carboxylic acid benzyl ester dihydrochloride

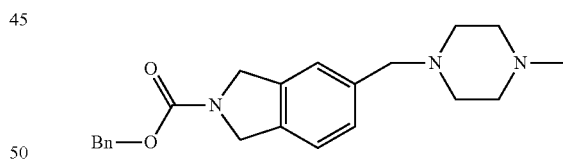

Step 10A can be Used as an Alternative Route to Replace Steps 9 and 10 Above.

To a suspension of manganese dioxide (15.5 g, 178 mmol) in DCM (100 mL) was added 5-hydroxymethyl-1,3-dihydro-isoindole-2-carboxylic acid benzyl ester (3.35 g, 11.8 mmol) and after 6 h stirring at RT a further addition of manganese dioxide (5 g, 57 mmol) was made. After a further 1 h stirring at RT Celite (7 g) was added and the solution was filtered through a bed of Celite™ giving a clear pale yellow solution. The Celite™ was washed with DCM and the volume of the combined organic solution adjusted to 100 mL by evaporation. N-Methylpiperazine (1.31 mL, 11.8 mmol) and acetic acid (0.68 mL) were added followed by sodium triacetoxyborohydride (4.98 g. 23.5 mmol). The yellow solution was stirred 16 h giving a colourless solution. To the solution was added 2M-HCl (10 mL, 20 mmol) giving an effervescence. After 30 min water (10 mL) and K$_2$CO$_3$ (5.5 g, 39.8 mmol) were added and the organic phase was dried (Na$_2$SO$_4$). After filtration 4M-HCl in dioxan (6 mL) was added with stirring and the suspension was evaporated to dryness. The residue was dissolved in MeOH with warming and after evaporation the solid was washed on a sinter with EtOAc then petrol (bp 40-60° C.) followed by drying in vacuo at 50° C. to give the title compound 3.61 g (70%). $^1$H NMR (400 MHz, Me-d$_3$-OD): 7.65-7.51 (2H, m), 7.51-7.27 (6H, m), 5.23 (2H, s), 4.83-4.69 (4H, m), 4.49 (2H, s), 3.66 (8H, d), 3.03 (3H, s)

Step 11

5-(4-Methyl-piperazin-1-ylmethyl)-2,3-dihydro-1H-isoindole

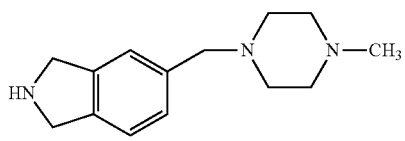 [SMILES: CN1CCN(Cc2ccc3c(c2)CNC3)CC1]

To 5-(4-Methyl-piperazin-1-ylmethyl)-1,3-dihydro-isoindole-2-carboxylic acid benzyl ester dihydrochloride salt (Step 10, 59.8 g, 136.7 mmol) was added EtOAc (400 mL) and 10% aqueous K$_2$CO$_3$ (400 mL). The organic phase was washed with saturated brine (200 mL) and then dried (MgSO$_4$). The solution was filtered and was evaporated to an oil (which crystallised on standing with petroleum ether (bp 40-60° C.)). The solid was dried in vacuo to give a colourless solid: 48.8 g (133.5 mmol).

A portion of the solid (24.4 g, 66.8 mmol) was dissolved in MeOH (170 mL) and after degassing the solution and purging with nitrogen 10% Pd/C (1.22 g) was added and the mixture hydrogenated at 1 atmosphere for 2.5 h. The solution was filtered and the solution evaporated and the residue was azeotroped twice with toluene at 30-40° C. The residue was dissolved in DMF (92 mL) and the solution was immediately degassed and purged with N$_2$.

(NB The product at this stage is sensitive to air and darkens on contact with oxygen. The DMF solution was used immediately but can be stored by degassing and storing under an atmosphere of N$_2$)

Step 12

(2,4-Bis-benzyloxy-5-isopropenyl-phenyl)-[5-(4-methyl-piperazin-1-ylmethyl)-1,3-dihydro-isoindol-2-yl]-methanone

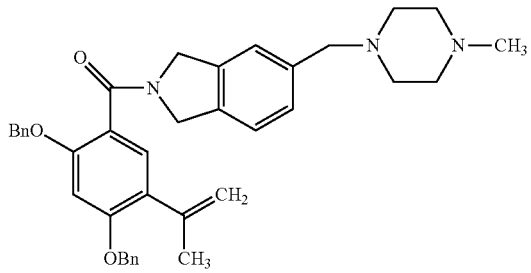 [SMILES: C=C(C)c1cc(C(=O)N2Cc3ccc(CN4CCN(C)CC4)cc3C2)c(OCc2ccccc2)cc1OCc1ccccc1]

A solution of the resorcinol acid (Step 6, 23.7 g, 63.4 mmol) and 1-hydroxybenzotriazole (10.21 g, 66.7 mmol) were dissolved in DMF (92 mL) and to this solution was added N-ethyl-N'-(3-dimethylaminopropyl)carbodiimide hydrochloride (12.8 g, 66.8 mmol). The solution was stirred at RT for 40 mins and this solution was added to the solution of the amine from Step 11 (66.8 mmol) together with DMF (5 mL) washings. The solution was degassed and the solution stirred at RT for 16 h. To the solution was added 10% K$_2$CO$_3$ (500 mL) and EtOAc (500 mL) and the organic phase was washed sequentially with 10% K$_2$CO$_3$ (500 mL), water (4×100 mL) and saturated brine (200 mL). The solution was evaporated to a small volume and 20% EtOAc in heptane (250 mL) was added and stored at 0°. The solid which had formed was removed by filtration, washed with heptane twice and was dried in vacuo to give the title compound 35.05 g (94.4%). $^1$H NMR (400 MHz, Me-d$_3$-OD): 7.49-7.10 (m, 14H), 6.86 (d, J=2.5 Hz, 1H), 5.17 (d, J=2.5 Hz, 4H), 5.09 (d, J=11.3 Hz, 2H), 4.88 (s, 2H), 4.63 (s, 2H), 3.54 (d, J=16.0 Hz, 2H), 2.50 (s, 7H), 2.28 (d, J=7.6 Hz, 3H), 2.11 (s, 3H).

Step 13

(2,4-Dihydroxy-5-isopropyl-phenyl)-[5-(4-methyl-piperazin-1-ylmethyl)-1,3-dihydro-isoindol-2-yl]-methanone

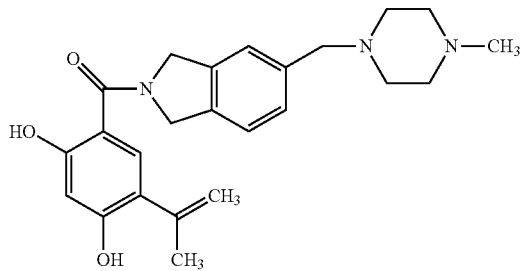 [SMILES: C=C(C)c1cc(C(=O)N2Cc3ccc(CN4CCN(C)CC4)cc3C2)c(O)cc1O]

The product from Step 12 (4.7 g) was dissolved in 1:1 MeOH/water (98 mL) and after purging with N$_2$ 10% Pd/C and K$_2$CO$_3$ (2.38 g, 17.2 mmol) were added and the suspension was hydrogenated for 16 h under an atmosphere of H$_2$. The solution was filtered and the solvent evaporated. To the residue was added aqueous 2M-HCl (40 mL) and the solution was washed with 1:1 EtOAc/petrol (40 mL×2) and then the pH adjusted to pH 8.5 by addition of NaOH and EtOAc (50 mL) added. The solution was heated to 60° C. and the aqueous phase removed. The hot organic phase was washed with water (30 mL) and then evaporated to a small volume (ca. 5 mL) and allowed to stand at RT 16 h with seeding. To the crystalline material was added 1:1 EtOAc/petrol (10 mL) and the mixture was filtered and dried to give the title compound as the free base 1.76 g. $^1$H NMR (400 MHz, Me-d$_3$-OD): 7.29 (s, 3H), 7.19 (s, 1H), 6.39 (s, 1H), 4.91 (s, 4H), 3.56 (s, 2H), 3.28-3.15 (m, 1H), 2.53 (s, 8H), 2.31 (s, 3H), 1.23 (d, J=6.9 Hz, 7H).

Optional Step 14

Purification of (2,4-Dihydroxy-5-isopropyl-phenyl)-[5-(4-methyl-piperazin-1-ylmethyl)-1,3-dihydro-isoindol-2-yl]-methanone In some batches of product, the title compound (X=H in the formula) can contain small amounts of the impurity 2,4-Dihydroxy-5-(2-hydroxyprop-2-yl)-phenyl)-[5-(4-methyl-1-piperazin-1-ylmethyl)-1,3-dihydro-isoindol-2-yl]-methanone (X=OH in the formula). The impurities can be removed by the following method.

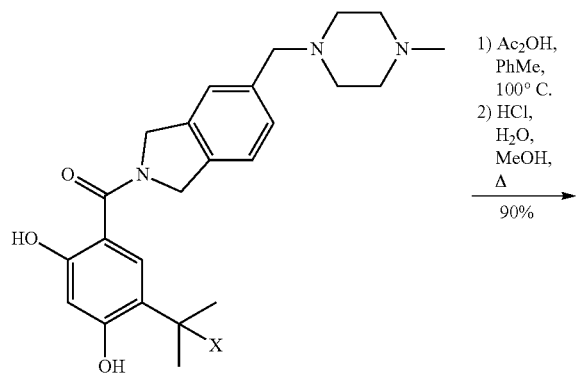

X = H and OH

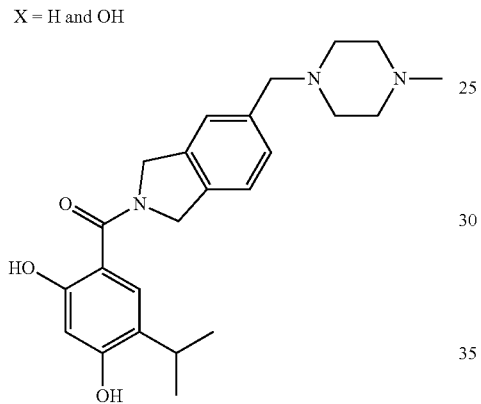

Acetic anhydride (1.04 ml, 11.0 mmol) was added to a stirred suspension of impure 2-(2,4-dihydroxy-5-isopropyl-benzoyl)-5-(4-methylpiperazin-1-ylmethyl)-1,3-dihydroisoindole (2.05 g, 5.0 mmol) in toluene (20 ml) and the resulting mixture was stirred and held at 100° C. for 16 hours. Upon cooling to room temperature the solvent was removed in vacuo to afford a brown oil which was dissolved in methanol (20 ml). Concentrated hydrochloric acid (1 ml) was added and the mixture was stirred and held at reflux for 5 hours. Upon cooling to room temperature, the organic solvent and volatile material were removed in vacuo and the aqueous residue was diluted with water (25 ml) and basified to pH 8 with vigorous stirring by the careful addition of 10% aqueous potassium carbonate solution. 50% Ethyl acetate in heptane (50 ml) was added and the mixture was stirred vigorously at room temperature for 16 hours. The solid material was collected by suction filtration, rinsed with 50% ethyl acetate in heptane (50 ml), sucked dry under reduced pressure and dried overnight in a vacuum oven at 50° C. to afford 2-(2,4-dihydroxy-5-isopropylbenzoyl)-5-(4-methyl-piperazin-1-ylmethyl)-1,3-dihydroisoindole (1.85 g, 90%) as an off-white solid. $^1$H NMR (DMSO-$d_6$) 10.07 (1H, br s), 9.60 (1H, br s), 7.24 (3H, m), 7.06 (1H, s), 6.40 (1H, s), 4.76 (4H, br s), 3.44 (2H, s), 3.10 (1H, m), 2.32 (8H, m), 2.14 (3H, s), 1.15 (6H, d). MS: [M+H]$^+$ 410.

Example 2

(2,4-Dihydroxy-5-isopropyl-phenyl)-[5-(4-methyl-piperazin-1-ylmethyl)-1,3-dihydro-isoindol-2-yl]-methanone L-lactate salt (form FL1)

The product of Example 1 (1.24 g, 3.303 mmol) was suspended in ethanol (3 mL) and EtOAc (5 mL) and a solution of L-lactic acid (0.285 g, 3.13 mmol) dissolved in ethanol (3 mL) was added. The solution was heated until clear and then was filtered. EtOAc (5 mL) was used to wash the filter and the combined filtrates were stirred at RT for 2 h with seeding. The crystalline mass which formed was removed by filtration, was washed with EtOAc and then dried in vacuum at 50° C. to give the title compound 1.29 g. $^1$H NMR (400 MHz, Me-$d_3$-OD): 7.30 (s, 3H), 7.18 (s, 1H). 6.39 (s, 1H), 4.91 (s, 4H), 4.08 (q, J=6.8 Hz, 1H). 3.70-3.63 (m, 2H), 3.28-3.15 (m, 1H), 3.01 (s, 4H), 2.68 (m, 7H), 1.36 (d, J=6.8 Hz, 3H), 1.23 (d, J=6.9 Hz, 6H).

Example 2A (2,4-Dihydroxy-5-isopropyl-phenyl)-[5-(4-methyl-piperazin-1-ylmethyl)-1,3-dihydro-isoindol-2-yl]-methanone L-lactate salt Example 2A describes a synthetic route containing essentially the same process steps as the route described in Examples 1 and 2 but wherein the process conditions are more suited to larger scale reactions.

Step 1

4-Acetoxy-2-hydroxy-benzoic acid methyl ester

To a heated solution (50° C.) of resorcinol methyl ester (16.5 Kg, 98.1 mol) and N,N-dimethyl-4-aminopyridine (89.1 g, 0.73 mol, 7.4 mol %) in toluene (66 L) was slowly added (over 2 h) acetic anhydride (9.9 L, 104.9 mol). The solution was heated to 50° C. for a further 1.5 h and then the solvent was removed by evaporation at 50° C. to a small volume and the residue was azeotroped once with toluene. To the residual oil was immediately added toluene (33 L) whilst still warm and the solution used for Step 2 without further purification.

Step 2

5-Acetyl-2,4-dihydroxy-benzoic acid methyl ester

The toluene solution from Step 1 was cooled in an ice bath under $N_2$ and triflic acid (9.44 L) added slowly over 3 h. On stirring a fine white solid was formed which dissolved on warming to RT over 20 h and then stirring at RT for 37 h to give a yellow solution. To the solution was added acetyl chloride (726 mL) and the solution stirred at RT for a further 1 h. This solution was cannulated into a stirred cooled (0° C.) solution of EtOAc (217.8 L) and NaOAc.3H$_2$O (14.52 Kg) dissolved in water (145 L). The organic phase was washed with saturated brine (twice, 72.6 L), and was evaporated to 5.5 Kg. Toluene: Isopropanol (2:3) was added and the crystalline solid removed by filtration and dried to give 12.6 Kg (61% over 2 steps), mp 124-126° C.

Step 3

5-Acetyl-2,4-bis-benzyloxy-benzoic acid methyl ester

To a stirred solution of benzyl bromide (16.14 L, 136 mol) and anhydrous potassium carbonate (20.25 Kg, 147.6 mol) in acetonitrile (184.5 L) was added methyl 5-acetyl-2,4-dihydroxybenzoate (14 Kg, 66.6 mol, step 2) in 6 portions over 5 h. The mixture was stirred and held at reflux for 20 hours, cooled to room temperature the mixture was poured onto water (682 L) and stirred vigorously for 2 hours. The solids were collected by centrifugation and dried under reduced pressure to constant mass in a vacuum oven at 60° C. overnight to afford methyl 5-acetyl-2,4-bis-benzyloxy-benzoate (23.5 Kg, 97.3%) as a cream solid mp 114-115° C.

Step 4

2,4-Bis-benzyloxy-5-isopropenyl-benzoic acid methyl ester

A solution of potassium tert-butoxide (6.72 Kg, 60.1 mol) in anhydrous THF (60 L) was added over 3 h to a stirred suspension of methyltriphenylphosphonium bromide (21.43 Kg, 60.1 mol) and methyl 5-acetyl-2,4-bis-benzyloxyben-zoate (21.3 Kg, 54.6 mol, step 3) in anhydrous tetrahydrofuran (213 L) at 15° C. The mixture was stirred at 15° C. for 70 mins and the warmed to 20° C. over 60 mins. Methanol (27.3 L) was added to quench excess phosphorus ylide and the solvent was concentrated in vacuo followed by addition of EtOAc and water. The organic phase was treated with activated charcoal, filtered and evaporated to a small volume. The residue was crystallised from boiling MeOH and the solids were collected by suction filtration, washed with methanol and dried under reduced pressure to afford methyl 2,4-bis-benzyloxy-5-isopropenyl-benzoate 18.1 Kg (85%) as pale yellow needles mp 92-94° C. (99.6% pure by hplc).

Step 5

2,4-Bis-benzyloxy-5-isopropenyl-benzoic acid

Potassium hydroxide (0.527 Kg. 9.4 mol) was added to a stirred suspension of methyl 2,4-bis-benzyloxy-5-isoprope-nyl-benzoate (3.1 Kg, 8 mol, step 4) in methanol (18.6 L) and water (12.4 L) and the mixture was stirred and held at reflux for 3 hours. The methanol was removed under partial vacuum from the vessel, and to the remaining solution was added toluene (62 L). The solution was heated to 40° C. and to the mixture was added conc HCl (1.36 L). The biphasic mixture is heated to 50° C. and the phases separated. The organic phase was washed with water (31 L) at 50° C. and the organic phase was evaporated under reduced pressure to give 2,4-bis-benzyloxy-5-isopropenyl-benzoic acid 2.851 Kg (95% yield) as a colourless solid.

Step 6

Di-prop-2-ynyl-carbamic acid benzyl ester

To a cooled (5° C.) solution of $K_2CO_3$ (4 Kg, 29.0 mol) in water (17.5 L) and toluene (12.5 L) was added diprop-argylamine (2.50 Kg, 26.88 mol). Benzyloxychloroformate (4.8 Kg, 28.14 mol) was added at a rate such that T<10° C. The solution was stirred at 5° C. for 10 mins and then allowed to warm to RT. The aqueous phase was separated and the organic phase was washed with 0.2M HCl (12.5 L), sat $NaHCO_3$ (13.5 L) and brine (17 L) and the resultant solution used in step 7 (assayed to contain 6.23 Kg, 102% based on an evaporated portion).

Step 7

5-Hydroxymethyl-1,3-dihydro-isoindole-2-carboxylic acid benzyl ester

A solution of propargyl alcohol (2.11 Kg, 37.7 mol) in toluene (32.48 L) was degassed and heated to 55° C. The solution of di-prop-2-ynyl-carbamic acid benzyl ester (4.06 Kg, 17.86 mol, step 6) in toluene and Wilkinsons catalyst (0.162 Kg) were added in 10 equal portions such that temperature <65° C. (the exotherm was allowed to subside before the next addition was made). The solution was then stirred at 55° C. for 1 h and then cooled to 20° C. DCM (8.12 L) was added and the mixture was concentrated to a small volume. Toluene (8 L) was added and the solution evaporated to constant weight giving the title compound 5.72 Kg (113%).

Step 8

5-Methanesulfonyloxymethyl-1,3-dihydro-isoindole-2-carboxylic acid benzyl ester To a cooled solution (5° C.) of 5-hydroxymethyl-1,3-dihydro-isoindole-2-carboxylic acid benzyl ester (11 Kg, 38.8 mol, step 7) and Et-3N (7.04 L, 50.6 mol) in DCM (55 L) was added methanesulphonyl chloride (2.97 L, 38.4 mol) so that the internal temp <10° C. After stirring for 0.5 h at 5° C. the solution was used below in step 9.

Step 9

5-(4-Methyl-piperazin-1-ylmethyl)-1,3-dihydro-isoindole-2-carboxylic acid benzyl ester dihydrochloride salt

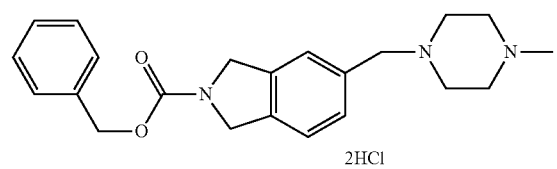 [SMILES: CN1CCN(Cc2ccc3c(c2)CN(C(=O)OCc2ccccc2)C3)CC1]

2HCl

The solid from Step 8 (assume 0.232 mol) was dissolved in acetone (700 mL) and this solution was added over 45 mins to a cooled (internal temp 15-17° C.) suspension of $K_2CO_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried ($MgSO_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. $^1$H NMR (400 MHz, Me-d$_3$-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Step 9

5-(4-Methyl-piperazin-1-ylmethyl)-1,3-dihydro-isoindole-2-carboxylic acid benzyl ester DCM (33 L) and N-methylpiperazine (21.45 L, 193.4 mol) were stirred at 25° C. and the solution from step 8 added over a minimum of 30 mins such that temperature 20-30° C. After stirring the solution for a further 30 mins water (55 L) was added and the organic phase was washed with water (2×55 L). The product was extracted into 0.8M HCl (66 L) and the layers separated. The aqueous phase was washed with DCM (55 L) and then basified with 2M NaOH to pH 10-11 and the product was extracted into EtOAc (2×55 L). The combined organic phase were filtered to remove solids and the evaporated followed by azeotroping with toluene and drying to constant weight to give the title compound, 6.63 kg (47% yield, 98% pure by hplc).

Step 10

5-(4-Methyl-piperazin-1-ylmethyl)-2,3-dihydro-1H-isoindole

To a degassed solution of 5-(4-Methyl-piperazin-1-ylmethyl)-1,3-dihydro-isoindole-2-carboxylic acid benzyl ester (Step 9, 1.3 Kg, 3.55 mol) dissolved in EtOH (13 L) was added 10% Pd/C (0.065 Kg). Hydrogen was passed through the mixture at 30° C. for 4 h or until complete by NMR. The solution was then stirred for 1 h under an atmosphere of N$_2$ and then filtered to remove the catalyst through a GF/F filter followed by filtration through a Cuno filter. The filtrate was evaporated to a small volume, azeotroped with toluene (3.9 L) and dried to constant weight yielding the title compound as a red/black oily solid (0.78 Kg) which was stored under nitrogen until required.

Step 11

(2,4-Bis-benzyloxy-5-isopropenyl-phenyl)-[5-(4-methyl-piperazin-1-ylmethyl)-1,3-dihydro-isoindol-2-yl]-methanone 1,1'-Carbonyldiimidazole (4.82 Kg, 29.8 mol) was added to a solution of 2,4-bis-benzyloxy-5-isopropenyl-benzoic acid (10.58 Kg, 28.3 mol, step 5) in DMF (21.2 L) at 25° C. After 20 mins at 25° C. a solution of 5-(4-Methyl-piperazin-1-ylmethyl)-2,3-dihydro-1H-isoindole (7.2 Kg, 31.1 mol, step 10) in DMF (7.2 L) maintaining a temperature below 35° C. and the solution stirred at 25° C. for a minimum of 12 h. The solid which had formed was removed by filtration, washed with isopropyl acetate (2×21.6 L) and dried at 35° C. to constant weight to give the title compound 8.7 Kg (77% yield, purity by hplc 97.5%).

Step 12

(2,4-Dihydroxy-5-isopropyl-phenyl)-[5-(4-methyl-piperazin-1-ylmethyl)-1,3-dihydro-isoindol-2-yl]-methanone The product from Step 11 (0.9 Kg, 1.53 mol) was dissolved in isopropanol (6.8 L) and water (1.04 L) and after purging with N$_2$ 10% Pd/C (90 g) and K$_2$CO$_3$ (0.212 Kg, 1.53 mol) were added and the suspension was hydrogenated for 60 to 70 mins under an 3 Barr pressure of H$_2$. The solution was diluted with water (0.5 L) and filtered. To the filtrate was added aqueous HCl (30% hydrochloric acid, 0.85 Kg diluted with water 5.42 Kg) and the solution was concentrated at 60° C. under vacuum (removing 10 L isopropanol). Water (0.45 L) was added to the solution and concentration continued (until a further 10 L isopropanol had been removed). The aqueous phase was washed with EtOAc (4.61 L), diluted with acetonitrile (4.06 L) and netralised to pH 7.5-8.5 by addition of conc ammonia solution (0.35 Kg). The suspension was stirred for 2.5 h and then the solid was removed by filtration. The residue was washed with acetonitrile (2×0.8 L) and dried at 40° C. to constant weight to give the title compound 588 g (94% yield).

Step 13

(2,4-Dihydroxy-5-isopropyl-phenyl)-[5-(4-methyl-piperazin-1-ylmethyl)-1,3-dihydro-isoindol-2-yl]-methanone L-lactate salt (form FL1)

The product of Step 12 (646 g, 1.58 mol) was dissolved in ethanol (5.17 L) and the solution filtered. A solution of L-lactic acid (142 g, 1.58 mol) dissolved in ethanol (2.59 L) was filtered and added to the solution of the filtered solution (above) and then to the mixture was added EtOAc (7.75 L). The suspension was stirred at RT for 12 h and then cooled to 5° C. for a further 2 h. The solid which had formed was removed by filtration, washed with EtOAc (2×2.58 L) and heptane (2×1.94 L) and dried to constant weight at 35° C. giving the title compound (581 g, 74% yield).

Example 3

(2,4-Dihydroxy-5-isopropyl-phenyl)-[5-(4-methyl-piperazin-1-ylmethyl)-1,3-dihydro-isoindol-2-yl]-methanone dihydrochloride salt (form FH3)

The product of Example 1 (0.49 g, 1 mmol) was dissolved in ethanol (10 mL) and 4M HCl in dioxane (0.5 mL, 2 mmol) was dissolved with warming and then the solution was evaporated to dryness. The residue was dissolved with warming ethanol:water (9:1; 5 mL). The solution was stirred for 16 h with seeding and the solid which formed was removed by filtration and was dried in vacuo to give the title compound. $^1$H NMR (400 MHz, Me-d$_3$-OD): 7.63-7.52 (m, 2H), 7.47 (s, 1H), 7.17 (s, 1H), 6.40 (s, 1H), 4.96 (d, J=7.0 Hz, 4H), 4.47 (s, 2H), 3.87-3.40 (m, 8H), 3.30-3.16 (m. 1H), 3.02 (s, 3H), 1.23 (d, J=6.9 Hz, 6H).

Example 4

Synthesis of (2,4-Dihydroxy-5-isopropyl-phenyl)-[5-(4-ethyl-piperazin-1-ylmethyl)-1,3-dihydro-isoindol-2-yl]-methanone

4A. Synthesis of 2,4-Bis-benzyloxy-5-isopropenyl-N,N-di-prop-2-ynyl-benzamide

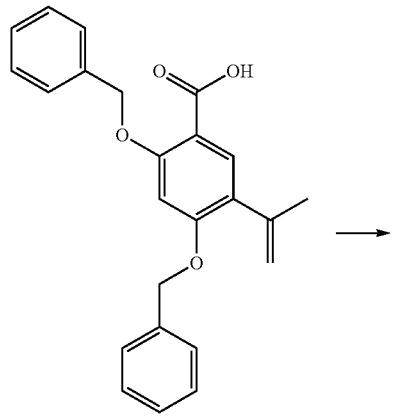

A stirred solution of 2,4-bis-benzyloxy-5-isopropenyl-benzoic acid (Example 1 Step 6) (1 equivalent) in dichloromethane (10 ml) was treated successively with N-ethyl-N'-(3-dimethylaminopropyl)carbodiimide hydrochloride (1.2 equivalents), 1-hydroxybenzotriazole (1.2 equivalents) and dipropargylamine (1.5 equivalents) and the mixture was stirred at room temperature overnight. The mixture was washed successively with 2M hydrochloric acid and 2M sodium hydroxide, the organic layer was separated and the solvent removed in vacuo to afford the product which was either obtained pure or was purified by column chromatography on silica (eluting with mixtures of ethyl acetate in petroleum ether or methanol in ethyl acetate as appropriate). MS: [M+H]+ 450

4B. Synthesis of 1-ethyl-4-prop-2-ynyl-piperazine

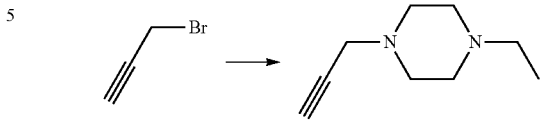

To the 1-ethylpiperazine (2.33 g, 20.2 mmol) and K$_2$CO$_3$ (2.79 g, 20.2 mmol) in acetone (27 ml) was added propargyl bromide (2.00 g, 13.5 mmol) dropwise at 0° C. under N$_2$. The reaction was stirred at room temperature overnight. The reaction was filtered and the salts washed with a small amount of acetone. The filtrates were combined and evaporated gently to concentration. The residue was taken up in EtOAc and washed with water. The aqueous phase was re-extracted with EtOAc. The combined organic layers were washed with brine and dried over MgSO$_4$. The product was filtered and evaporated to dryness to leave a pale orange oil.

4C. Synthesis of (2,4-Bis-benzyloxy-5-isopropenyl-phenyl)-[5-(4-ethyl-piperazin-1-ylmethyl)-1,3-dihydro-isoindol-2-yl]-methanone

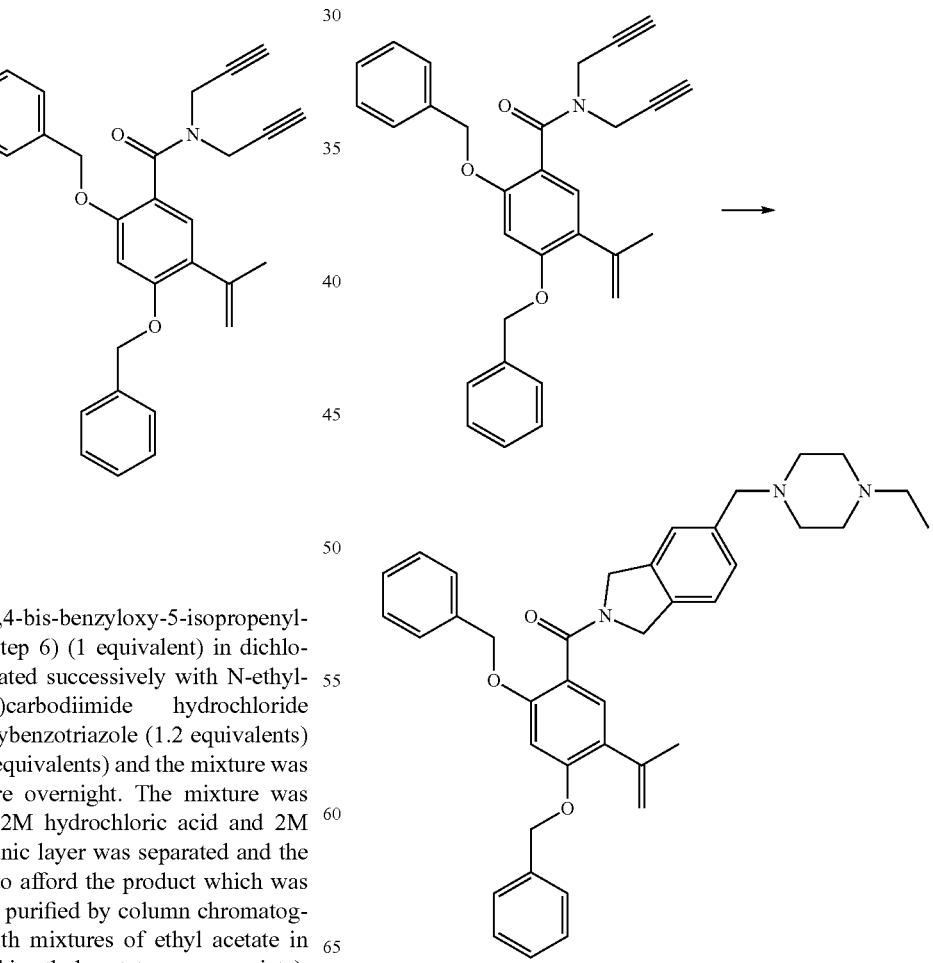

The title compound was prepared using the method of Example 5B except that purification was carried out using column chromatography rather than salt formation. MS: [M+H]+ 602.

4D. Synthesis of (2,4-Dihydroxy-5-isopropyl-phenyl)-[5-(4-ethyl-piperazin-1-ylmethyl)-1,3-dihydro-isoindol-2-yl]-methanone

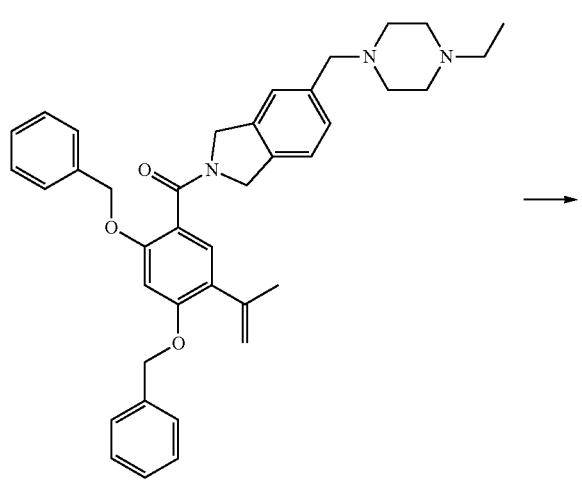

Hydrogenation of (2,4-bis-benzyloxy-5-isopropenyl-phenyl)-[5-(4-ethyl-piperazin-1-ylmethyl)-1,3-dihydro-isoindol-2-yl]-methanone using the method described in Example 1 Step 13 except that the work up and purification procedures were changed. Thus, following hydrogenation, the catalyst was filtered and the filtrate was evaporated. Water and EtOAc were added to the product and the aqueous layer was neutralised. The product was then extracted with EtOAc (×3). The combined organic layers were washed with brine and dried over MgSO$_4$. The resulting solution was filtered and evaporated to dryness to leave a pale yellow oil/solid. The product was purified by column chromatography (gradient elution 100% DCM to 10% MeOH in DCM) to yield the product as pale yellow solid. MS: [M+H]+ 424.

Example 5

Alternative synthesis of 5-(4-Methyl-piperazin-1-ylmethyl)-2,3-dihydro-1H-isoindole

5A. Synthesis of 1-methyl-4-prop-2-ynyl-piperazine

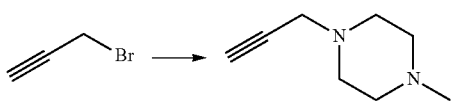

To 1-methylpiperazine (37.7 ml, 337 mmol) and K$_2$CO$_3$ (46.6 g, 337 mmol) in acetone (380 ml) was added propargyl bromide (25 ml, 225 mmol, 80% in toluene) in acetone (70 ml) dropwise at 0° C. under N$_2$. The internal temperature of the reaction was kept <10° C. The reaction was stirred at room temperature for 3 hours. The reaction was filtered, and the salts were washed with small portions of acetone (×2). The filtrates were combined evaporated to concentration (gently). To the residue was added water and the product was extracted with DCM (×3). The combined organic layers were washed with brine and dried over MgSO$_4$. The product was filtered and evaporated to dryness to yield 1-methyl-4-prop-2-ynyl-piperazine as a yellow oil.

5B. Synthesis of 5-(4-Methyl-piperazin-1-ylmethyl)-1,3-dihydro-isoindole-2-carboxylic acid tert-butyl ester

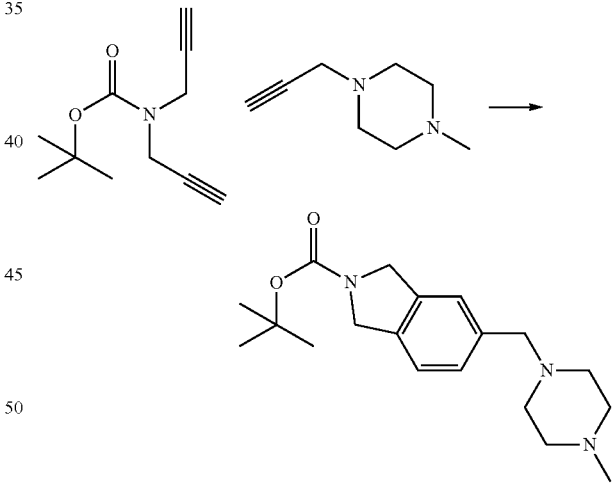

A solution of N-boc-dipropargylamine (36.3 ml, 226 mmol, 86% pure) in EtOAc (30 ml) was made up and degassed by bubbling through N$_2$, in a separating funnel. Tris(triphenylphosphine)rhodium(I) chloride (1.39 g, 1.50 mmol, 1 mol %) was added to pre-degassed EtOAc (15 ml) in a second separating funnel. (NB CpRu(COD)Cl) can also be used as an alternative catalyst).

In the main reactor flask, 1-propargyl-4-methylpiperazine (32.3 ml, 150 mmol, 90% pure) was diluted with EtOAc (75 ml) and was degassed by bubbling N$_2$ through the mixture The mixture was cooled in an ice-water bath and then the tris(triphenylphosphine)rhodium(I) chloride (1.39 g, 1 mol %) in EtOAc was added. Slow addition of N-boc-dipropargylamine/EtOAc was undertaken to yield a mild exotherm. The internal temperature rose to 25° C. and remained at this temperature. After addition was approximately one third complete (~45 minutes), the exotherm tailed off (despite the continual slow addition of N-boc-dipropargylamine/ EtOAc). Another portion of tris(triphenylphosphine) rhodium(I) chloride catalyst (1.39 g, 1 mol %) in EtOAc (15 ml, pre-degassed) was made up and added very slowly to the reaction. After a couple of minutes a new exotherm started and grew to 30° C. The reaction temperature was cooled gently by the addition of a small amount of ice to the water bath. Once the exotherm began to subside, slow addition of N-boc-dipropargylamine/EtOAc was continued. The entire addition was carried out over a 2 hour period. The reaction mixture was then left at room temperature overnight before diluting with EtOAc and washing with NH4Cl (×2) (aqueous, saturated) to remove excess 1-propargyl-4-methylpiperazine. The mixture was diluted with a small amount of water to dissolve the salts. The organic layer was washed with water, brine and dried over MgSO$_4$. The product was filtered and evaporated to dryness to leave a brown oil.

To the oil residue obtained was added n-heptane. The oil/heptane was left to stand (~10 minutes) until a red precipitate formed. The precipitate was filtered and washed with fresh n-heptane (×2). The filtrates were dried to yield the product as a red oil.

The desired product was further purified by forming the toluenesulphonic acid (TsOH) salt. Thus, the crude product was taken up in MeOH (20 ml) and the TsOH.H$_2$O (1 eq to estimated purity by NMR) was added. The solution was evaporated to dryness, and then dissolved in toluene (×1) and re-evaporated. The resulting product was taken up in ether. After a few minutes, a precipitate and solution formed. The precipitate was filtered and washed with more ether (×2) until the filtrate was colourless. The yellow solid was dried to yield the product as the TsOH salt. MS: [M+H]+ 332.

5C. Synthesis of 5-(4-Methyl-piperazin-1-ylmethyl)-2,3-dihydro-1H-isoindole

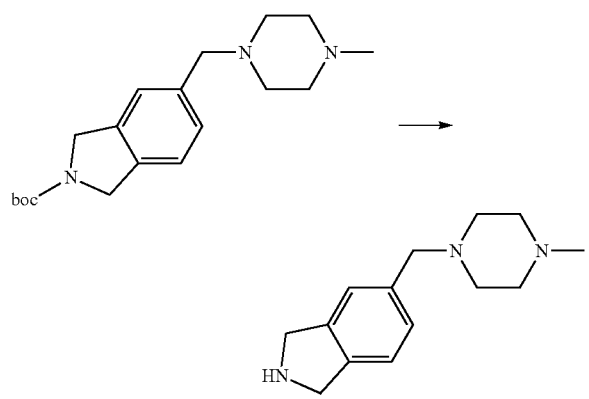

The isoindoline tosylate salt was taken up in DCM (0.3 M) and TFA (12 eq.) added slowly at 0° C. The reaction was stirred overnight at room temperature. The reaction was evaporated to dryness and then with toluene/MeOH (×3) to yield the product as a mixture of acid addition salts. MS: [M+H]+ 232.

The compound of Example 5C can be used in the method of Example 1 Step 12.

Example 6

Alternative synthesis of 5-hydroxymethyl-1,3-dihydro-isoindole-2-carboxylic acid benzyl ester 6A. Methyl 2-benzyl-2,3-dihydro-1H-isoindole-5-carboxylate

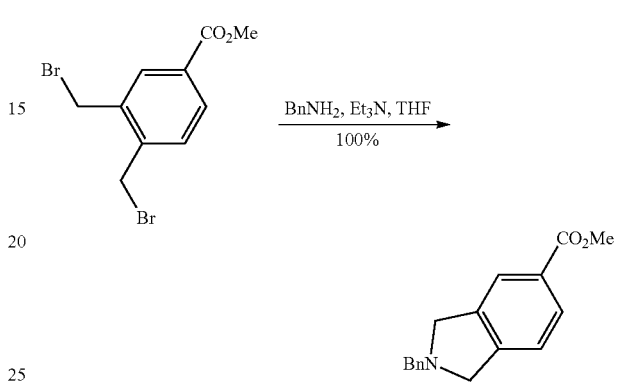

Benzylamine (3.21 g, 30.0 mmol) in anhydrous tetrahydrofuran (25 ml) was added to a stirred mixture of methyl 3,4-bis-(bromomethyl)benzoate (9.66 g, 30.0 mmol) (obtained from Fluorochem) and triethylamine (9 ml, 64.7 mmol) in anhydrous tetrahydrofuran (50 ml) and the resulting mixture was stirred at room temperature for 3 hours. The solvent was removed in vacuo at 40° C. and the residue partitioned between ethyl acetate (100 ml) and water (100 ml). The organic layer was washed with a further portion of water (100 ml), separated and the solvent removed in vacuo at 40° C. to afford methyl 2-benzyl-2,3-dihydro-1H-isoindole-5-carboxylate as a pale orange solid that was used immediately without further purification as described below. $^1$H NMR (DMSO-d$_6$) 7.82 (2H, m), 7.40-7.25 (6H, m), 3.90 (3H, s), 3.88 (2H, s), 3.84 (4H, s). MS: [M+H]$^+$ 268.

6B. (2-Benzyl-2,3-dihydro-1H-isoindol-5-yl)-methanol

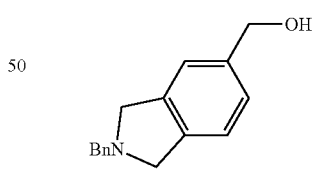

Methyl 2-benzyl-2,3-dihydro-1H-isoindole-5-carboxylate (from above) was dissolved in anhydrous tetrahydrofuran (75 ml) and added dropwise over 15 minutes to a rapidly stirred suspension of lithium aluminium hydride (1.71 g, 45.0 mmol) in anhydrous tetrahydrofuran (75 ml). The mixture was stirred at room temperature for 2 hours whereupon excess lithium aluminium hydride was destroyed by the slow dropwise addition of 1 M sodium sulphate solution (12 ml). The solids were removed by filtration, rinsed with ethyl acetate (2×50 ml) and sucked dry. The solvent was removed in vacuo to afford (2-benzyl-2,3-dihydro-1H-isoindol-5-yl)-methanol (7.15 g, 99%) as a tan solid. $^1$H NMR (DMSO-d) 7.40-7.30 (4H, m), 7.28 (1H, m), 7.17-7.10 (3H, m), 5.10 (1H, t), 4.47 (2H, d), 3.85 (2H, s), 3.82 (2H, s), 3.80 (2H, s). MS: [M+H]+ 240.

6C. (2,3-Dihydro-1H-isoindol-5-yl)-methanol

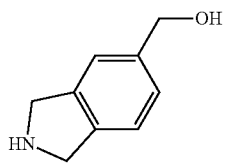

10% Palladium on activated carbon (200 mg) was added to a solution of (2-benzyl-2,3-dihydro-1H-isoindol-5-yl)-methanol (2.39 g, 10.0 mmol) in ethanol (60 ml) and the resulting mixture was placed in a Parr apparatus, heated to 50° C. and shaken under a hydrogen atmosphere at 60 psi for 30 hours. Upon cooling to room temperature the mixture was filtered under gravity, the solids were rinsed with ethanol (2×10 ml) and the solvent removed in vacuo to afford (2,3-dihydro-1H-isoindol-5-yl)-methanol (1.49 g, 100%) as an off-white solid. $^1$H NMR (DMSO-$d_6$) 7.20 (1H, s), 7.18 (1H, d), 7.12 (1H, d), 5.10 (1H, br s), 4.46 (2H, s), 4.05 (4H, s). MS: [M+H]+ 150.

6D. 5-Hydroxymethyl-1,3-dihydro-isoindole-2-carboxylic acid benzyl ester

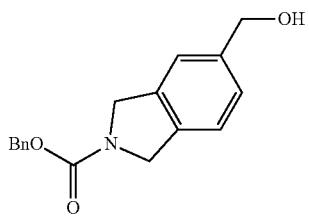 [SMILES: O=C(OCc1ccccc1)N1Cc2ccc(CO)cc2C1]

A mixture of (2,3-dihydro-1H-isoindol-5-yl)-methanol (1.34 g, 9.0 mmol) in anhydrous tetrahydrofuran (50 ml) was warmed gently to aid dissolution and allowed to cool to room temperature. Triethylamine (1.5 ml, 10.8 mmol) was added and the stirred mixture was treated dropwise with benzyl chloroformate (1.35 ml, 9.5 mmol) and stirred at room temperature for 3 hours. The solvent was removed in vacuo and the residue partitioned between ethyl acetate (30 ml) and 2M hydrochloric acid (30 ml). The organic layer was washed with water (30 ml), separated and the solvent removed in vacuo to afford a pink oil that solidified upon standing. The solids were triturated with 10% ethyl acetate in hexane (10 ml), filtered, rinsed with heptane (10 ml) and sucked dry to afford the title compound (2.5 g, 98%) as a pale pink solid. $^1$H NMR (DMSO-$d_6$) 7.45-7.21 (8H, m), 5.20 (1H, t), 5.17 (2H, s), 4.71 (2H, br s), 4.64 (2H, br s), 4.50 (2H, d). MS: [M+H]+ 284.

The title compound can be used in Step 9 of Example 1.

BIOLOGICAL ACTIVITY

Example 7

Isothermal Titration Calorimetry

The ability of the compounds of the invention to bind to human Hsp90 proteins was determined using isothermal titration calorimetry.

Isothermal titration calorimetry (ITC) experiments were performed with a VP-ITC titration calorimeter (Microcal Inc., Northampton, Mass., USA). Cloning, expression, and purification of the Human Hsp90α N-terminal domain were performed according to published methods (Jez, J. M. et al, Chem. Biol. 2003 April; 10(4):361-8.) Solutions of the human Hsp90α N-terminal domain and compound were prepared in a buffer comprising 25 mM Tris, 100 mM NaCl, 1 mM $MgCl_2$, 1 mM TCEP, 5% DMSO, pH 7.4. All solutions were filtered and degassed prior to a titration being carried out. The enthalpy change resulting from each injection of ligand was obtained through integration of the calorimetric signal. Data were analysed using Origin 7.0 (Microcal Software Inc., Northampton, Mass.). Heats of dilution were estimated using the final injections of each individual titration and subtracted before data fitting. Different ITC experimental formats were employed in order to obtain compound dissociation constants (Kd's) over a wide range of affinities. For weakly binding compounds a low c-value ITC method was used (Turnbull W. B. & Daranas A. H. J. Am. Chem. Soc. 2003 Dec. 3; 125(48):14859-66) in which the protein was present at 10-20 μM in the calorimetric cell and the compound concentration was 1-20 mM in the injection syringe. In this type of experiment the stoichiometry parameter (N) was locked at 1 for data fitting. For Kd's in the 20-0.004 μM range the experiment was configured such that the binding site concentration divided by the Kd (c-value) was between 5 and 1000. For the majority of these experiments the protein concentration in the calorimetric cell was in the range 4-100 μM and the ligand concentration in the injection syringe ranged from 50-1500 μM. In rare cases where compound solubility was limiting, the compound solution was placed in the calorimetric cell and titrated with protein from the injection syringe, maintaining a c-value between 5 and 1000. Competition ITC experiments were used to access Kd's<4 nM by performing the titration in the presence of a weaker binding competitor according to the method described in Sigurskjold B. W. Anal Biochem. 2000 Jan. 15; 277(2):260-6.

Compound (1) has a Kd value of less than 0.1 micromolar.

Example 8

Anti-Proliferative Activity

The anti-proliferative activities of compounds of the invention can be determined by measuring the ability of the compounds to inhibition of cell growth in a number of cell lines such as the human colon cancer cell line HCT116. Inhibition of cell growth is measured using the Alamar Blue assay (Nociari, M. M, Shalev, A., Benias, P., Russo, C. Journal of Immunological Methods 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines can be obtained from the ECACC (European Collection of cell Cultures).

Compound (1) has an IC50 value of less than 0.1 micromolar against the HCT116 cell line.

The anti-proliferative activity of (2,4-dihydroxy-5-isopropyl-phenyl)-[5-(4-methyl-piperazin-1-ylmethyl)-1,3-dihydro-isoindol-2-yl]-methanone L-lactate salt was tested in assays against one hundred cell lines by Oncodesign (Dijon, France). The IC50 values against each cell line are set out in the table below and the figures in the table refer to nanomolar concentrations. The compounds were tested up to a concentration of 10,000 nanomolar.

| N° | Cell lines | Concentration of test compound (nanomolar) |
|---|---|---|
| | BLOOD | |
| 1 | ARH-77 | >10000 |
| 2 | BV-173 | 73 |
| 3 | CCRF-CEM | 107 |
| 4 | CCRF-CEM/VLB | >10000 |
| 5 | Daudi | 136 |
| 6 | EHEB | >10000 |
| 7 | HL-60 | 389 |
| 8 | HL-60/R¹0 | 847 |
| 9 | K-562 | 147 |
| 10 | K-562/Gleevec | 175 |
| 11 | KCL-22 | 24 |
| 12 | KG-1 | >10000 |
| 13 | LAMA-84 | 1098 |
| 14 | MC90 | 93 |
| 15 | NAMALWA | 93 |
| 16 | OCI-AML2 | >10000 |
| 17 | Raji | 881 |
| 18 | Ramos | 46 |
| 19 | RPMI 8226 | 10 |
| 20 | RPMI 8226/Dox40 | 213 |
| 21 | SUP-B15 | 37 |
| 22 | U-937 | 104 |
| | BRAIN | |
| 23 | CGL-1 | >10000 |
| 24 | CGL-3 | 75 |
| 25 | CGL-9 | 161 |
| | BREAST | |
| 26 | CAMA-1 | 22 |
| 27 | Evsa-T | 168 |
| 28 | HCC1954 | 28 |
| 29 | MCF-7 | >10000 |
| 30 | MCF-7/ras | 166 |
| 31 | MDA-MB-435 | 122 |
| 32 | MDA-MB-435S | 26 |
| 33 | ZR-75-1 | 131 |
| | COLON | |
| 34 | DLD-1 | 56 |
| 35 | HCT 116 | 38 |
| 36 | HCT-15 | >10000 |
| 37 | LoVo | 51 |
| 38 | LS 174T | 159 |
| | CONNECTIVE TISSUE | |
| 39 | SW-872 | >10000 |
| | HEAD AND NECK | |
| 40 | BB30-HNSCC | 273 |
| 41 | BB49-HNSCC | 146 |
| 42 | FaDu | 29 |
| 43 | KB | 48 |
| 44 | KB3 | 48 |
| 45 | LB1617-HNSCC | 139 |
| 46 | LB771-HNSCC | 391 |
| | KIDNEY | |
| 47 | A-498 | 267 |
| 48 | BB64-RCC | >10000 |
| 49 | BB65-RCC | 1251 |
| 50 | Caki-1 | >10000 |
| 51 | LB1047-RCC | 58 |
| 52 | LB996-RCC | 158 |
| | LIVER | |
| 53 | Hep 3B2.1-7 | 95 |
| 54 | SK-HEP-1 | >10000 |
| | LUNG | |
| 55 | A-427 | 130 |
| 56 | Calu-1 | 270 |
| 57 | Calu-3 | >10000 |
| 58 | Calu-6 | 32 |
| 59 | LB11-SCLC/OC1 | 17 |
| 60 | LB12-SCLC/OC2 | 52 |
| 61 | LB13-SCLC/OC3 | 21 |
| 62 | LB37-NSCLC | 63 |
| 63 | LB61-NSCLC | >10000 |
| 64 | NCI-H299 | 587 |
| 65 | NCI-H460 | 118 |
| 66 | NCI-H520 | 98 |
| 67 | NCI-H596 | 84 |
| 68 | NCI-H69 | 162 |
| 69 | NCI-H82 | >10000 |
| 70 | SK-MES-1 | 270 |
| | OVARY | |
| 71 | Caov-3 | 94 |
| 72 | IGROV-1 | 109 |
| 73 | IGROV-1/CDDP | 147 |
| 74 | NIH:OVCAR-3 | 45 |
| 75 | NIH:OVCAR-3/CPT20 | >10000 |
| 76 | PA-1 | >10000 |
| | PANCREAS | |
| 77 | BxPC-3 | 196 |
| 78 | Capan-2 | 144 |
| 79 | PANC-1 | 327 |
| | PROSTATE | |
| 80 | DU 145 | 85 |
| 81 | LNCaP-FGC | 78 |
| | SKIN | |
| 82 | A-375 | 1481 |
| 83 | A-375-SM | 340 |
| 84 | A-431 | 3799 |
| 85 | BB74-MEL | 162 |
| 86 | CMEL-5 | 130 |
| 87 | Hs 294T | 219 |
| 88 | LB1319-MEL | 35 |
| 89 | Malme-3M | 157 |
| 90 | SK-MEL-2 | 138 |

-continued

| N° | Cell lines | Concentration of test compound (nanomolar) |
|---|---|---|
| 91 | SK-MEL-5 | 185 |
| 92 | UZG4-MEL | 180 |
| STOMACH | | |
| 93 | AGS | 66 |
| 94 | Hs 746T | 34 |
| 95 | KATO III | 162 |
| THYROID | | |
| 96 | FTC-238 | 26 |
| URINARY BLADDER | | |
| 97 | J82 | 20 |
| 98 | LB796-BLC | 83 |
| 99 | LB831-BLC | 149 |
| 100 | T24 | 852 |

The results demonstrate that (2,4-dihydroxy-5-isopropyl-phenyl)-[5-(4-methyl-piperazin-1-ylmethyl)-1,3-dihydro-isoindol-2-yl]-methanone L-lactate has potent anti-proliferative activity against a wide range of different cell lines.

PHARMACEUTICAL FORMULATIONS

Example 9

(i) Tablet Formulation

A tablet composition containing a compound of the formula (1) or formula (2) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) or formula (2) with 100 mg lactose and filling the resulting mixture into standard opaque hard gelatin capsules.

(iii) Injectable Formulation I

A parenteral composition for administration by injection can be prepared by dissolving a compound of the formula (1) or formula (2) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) (e.g. in salt form) or formula (2) (2 mg/ml) and mannitol (50 mg/ml), sterile filtering the solution and filling into sealable 1 ml vials or ampoules.

(v) Injectable Formulation III

A formulation for i.v. delivery by injection or infusion can be prepared by dissolving the compound of formula (1) (e.g. in a salt form) or formula (2) in water at 20 mg/ml. The vial is then sealed and sterilised by autoclaving.

(vi) Injectable Formulation IV

A formulation for i.v. delivery by injection or infusion can be prepared by dissolving the compound of formula (1) (e.g. in a salt form) or formula (2) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) or formula (2) with pharmaceutical grade corn oil to give a concentration of 5 mg/ml. The composition is sterilised and filled into a suitable container.

(viii) Lyophilised Formulation

Aliquots of formulated compound of formula (1) or formula (2) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

ix

| 2% Topical Gel Formulation | |
|---|---|
| | % w/w |
| Compound | 2.00 |
| Hydroxypropyl Methyl cellulose (Methocel F4M) | 2.50 |
| Polyethyleneoxide (Polyox WSR-205) | 0.25 |
| Propylene glycol | 10.00 |
| Methylparaben | 0.15 |
| Propylparaben | 0.05 |
| Purified Water to | 100.00 |

Example 10

CRYSTAL STRUCTURE STUDIES

The compound of formula (1) and its salts exist in a number of different crystalline forms. These have been identified and characterised using the methods described below.

GENERAL METHODS

Single Crystal Diffraction Methodology

Crystallographic data were collected at room temperature (20° C.) using synchrotron radiation ($\lambda=0.775$ Å) from ESRF ID23.1 beamline equipped with φ goniometer and an ADSC Quantum 315 CCD detector. Images were collected in two φ scans with (φ=0-1800 and Δφ=1°., one with high radiation dose and one with low dose. Detector to crystal distance was 110 mm. Data collection was controlled by ProDC software and images were processed and scaled by Dtrek.

The crystal structures were solved using direct methods implemented in SHELXS-97 and refined by SHELXL-97.

Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors.

Powder Diffraction Methodology

Samples for X-ray powder diffraction (XRPD) data collection were gently ground by marble mortar and loaded into a crystallographic capillary (from Hampton Research, Quartz or Glass Type 10, 0.4 or 0.7 mm diameter). Diffraction patterns were collected at room temperature using CuKα radiation (λ=1.5418 Å) from a Rigaku rotating anode RU3HR, Osmic blue confocal optics, ¼ c goniometer and a Rigaku HTC image plate detector. 2D Images were collected while spinning φ axis with a detector to crystal distance of 250 mm. Data collection was controlled by CrystalClear software and 2D images were converted to 1D plot (2θ vs. Intensity) by Datasqueeze (intensity averaged over the azimuthal angle $0 \leq \chi \leq 360°$ for 2θ range 3-30° in 0.02° steps). In house program AstexXRPD was used for manipulation and visualisation of 1D XRPD patterns.

Determination of Salt Stoichiometry by Titration Experiments

In the following examples, where they relate to salts and the stoichiometry of the salt is given, the stoichiometry was determined using the following titration method.

A solution (KCl/HCl solution) of 150 mM KCl and 20 mM HCl was freshly prepared for each batch of titration experiments. An aliquot of 1 ml of the solution was titrated and the potentiometric titration curve thus produced was used as the control curve. All titrations were performed at 25° C. and with 300 mM KOH in 2 μl steps using a Mettler Toledo MP220 pH meter. Electrode potential readings for 4 standard buffers were recorded before and after daily batch of measurement. Samples of Compound (1) salts of (1-3 mg) were dissolved in 1 ml of KCl/HCl solution and titrated with vigorous stirring using a small magnetic stirrer. The recorded electrode potentials were converted into pH values using a calibration curve from the 4 standard buffers. Sample and control titration data were processed to produce a Bjerrum plot in the pH range 2-12. The Bjerrum plot calculation and analysis method is described in the review "Physicochemical Profiling (Solubility, Permeability and Charge State)", A. Avdeef (Current Topics in Medicinal Chemistry 2001, p 277-351).

The stoichiometry of the Compound (1) salts was deduced from the starting nH (number of protons at pH=2), (i.e. free base starts with −2 protons, mono-salt with −1 protons (Compound (1)+acid−)), while double salts (Compound (1)2+acid2− or Compound (1)2+2*acid−) start at nH=0.

10A. Free Base Salt Forms (A-i) Free Base Crystal Form FB1

A saturated solution of Compound (1) in 1-butanol was prepared at room temperature. Slow precipitation with approximately 4× volume of di(isopropyl)ether gave crystal form FB1. XRPD analysis of the fresh sample gave the pattern shown in FIG. 1 and the main peaks listed in Table 1 below. After drying in air for three days, a new XRPD pattern was obtained which showed that the crystal form FB1 had converted completely to crystal form FB3.

TABLE 1

Main XRPD peaks for Compound (1) Form FB1

| 2θ/° | d/Å | I/% |
|---|---|---|
| 5.52 | 15.99 | 100 |
| 9.44 | 9.36 | 5 |
| 11.05 | 8.00 | 6 |
| 11.99 | 7.38 | 4 |
| 15.21 | 5.82 | 16 |
| 16.11 | 5.50 | 16 |
| 16.72 | 5.30 | 11 |
| 17.09 | 5.18 | 8 |
| 18.21 | 4.87 | 19 |
| 19.23 | 4.61 | 6 |
| 19.73 | 4.50 | 9 |
| 20.29 | 4.37 | 16 |
| 21.09 | 4.21 | 5 |
| 26.72 | 3.33 | 3 |

(A-ii) Free Base Crystal Form FB2

A saturated solution of Compound (1) in THF was prepared at room temperature. Slow precipitation with approximately 4× volume of isopropyl acetate gives crystal form FB2. The XRPD pattern of a fresh sample of form FB2 is shown in FIG. 2 and the main peaks in the XRPD pattern are listed in Table 2 below. The sample was dried in air for 3 days after which a new XRPD pattern was obtained: this demonstrated that the crystal form FB2 had changed to crystal form FB3.

TABLE 2

Main XRPD peaks for Compound (1) Crystal form FB2

| 2θ/° | d/Å | I/% |
|---|---|---|
| 5.35 | 16.49 | 100 |
| 6.73 | 13.13 | 2 |
| 10.40 | 8.50 | 3 |
| 10.67 | 8.28 | 4 |
| 14.68 | 6.03 | 13 |
| 17.00 | 5.24 | 11 |
| 18.26 | 4.85 | 8 |
| 18.61 | 4.76 | 10 |
| 18.87 | 4.70 | 8 |
| 19.24 | 4.61 | 7 |
| 19.86 | 4.47 | 18 |
| 20.15 | 4.40 | 16 |
| 21.13 | 4.20 | 9 |
| 21.44 | 4.14 | 7 |
| 26.86 | 3.32 | 3 |

(A4-iii) Free Base Crystal Form FB3

Crystal form FB3 was obtained from forms FB1 and FB2 as described above or by evaporation of a solution of the free base. The XRPD pattern for crystal form FB3 is shown in FIG. 3 and the main peaks are listed in Table 3 below. Crystal form FB3 was found to be stable in air and at 40° C. and 75% RH for at least one month.

TABLE 3

Main XRPD peaks for Compound (1) crystal form FB3

| 2θ/° | d/Å | I/% |
|---|---|---|
| 6.05 | 14.59 | 100 |
| 7.87 | 11.22 | 9 |
| 9.15 | 9.66 | 7 |
| 10.22 | 8.65 | 3 |
| 12.15 | 7.28 | 11 |
| 13.60 | 6.50 | 14 |
| 15.77 | 5.62 | 17 |

TABLE 3-continued

Main XRPD peaks for Compound (1) crystal form FB3

| 2θ/° | d/Å | I/% |
|---|---|---|
| 16.62 | 5.33 | 4 |
| 17.16 | 5.16 | 7 |
| 17.82 | 4.97 | 11 |
| 18.89 | 4.69 | 22 |
| 19.64 | 4.52 | 12 |
| 20.20 | 4.39 | 21 |
| 20.93 | 4.24 | 10 |
| 22.19 | 4.00 | 5 |
| 23.33 | 3.81 | 6 |
| 24.53 | 3.63 | 5 |

(A-iv) Free Base Crystal Form FB4

Crystal form FB4 was observed in precipitation experiments of ethanol solutions of Compound (1). Single crystal X-ray analysis showed that that the crystal form is a dihydrate. A saturated solution of Compound (1) in ethanol was prepared at room temperature. Slow precipitation with approximately 4× volume of isopropyl ether gave crystal form FB4 which was found to be stable in air. The XRPD pattern of form FB4 is shown in FIG. 4 and the main peaks are listed in Table 4 below. The crystal packing diagram and atom coordinates are in FIG. 5 and Table 5.

TABLE 4

Main XRPD peaks for Compound (1) Crystal form FB4

| 2θ/° | d/Å | I/% |
|---|---|---|
| 6.29 | 14.04 | 100 |
| 8.91 | 9.92 | 12 |
| 9.96 | 8.87 | 14 |
| 12.62 | 7.01 | 4 |
| 14.11 | 6.27 | 16 |
| 16.11 | 5.50 | 14 |
| 17.11 | 5.18 | 10 |
| 17.40 | 5.09 | 5 |
| 17.88 | 4.96 | 8 |
| 18.48 | 4.80 | 17 |
| 19.33 | 4.59 | 4 |
| 19.91 | 4.46 | 10 |
| 20.35 | 4.36 | 8 |
| 21.57 | 4.12 | 23 |
| 22.46 | 3.95 | 13 |
| 23.59 | 3.77 | 14 |
| 24.88 | 3.58 | 17 |
| 27.25 | 3.27 | 9 |

TABLE 5

Unit cell parameters and coordinates in cif format for crystal structure of Compound (1) Crystal form FB4 space group: P42/n
unit cell at 293 K with a, b & c having 5% s.u.:
a = b = 28.2
c = 6.0
alpha = beta = gamma = 90
Coordinates in cif format:
loop_
    _atom_site_label
    _atom_site_type_symbol
    _atom_site_fract_x
    _atom_site_fract_y
    _atom_site_fract_z
    _atom_site_U_iso_or_equiv
    _atom_site_adp_type
    _atom_site_occupancy
    _atom_site_symmetry_multiplicity
    _atom_site_calc_flag
    _atom_site_refinement_flags
    _atom_site_disorder_assembly
    _atom_site_disorder_group

| label | type | fract_x | fract_y | fract_z | U | adp | occ | mult | calc | flag | | | |
|---|---|---|---|---|---|---|---|---|---|---|---|---|---|
| C1 | C | 0.60531(14) | 0.59657(13) | 0.3978(7) | 0.0816(11) | Uani | 1 | 1 | d | . | . | . | |
| H1A | H | 0.6390 | 0.5959 | 0.3641 | 0.098 | Uiso | 1 | 1 | calc | . | . | . | |
| H1B | H | 0.6000 | 0.6175 | 0.5237 | 0.098 | Uiso | 1 | 1 | calc | . | . | . | |
| N2 | N | 0.58709(11) | 0.54841(11) | 0.4433(6) | 0.0845(10) | Uani | 1 | 1 | d | . | . | . | |
| C3 | C | 0.55080(14) | 0.53422(15) | 0.2788(8) | 0.0924(13) | Uani | 1 | 1 | d | . | . | . | |
| H3A | H | 0.5207 | 0.5275 | 0.3505 | 0.111 | Uiso | 1 | 1 | calc | . | . | . | |
| H3B | H | 0.5608 | 0.5065 | 0.1955 | 0.111 | Uiso | 1 | 1 | calc | . | . | . | |
| C4 | C | 0.54727(14) | 0.57663(14) | 0.1322(7) | 0.0838(11) | Uani | 1 | 1 | d | . | . | . | |
| C5 | C | 0.57724(14) | 0.61201(14) | 0.2011(7) | 0.0801(11) | Uani | 1 | 1 | d | . | . | . | |
| C6 | C | 0.51860(15) | 0.58333(16) | -0.0535(8) | 0.0921(13) | Uani | 1 | 1 | d | . | . | . | |
| H6 | H | 0.4985 | 0.5592 | -0.1007 | 0.111 | Uiso | 1 | 1 | calc | . | . | . | |
| C7 | C | 0.52000(15) | 0.62568(18) | -0.1672(8) | 0.0926(13) | Uani | 1 | 1 | d | . | . | . | |
| C8 | C | 0.54951(17) | 0.66174(16) | -0.0895(8) | 0.0966(13) | Uani | 1 | 1 | d | . | . | . | |
| H8 | H | 0.5497 | 0.6908 | -0.1625 | 0.116 | Uiso | 1 | 1 | calc | . | . | . | |
| C9 | C | 0.57843(16) | 0.65525(16) | 0.0930(8) | 0.0935(13) | Uani | 1 | 1 | d | . | . | . | |
| H9 | H | 0.5983 | 0.6794 | 0.1423 | 0.112 | Uiso | 1 | 1 | calc | . | . | . | |
| C10 | C | 0.49149(17) | 0.63467(19) | -0.3746(8) | 0.1025(14) | Uani | 1 | 1 | d | . | . | . | |
| H10A | H | 0.5120 | 0.6491 | -0.4853 | 0.123 | Uiso | 1 | 1 | calc | . | . | . | |
| H10B | H | 0.4808 | 0.6045 | -0.4336 | 0.123 | Uiso | 1 | 1 | calc | . | . | . | |
| N11 | N | 0.44995(12) | 0.66545(12) | -0.3408(6) | 0.0847(10) | Uani | 1 | 1 | d | . | . | . | |
| C12 | C | 0.41355(16) | 0.64016(16) | -0.2169(7) | 0.0928(12) | Uani | 1 | 1 | d | . | . | . | |
| H12A | H | 0.4257 | 0.6319 | -0.0708 | 0.111 | Uiso | 1 | 1 | calc | . | . | . | |
| H12B | H | 0.4056 | 0.6110 | -0.2941 | 0.111 | Uiso | 1 | 1 | calc | . | . | . | |
| C13 | C | 0.36951(16) | 0.67000(18) | -0.1912(8) | 0.1005(14) | Uani | 1 | 1 | d | . | . | . | |
| H13A | H | 0.3458 | 0.6524 | -0.1081 | 0.121 | Uiso | 1 | 1 | calc | . | . | . | |
| H13B | H | 0.3771 | 0.6985 | -0.1080 | 0.121 | Uiso | 1 | 1 | calc | . | . | . | |

TABLE 5-continued

Unit cell parameters and coordinates in cif format for crystal structure of Compound (1) Crystal form FB4

| | | | | | | | | | | | | |
|---|---|---|---|---|---|---|---|---|---|---|---|---|
| N14 | N | 0.35044(13) | 0.68296(14) | −0.4066(6) | 0.0961(11) | Uani | 1 | 1 | d | . | . | . |
| C15 | C | 0.38701(19) | 0.70846(17) | −0.5299(7) | 0.1001(14) | Uani | 1 | 1 | d | . | . | . |
| H15A | H | 0.3953 | 0.7373 | −0.4509 | 0.120 | Uiso | 1 | 1 | calc | . | . | . |
| H15B | H | 0.3749 | 0.7173 | −0.6753 | 0.120 | Uiso | 1 | 1 | calc | . | . | . |
| C16 | C | 0.43006(17) | 0.67828(18) | −0.5565(7) | 0.0987(14) | Uani | 1 | 1 | d | . | . | . |
| H16A | H | 0.4218 | 0.6497 | −0.6376 | 0.118 | Uiso | 1 | 1 | calc | . | . | . |
| H16B | H | 0.4537 | 0.6954 | −0.6425 | 0.118 | Uiso | 1 | 1 | calc | . | . | . |
| C17 | C | 0.3076(2) | 0.7126(2) | −0.3808(11) | 0.137(2) | Uani | 1 | 1 | d | . | . | . |
| H17A | H | 0.2836 | 0.6950 | −0.3029 | 0.206 | Uiso | 1 | 1 | calc | . | . | . |
| H17B | H | 0.2959 | 0.7215 | −0.5250 | 0.206 | Uiso | 1 | 1 | calc | . | . | . |
| H17C | H | 0.3154 | 0.7407 | −0.2978 | 0.206 | Uiso | 1 | 1 | calc | . | . | . |
| C18 | C | 0.59855(15) | 0.51789(15) | 0.6047(8) | 0.0896(12) | Uani | 1 | 1 | d | . | . | . |
| O19 | O | 0.57503(11) | 0.47935(11) | 0.6072(6) | 0.1109(11) | Uani | 1 | 1 | d | . | . | . |
| C20 | C | 0.63596(13) | 0.52545(13) | 0.7750(7) | 0.0818(11) | Uani | 1 | 1 | d | . | . | . |
| C21 | C | 0.64335(16) | 0.48917(15) | 0.9312(8) | 0.0920(13) | Uani | 1 | 1 | d | . | . | . |
| C22 | C | 0.67703(18) | 0.49413(16) | 1.0959(8) | 0.0986(14) | Uani | 1 | 1 | d | . | . | . |
| H22 | H | 0.6811 | 0.4701 | 1.2002 | 0.118 | Uiso | 1 | 1 | calc | . | . | . |
| C23 | C | 0.70497(16) | 0.53453(15) | 1.1082(8) | 0.0907(12) | Uani | 1 | 1 | d | . | . | . |
| C24 | C | 0.70021(15) | 0.57066(15) | 0.9542(8) | 0.0877(12) | Uani | 1 | 1 | d | . | B | . |
| C25 | C | 0.66614(15) | 0.56535(14) | 0.7956(8) | 0.0889(12) | Uani | 1 | 1 | d | . | . | . |
| H25 | H | 0.6624 | 0.5898 | 0.6929 | 0.107 | Uiso | 1 | 1 | calc | . | . | . |
| O26 | O | 0.61807(14) | 0.44835(11) | 0.9277(7) | 0.1192(12) | Uani | 1 | 1 | d | . | . | . |
| H26 | H | 0.5962 | 0.4508 | 0.8383 | 0.179 | Uiso | 1 | 1 | calc | R | . | . |
| O27 | O | 0.73840(13) | 0.53982(12) | 1.2687(6) | 0.1135(11) | Uani | 1 | 1 | d | . | . | . |
| H27 | H | 0.7403 | 0.5153 | 1.3418 | 0.170 | Uiso | 1 | 1 | calc | R | . | . |
| C28 | C | 0.73311(18) | 0.61386(17) | 0.9614(10) | 0.1084(16) | Uani | 1 | 1 | d | . | . | . |
| H28 | H | 0.7646 | 0.6017 | 1.0009 | 0.130 | Uiso | 1 | 1 | calc | . | A | 1 |
| C29 | C | 0.7389(2) | 0.6388(2) | 0.7301(12) | 0.107(3) | Uani | 0.775(12) | 1 | d | P | B | 1 |
| H29A | H | 0.7600 | 0.6654 | 0.7448 | 0.160 | Uiso | 0.78 | 1 | calc | P | B | 1 |
| H29B | H | 0.7085 | 0.6497 | 0.6790 | 0.160 | Uiso | 0.78 | 1 | calc | P | B | 1 |
| H29C | H | 0.7518 | 0.6167 | 0.6246 | 0.160 | Uiso | 0.78 | 1 | calc | P | B | 1 |
| C30 | C | 0.7207(3) | 0.6487(3) | 1.1347(14) | 0.120(3) | Uani | 0.775(12) | 1 | d | P | B | 1 |
| H30A | H | 0.7434 | 0.6741 | 1.1332 | 0.180 | Uiso | 0.78 | 1 | calc | P | B | 1 |
| H30B | H | 0.7211 | 0.6336 | 1.2778 | 0.180 | Uiso | 0.78 | 1 | calc | P | B | 1 |
| H30C | H | 0.6896 | 0.6612 | 1.1060 | 0.180 | Uiso | 0.78 | 1 | calc | P | B | 1 |
| C29 | C | 0.6972(10) | 0.6587(7) | 0.927(11) | 0.22(3) | Uani | 0.225(12) | 1 | d | P | B | 2 |
| C30 | C | 0.7740(7) | 0.6111(12) | 0.913(5) | 0.147(13) | Uani | 0.225(12) | 1 | d | P | B | 2 |
| O1W | O | 0.75198(14) | 0.46640(15) | 1.5369(7) | 0.1195(12) | Uani | 1 | 1 | d | D | . | . |
| H1W1 | H | 0.7317(14) | 0.4461(18) | 1.565(11) | 0.16(3) | Uiso | 1 | 1 | d | D | . | . |
| H2W1 | H | 0.7750 | 0.4600 | 1.6200 | 0.220 | Uiso | 1 | 1 | d | D | . | . |
| O2W | O | 0.31342(14) | 0.60501(17) | 0.3540(9) | 0.1423(15) | Uani | 1 | 1 | d | D | . | . |
| H1W2 | H | 0.337(2) | 0.595(3) | 0.285(14) | 0.220 | Uiso | 1 | 1 | d | D | . | . |
| H2W2 | H | 0.324(3) | 0.629(2) | 0.424(13) | 0.220 | Uiso | 1 | 1 | d | D | . | . |

(A-v) Free Base Crystal Form FB5

Form FB5 is an unstable form that was observed only in crystallization experiments involving isopropanol solutions of Compound (1). Form FB5 transforms to FB6 in air. Without wishing to be bound by any theory, it is believed that FB5 is an isopropanol solvate.

Form FB5 was formed by preparing a saturated solution of Compound (1) in isopropanol at room temperature followed by slow precipitation with approximately 4 volumes of isopropyl acetate. The XRPD pattern of a fresh sample is shown in FIG. 6 and the main peaks are listed in Table 6 below. A sample of FB5 was dried in air for 2 days after which XRPD analysis showed conversion to form FB6.

TABLE 6

Main XRPD peaks for Compound (1) FB5

| 2θ/° | d/Å | I/% |
|---|---|---|
| 7.12 | 12.41 | 100 |
| 9.71 | 9.10 | 14 |
| 10.14 | 8.72 | 17 |
| 11.50 | 7.69 | 4 |
| 13.73 | 6.45 | 16 |
| 14.60 | 6.06 | 5 |
| 15.34 | 5.77 | 4 |
| 16.58 | 5.34 | 21 |
| 16.94 | 5.23 | 6 |
| 18.71 | 4.74 | 32 |
| 19.46 | 4.56 | 48 |
| 20.15 | 4.40 | 13 |
| 21.97 | 4.04 | 6 |
| 22.35 | 3.97 | 14 |
| 23.43 | 3.79 | 9 |
| 26.36 | 3.38 | 8 |

(A-vi) Free Base Crystal Form FB6

Form FB6 was observed only as a product of form FB5 ageing. Form FB6 is stable on air. The XRPD pattern of a sample of form FB6 that has been prepared by allowing form FB5 to dry for 2 days in air is shown in FIG. 7. A list of the main peaks is set out in Table 7 below.

TABLE 7

Main XRPD peaks for Compound (1) form FB6

| 2θ/° | d/Å | I/% |
|---|---|---|
| 4.60 | 19.21 | 4 |
| 9.09 | 9.72 | 14 |
| 9.68 | 9.13 | 25 |
| 16.08 | 5.51 | 25 |
| 16.46 | 5.38 | 28 |
| 16.94 | 5.23 | 14 |
| 18.13 | 4.89 | 23 |
| 18.66 | 4.75 | 100 |
| 20.05 | 4.42 | 31 |
| 22.48 | 3.95 | 10 |
| 26.53 | 3.36 | 9 |

10B. Compound (1) Hydrochloride 1:2 salt crystal forms (B-i) Compound (1) hydrochloride—Form FH1

EtOAc/HCl was added to 2,4-dihydroxy-5-isopropyl-phenyl)-[5-(4-methyl-piperazin-1-ylmethyl)-1,3-dihydro-isoindol-2-yl]-methanone and then MeOH until a solution was formed. The solvent was evaporated and re-evaporated with toluene and then with MeOH until dry, to yield 2,4-dihydroxy-5-isopropyl-phenyl)-[5-(4-methyl-piperazin-1-ylmethyl)-1,3-dihydro-isoindol-2-yl]-methanone as the di-HCl salt. This form is very hygroscopic and dissolves in air moisture. The XRPD pattern is shown in FIG. 8 and the main peaks are set out in Table 8 below.

TABLE 8

Main XRPD peaks for Compound (1) hydrochloride form-FH1

| 2θ/° | d/Å | I/% |
|---|---|---|
| 5.59 | 15.79 | 16 |
| 7.34 | 12.04 | 100 |
| 7.99 | 11.05 | 19 |
| 10.33 | 8.56 | 11 |
| 11.70 | 7.56 | 3 |
| 13.95 | 6.34 | 4 |
| 14.32 | 6.18 | 10 |
| 14.72 | 6.01 | 4 |
| 15.29 | 5.79 | 11 |
| 16.37 | 5.41 | 4 |
| 16.82 | 5.27 | 8 |
| 18.59 | 4.77 | 10 |
| 19.99 | 4.44 | 3 |
| 20.40 | 4.35 | 4 |
| 20.82 | 4.26 | 2 |
| 21.26 | 4.18 | 4 |
| 22.57 | 3.94 | 3 |
| 23.01 | 3.86 | 1 |
| 24.60 | 3.62 | 6 |
| 25.32 | 3.51 | 20 |
| 25.82 | 3.45 | 6 |
| 27.10 | 3.29 | 4 |
| 28.27 | 3.15 | 7 |
| 28.78 | 3.10 | 7 |

(B-ii) Compound (1) Hydrochloride—Form FH2

Form FH2 was observed in precipitation experiments with DMSO or DMF solutions of form FH1. This form transforms on air into form FH3. A saturated solution of form FH1 (B-i) in DMF was prepared at room temperature. Slow precipitation with approximately 4 volumes of acetone gave form FH2. The XRPD pattern of a fresh sample of form FH2 is shown in FIG. 9 and the main peaks are listed in Table 9 below. A sample of form FH2 was dried in air for 2 days after which XRPD analysis showed that conversion to form FH3 had occurred.

TABLE 9

Main XRPD peaks for Compound (1) Hydrochloride Form FH2

| 2θ/° | d/Å | I/% |
|---|---|---|
| 3.40 | 25.99 | 100 |
| 6.04 | 14.62 | 3 |
| 6.81 | 12.97 | 81 |
| 9.03 | 9.78 | 29 |
| 11.84 | 7.47 | 20 |
| 13.01 | 6.80 | 3 |
| 13.69 | 6.46 | 4 |
| 15.70 | 5.64 | 10 |
| 16.10 | 5.50 | 31 |
| 16.59 | 5.34 | 8 |
| 17.17 | 5.16 | 4 |
| 18.13 | 4.89 | 14 |
| 20.84 | 4.26 | 23 |
| 21.39 | 4.15 | 6 |
| 21.87 | 4.06 | 8 |
| 23.19 | 3.83 | 13 |
| 23.94 | 3.71 | 14 |
| 24.78 | 3.59 | 6 |
| 25.65 | 3.47 | 18 |
| 25.97 | 3.43 | 6 |
| 26.94 | 3.31 | 5 |
| 27.59 | 3.23 | 3 |
| 28.06 | 3.18 | 5 |
| 29.53 | 3.02 | 6 |

(B-iii) Compound (1) Hydrochloride—Form FH3

Form FH3 was observed in precipitation experiments with ethanol or isopropanol solutions of form FH1 as well as in the degradation of form FH2. Form FH3 is stable in air and at 40° C. and 75% RH for at least one month. The preparation of form FH3 is described in Example 3 above. The XRPD pattern for form FH3 is shown in FIG. 10 and the main peaks are listed in Table 10.

TABLE 10

Main XRPD peaks for Compound (1) Hydrochloride Form FH3

| 2θ/° | d/Å | I/% |
|---|---|---|
| 5.83 | 15.15 | 5 |
| 9.35 | 9.45 | 100 |
| 10.40 | 8.50 | 89 |
| 10.78 | 8.20 | 19 |
| 11.35 | 7.79 | 11 |
| 11.71 | 7.55 | 16 |
| 12.51 | 7.07 | 48 |
| 13.35 | 6.63 | 10 |
| 13.81 | 6.41 | 17 |
| 14.10 | 6.27 | 5 |
| 14.78 | 5.99 | 42 |
| 17.18 | 5.16 | 8 |
| 17.65 | 5.02 | 9 |
| 18.74 | 4.73 | 31 |
| 19.09 | 4.65 | 35 |
| 19.46 | 4.56 | 13 |
| 20.11 | 4.41 | 8 |
| 21.18 | 4.19 | 18 |
| 21.68 | 4.10 | 28 |
| 22.32 | 3.98 | 76 |
| 23.07 | 3.85 | 28 |
| 23.71 | 3.75 | 16 |
| 24.86 | 3.58 | 96 |
| 25.14 | 3.54 | 45 |
| 26.49 | 3.36 | 5 |
| 27.03 | 3.30 | 8 |
| 28.09 | 3.17 | 14 |
| 28.70 | 3.11 | 16 |
| 29.02 | 3.07 | 29 |
| 29.52 | 3.02 | 17 |

(B-iv) Compound (1) Hydrochloride—Form FH4

Form FH4 was observed only in one precipitation experiment (DMF/dioxane). This form is unstable and disintegrates in air. A saturated solution of form FH1 in DMF was prepared at room temperature. Slow precipitation with approximately 4 volumes of 1,4-dioxane gave form FH4. The XRPD pattern of a fresh sample of FH4 is shown in FIG. 11 and the main peaks are listed in Table 11 below. The sample disintegrated in air.

TABLE 11

Main XRPD peaks for Compound (1) hydrochloride-Form FH4

| 2θ/° | d/Å | I/% |
| --- | --- | --- |
| 7.04 | 12.55 | 31 |
| 9.89 | 8.93 | 10 |
| 11.62 | 7.61 | 100 |
| 12.30 | 7.19 | 10 |
| 13.27 | 6.67 | 8 |
| 14.14 | 6.26 | 14 |
| 15.54 | 5.70 | 57 |
| 16.06 | 5.51 | 17 |
| 16.68 | 5.31 | 34 |
| 17.99 | 4.93 | 13 |
| 18.54 | 4.78 | 26 |
| 19.24 | 4.61 | 19 |
| 20.73 | 4.28 | 43 |
| 22.26 | 3.99 | 28 |
| 22.94 | 3.87 | 27 |
| 23.36 | 3.81 | 13 |
| 23.77 | 3.74 | 35 |
| 24.63 | 3.61 | 12 |
| 25.07 | 3.55 | 36 |
| 25.72 | 3.46 | 8 |
| 26.91 | 3.31 | 15 |
| 27.63 | 3.23 | 11 |

(B-v) Compound (1) Hydrochloride—Form FH5

Form Fh5 was observed only in one precipitation experiment (methanol/acetone). This form is unstable and dissolves in moist air. A saturated solution of Form FH1 in methanol was prepared at room temperature. Slow precipitation with approximately 4 volumes of acetone gave form FH5. The XRPD pattern of a fresh sample of FH5 is shown in FIG. 12 and the main peaks are listed in Table 12 below. The sample disintegrates in air.

TABLE 12

Main XRPD peaks for Compound (1) hydrochloride-Form FH5

| 2θ/° | d/Å | I/% |
| --- | --- | --- |
| 2.32 | 38.00 | 100 |
| 6.15 | 14.35 | 18 |
| 11.79 | 7.50 | 6 |
| 15.79 | 5.61 | 5 |
| 20.81 | 4.27 | 8 |
| 22.76 | 3.90 | 3 |
| 23.76 | 3.74 | 5 |

10C. Compound (1) L-Lactate 1:1 Salt Crystal Forms (C-i) Compound (1) L-Lactate—Form FL1

The L-Lactate salt form FL was prepared as described in Example 2 above.

Form FL is stable in air and at 40° C. and 75% RH for at least one month. The XRPD pattern for form FL is shown in FIG. 13 and the main peaks are listed in Table 13.

TABLE 13

Main XRPD peaks for Compound (1) Lactate-Form FL1

| 2θ/° | d/Å | I/% |
| --- | --- | --- |
| 6.18 | 14.30 | 15 |
| 6.53 | 13.52 | 50 |
| 8.39 | 10.54 | 19 |
| 11.08 | 7.98 | 7 |
| 13.10 | 6.75 | 85 |
| 14.13 | 6.26 | 33 |
| 14.40 | 6.15 | 23 |
| 15.21 | 5.82 | 4 |
| 16.21 | 5.46 | 6 |
| 16.81 | 5.27 | 100 |
| 17.22 | 5.15 | 45 |
| 18.65 | 4.75 | 23 |
| 19.52 | 4.54 | 33 |
| 19.82 | 4.48 | 34 |
| 20.49 | 4.33 | 7 |
| 20.76 | 4.27 | 13 |
| 21.13 | 4.20 | 17 |
| 22.02 | 4.03 | 12 |
| 22.33 | 3.98 | 44 |
| 22.84 | 3.89 | 40 |
| 23.09 | 3.85 | 25 |
| 23.94 | 3.71 | 14 |
| 25.19 | 3.53 | 7 |
| 26.41 | 3.37 | 14 |
| 26.95 | 3.31 | 5 |
| 27.81 | 3.21 | 14 |

(C-ii) Compound (1) L-Lactate—Form FL2

Form FL2 was observed in precipitation experiments of methanol solutions of form FL1. Single crystal X-ray analysis showed that form FL2 is hydrated. It is nominally a trihydrate because there are 3 crystal water positions in the asymmetric unit, but they are not 100% occupied at room temperature and laboratory humidity. A saturated solution of form FL1 in methanol:water 9:1 was prepared at room temperature. Slow precipitation with approximately 4 volumes of acetone gave form FL2 which is stable in air. The XRPD pattern for form FL2 is shown in FIG. 14 and the main peaks are listed in Table 14 below. A crystal packing diagram is shown in FIG. 15 and the atom coordinates are listed in Table 15 below.

TABLE 14

Main XRPD peaks for Compound (1) Lactate salt-form FL2

| 2θ/° | d/Å | I/% |
| --- | --- | --- |
| 8.03 | 11.00 | 29 |
| 10.71 | 8.26 | 53 |
| 11.98 | 7.38 | 90 |
| 13.13 | 6.74 | 49 |
| 15.39 | 5.75 | 29 |
| 16.09 | 5.50 | 32 |
| 16.61 | 5.33 | 42 |
| 17.26 | 5.13 | 17 |
| 18.17 | 4.88 | 20 |
| 18.82 | 4.71 | 56 |
| 20.40 | 4.35 | 40 |
| 21.01 | 4.22 | 49 |
| 21.53 | 4.12 | 27 |
| 22.34 | 3.98 | 100 |
| 22.56 | 3.94 | 73 |
| 23.71 | 3.75 | 82 |
| 24.30 | 3.66 | 8 |
| 24.65 | 3.61 | 12 |
| 26.56 | 3.35 | 13 |
| 27.70 | 3.22 | 21 |
| 28.29 | 3.15 | 16 |

TABLE 15

Unit cell parameters and coordinates in cif format for crystal structure of Compound (1) Lactate salt—form FL2 space group: P21
unit cell at 293 K with a, b, c & β having 5% s.u.:
a = 5.8
b = 16.6
c = 14.9
beta = 98
alpha = gamma = 90
Coordinates in cif format:
loop_
  _atom_site_label
  _atom_site_type_symbol
  _atom_site_fract_x
  _atom_site_fract_y
  _atom_site_fract_z
  _atom_site_U_iso_or_equiv
  _atom_site_adp_type
  _atom_site_occupancy
  _atom_site_symmetry_multiplicity
  _atom_site_calc_flag
  _atom_site_refinement_flags
  _atom_site_disorder_assembly
  _atom_site_disorder_group

| label | type | fract_x | fract_y | fract_z | U_iso | adp | occ | mult | calc | refine | dis_asm | dis_grp |
|---|---|---|---|---|---|---|---|---|---|---|---|---|
| C1 | C | −0.643(2) | 1.1037(6) | 0.6763(7) | 0.097(3) | Uani | 1 | 1 | d | . | . | . |
| H1A | H | −0.6995 | 1.0577 | 0.6395 | 0.117 | Uiso | 1 | 1 | calc | . | . | . |
| H1B | H | −0.5231 | 1.1308 | 0.6484 | 0.117 | Uiso | 1 | 1 | calc | . | . | . |
| N2 | N | −0.5563(16) | 1.0791(5) | 0.7694(6) | 0.096(2) | Uani | 1 | 1 | d | . | . | . |
| C3 | C | −0.692(3) | 1.1148(8) | 0.8352(8) | 0.124(4) | Uani | 1 | 1 | d | . | . | . |
| H3A | H | −0.7713 | 1.0734 | 0.8651 | 0.148 | Uiso | 1 | 1 | calc | . | . | . |
| H3B | H | −0.5925 | 1.1454 | 0.8805 | 0.148 | Uiso | 1 | 1 | calc | . | . | . |
| C4 | C | −0.8553(19) | 1.1667(7) | 0.7825(7) | 0.094(3) | Uani | 1 | 1 | d | . | . | . |
| C5 | C | −0.8393(19) | 1.1609(6) | 0.6900(7) | 0.092(3) | Uani | 1 | 1 | d | . | . | . |
| C6 | C | −1.036(3) | 1.2141(8) | 0.8083(8) | 0.110(3) | Uani | 1 | 1 | d | . | . | . |
| H6 | H | −1.0636 | 1.2139 | 0.8682 | 0.132 | Uiso | 1 | 1 | calc | . | . | . |
| C7 | C | −1.172(2) | 1.2611(8) | 0.7456(8) | 0.105(3) | Uani | 1 | 1 | d | . | . | . |
| C8 | C | −1.145(2) | 1.2560(8) | 0.6564(9) | 0.111(3) | Uani | 1 | 1 | d | . | . | . |
| H8 | H | −1.2387 | 1.2867 | 0.6138 | 0.133 | Uiso | 1 | 1 | calc | . | . | . |
| C9 | C | −0.979(2) | 1.2053(9) | 0.6287(7) | 0.109(3) | Uani | 1 | 1 | d | . | . | . |
| H9 | H | −0.9640 | 1.2017 | 0.5677 | 0.130 | Uiso | 1 | 1 | calc | . | . | . |
| C10 | C | −1.3561(18) | 1.3173(8) | 0.7739(9) | 0.106(3) | Uani | 1 | 1 | d | . | . | . |
| H10A | H | −1.4455 | 1.3402 | 0.7202 | 0.127 | Uiso | 1 | 1 | calc | . | . | . |
| H10B | H | −1.4617 | 1.2864 | 0.8055 | 0.127 | Uiso | 1 | 1 | calc | . | . | . |
| N11 | N | −1.2550(14) | 1.3836(6) | 0.8332(6) | 0.096(2) | Uani | 1 | 1 | d | . | . | . |
| C12 | C | −1.1136(17) | 1.4353(6) | 0.7839(7) | 0.091(3) | Uani | 1 | 1 | d | . | . | . |
| H12A | H | −1.2098 | 1.4591 | 0.7324 | 0.109 | Uiso | 1 | 1 | calc | . | . | . |
| H12B | H | −0.9935 | 1.4035 | 0.7615 | 0.109 | Uiso | 1 | 1 | calc | . | . | . |
| C13 | C | −1.0015(17) | 1.5021(7) | 0.8462(8) | 0.100(3) | Uani | 1 | 1 | d | . | . | . |
| H13A | H | −0.8991 | 1.4783 | 0.8961 | 0.121 | Uiso | 1 | 1 | calc | . | . | . |
| H13B | H | −0.9092 | 1.5368 | 0.8128 | 0.121 | Uiso | 1 | 1 | calc | . | . | . |
| N14 | N | −1.1853(15) | 1.5509(5) | 0.8822(6) | 0.094(2) | Uani | 1 | 1 | d | . | . | . |
| H14 | H | −1.2741 | 1.5755 | 0.8352 | 0.113 | Uiso | 1 | 1 | calc | . | . | . |
| C15 | C | −1.3350(18) | 1.4966(7) | 0.9279(7) | 0.095(3) | Uani | 1 | 1 | d | . | . | . |
| H15A | H | −1.4599 | 1.5276 | 0.9479 | 0.114 | Uiso | 1 | 1 | calc | . | . | . |
| H15B | H | −1.2441 | 1.4730 | 0.9808 | 0.114 | Uiso | 1 | 1 | calc | . | . | . |
| C16 | C | −1.4358(17) | 1.4308(7) | 0.8658(8) | 0.098(3) | Uani | 1 | 1 | d | . | . | . |
| H16A | H | −1.5310 | 1.3959 | 0.8977 | 0.117 | Uiso | 1 | 1 | calc | . | . | . |
| H16B | H | −1.5346 | 1.4542 | 0.8148 | 0.117 | Uiso | 1 | 1 | calc | . | . | . |
| C17 | C | −1.068(2) | 1.6140(9) | 0.9439(9) | 0.119(4) | Uani | 1 | 1 | d | . | . | . |
| H17A | H | −1.1835 | 1.6447 | 0.9694 | 0.178 | Uiso | 1 | 1 | calc | . | . | . |
| H17B | H | −0.9807 | 1.6492 | 0.9103 | 0.178 | Uiso | 1 | 1 | calc | . | . | . |
| H17C | H | −0.9658 | 1.5886 | 0.9916 | 0.178 | Uiso | 1 | 1 | calc | . | . | . |
| C18 | C | −0.382(2) | 1.0287(9) | 0.7999(8) | 0.113(4) | Uani | 1 | 1 | d | . | . | . |
| O19 | O | −0.345(2) | 1.0216(8) | 0.8837(6) | 0.156(4) | Uani | 1 | 1 | d | . | . | . |
| C20 | C | −0.228(2) | 0.9847(6) | 0.7418(7) | 0.096(3) | Uani | 1 | 1 | d | . | . | . |
| C21 | C | −0.069(3) | 0.9286(9) | 0.7863(9) | 0.119(4) | Uani | 1 | 1 | d | . | . | . |
| C22 | C | 0.064(2) | 0.8867(9) | 0.7367(9) | 0.114(4) | Uani | 1 | 1 | d | . | . | . |
| H22 | H | 0.1812 | 0.8547 | 0.7669 | 0.137 | Uiso | 1 | 1 | calc | . | . | . |
| C23 | C | 0.038(2) | 0.8879(7) | 0.6447(8) | 0.097(3) | Uani | 1 | 1 | d | . | . | . |
| C24 | C | −0.1201(18) | 0.9425(7) | 0.5972(8) | 0.096(3) | Uani | 1 | 1 | d | . | B | . |
| C25 | C | −0.253(2) | 0.9882(7) | 0.6463(8) | 0.100(3) | Uani | 1 | 1 | d | . | . | . |
| H25 | H | −0.3632 | 1.0228 | 0.6160 | 0.120 | Uiso | 1 | 1 | calc | . | . | . |
| O26 | O | −0.036(2) | 0.9229(9) | 0.8775(6) | 0.169(5) | Uani | 1 | 1 | d | . | . | . |
| H26 | H | −0.1427 | 0.9456 | 0.8980 | 0.253 | Uiso | 1 | 1 | calc | R | . | . |
| O27 | O | 0.1658(15) | 0.8404(5) | 0.5948(6) | 0.118(3) | Uani | 1 | 1 | d | . | . | . |
| H27 | H | 0.2091 | 0.7999 | 0.6238 | 0.176 | Uiso | 1 | 1 | calc | R | . | . |
| C28 | C | −0.141(4) | 0.9478(11) | 0.4948(10) | 0.138(6) | Uani | 1 | 1 | d | . | A | . |
| H28 | H | −0.0894 | 0.8953 | 0.4750 | 0.166 | Uiso | 1 | 1 | calc | . | A | 1 |
| C29 | C | −0.029(11) | 1.004(4) | 0.449(3) | 0.24(3) | Uani | 0.58(6) | 1 | d | P | B | 1 |

TABLE 15-continued

Unit cell parameters and coordinates in cif format for crystal structure of Compound (1) Lactate salt—form FL2

| | | | | | | | | | | | | | |
|---|---|---|---|---|---|---|---|---|---|---|---|---|---|
| H29A | H | −0.0741 | 0.9976 | 0.3847 | 0.363 | Uiso | 0.58 | 1 | calc | P | B | 1 |
| H29B | H | 0.1361 | 0.9972 | 0.4628 | 0.363 | Uiso | 0.58 | 1 | calc | P | B | 1 |
| H29C | H | −0.0703 | 1.0575 | 0.4662 | 0.363 | Uiso | 0.58 | 1 | calc | P | B | 1 |
| C30 | C | −0.417(7) | 0.950(3) | 0.4621(19) | 0.159(19) | Uani | 0.58(6) | 1 | d | P | B | 1 |
| H30A | H | −0.4911 | 0.9083 | 0.4918 | 0.239 | Uiso | 0.58 | 1 | calc | P | B | 1 |
| H30B | H | −0.4462 | 0.9424 | 0.3978 | 0.239 | Uiso | 0.58 | 1 | calc | P | B | 1 |
| H30C | H | −0.4773 | 1.0016 | 0.4772 | 0.239 | Uiso | 0.58 | 1 | calc | P | B | 1 |
| C29 | C | −0.156(11) | 1.040(2) | 0.465(2) | 0.14(2) | Uani | 0.42(6) | 1 | d | P | B | 2 |
| H29D | H | −0.0071 | 1.0655 | 0.4814 | 0.215 | Uiso | 0.42 | 1 | calc | P | B | 2 |
| H29E | H | −0.2703 | 1.0675 | 0.4943 | 0.215 | Uiso | 0.42 | 1 | calc | P | B | 2 |
| H29F | H | −0.1983 | 1.0438 | 0.4003 | 0.215 | Uiso | 0.42 | 1 | calc | P | B | 2 |
| C30 | C | −0.295(12) | 0.897(4) | 0.446(2) | 0.150(19) | Uani | 0.42(6) | 1 | d | P | B | 2 |
| H30D | H | −0.3403 | 0.9185 | 0.3870 | 0.224 | Uiso | 0.42 | 1 | calc | P | B | 2 |
| H30E | H | −0.4300 | 0.8910 | 0.4766 | 0.224 | Uiso | 0.42 | 1 | calc | P | B | 2 |
| H30F | H | −0.2234 | 0.8451 | 0.4418 | 0.224 | Uiso | 0.42 | 1 | calc | P | B | 2 |
| O1L | O | −1.5549(12) | 1.6174(6) | 0.7786(6) | 0.124(3) | Uani | 1 | 1 | d | . | . | . |
| O2L | O | −1.7419(12) | 1.7087(6) | 0.6890(7) | 0.125(3) | Uani | 1 | 1 | d | . | . | . |
| C1L | C | −1.5569(17) | 1.6742(7) | 0.7238(8) | 0.098(3) | Uani | 1 | 1 | d | . | . | . |
| C2L | C | −1.3365(17) | 1.6989(8) | 0.6926(9) | 0.108(4) | Uani | 1 | 1 | d | . | . | . |
| H2L | H | −1.3065 | 1.7549 | 0.7117 | 0.129 | Uiso | 1 | 1 | calc | . | . | . |
| C3L | C | −1.355(2) | 1.6971(12) | 0.5917(11) | 0.143(5) | Uani | 1 | 1 | d | . | . | . |
| H3L1 | H | −1.2130 | 1.7162 | 0.5734 | 0.214 | Uiso | 1 | 1 | calc | . | . | . |
| H3L2 | H | −1.4813 | 1.7312 | 0.5662 | 0.214 | Uiso | 1 | 1 | calc | . | . | . |
| H3L3 | H | −1.3842 | 1.6429 | 0.5706 | 0.214 | Uiso | 1 | 1 | calc | . | . | . |
| O3L | O | −1.1538(13) | 1.6538(7) | 0.7316(8) | 0.150(4) | Uani | 1 | 1 | d | . | . | . |
| H3L | H | −1.0243 | 1.6711 | 0.7191 | 0.224 | Uiso | 1 | 1 | d | . | . | . |
| O1W | O | −0.448(6) | 1.237(6) | 1.045(2) | 0.45(5) | Uani | 0.78(6) | 1 | d | P | . | . |
| O2W | O | 0.021(15) | 0.8037(17) | 0.9990(19) | 0.74(7) | Uani | 1 | 1 | d | . | . | . |
| O3W | O | −0.35(3) | 0.773(9) | 0.953(15) | 0.77(8) | Uani | 0.22(6) | 1 | d | P | . | . |

(C-iii) Compound (1) L-Lactate—Form FL3

Form FL3 was observed in precipitation experiments of THF solutions of form FL1. Form FL3 transforms in air into form FL1. A saturated solution of form FL in THF was prepared at room temperature. Slow precipitation with approximately 4 volumes of heptane gave form FL3. The XRPD pattern of a fresh sample of form FL3 is shown in FIG. 16 and the main peaks are listed in Table 16 below. A sample of FL3 was dried in air for 2 days after which XRPD analysis showed that conversion to form FL1 had occurred.

10D. Compound (1) Sulphate 1:1 Salt Crystal Forms (D-i) Compound (1) Sulphate—Form FS1

Form FS1 was observed in crystallization experiments involving acetonitrile as the precipitant. It is unstable on air and transforms to form FS3. A saturated solution of the 1:1 salt of Compound (1) (prepared by dissolving Compound (1) in $H_2SO_4$ and evaporating to dryness) in water was prepared at room temperature. Slow precipitation with approximately 4 volumes of acetonitrile gave form FS1. The XRPD pattern for FS1 is shown in FIG. 17 and the main peaks are listed in Table 17.

TABLE 16

Main XRPD peaks for Compound (1) Lactate salt-form FL3

| 2θ/° | d/Å | I/% |
|---|---|---|
| 5.53 | 15.98 | 100 |
| 8.36 | 10.56 | 5 |
| 11.07 | 7.98 | 41 |
| 13.16 | 6.72 | 12 |
| 13.85 | 6.39 | 8 |
| 16.69 | 5.31 | 39 |
| 17.17 | 5.16 | 21 |
| 18.00 | 4.92 | 49 |
| 18.49 | 4.80 | 11 |
| 19.28 | 4.60 | 14 |
| 19.79 | 4.48 | 5 |
| 20.34 | 4.36 | 7 |
| 21.05 | 4.22 | 21 |
| 21.47 | 4.14 | 7 |
| 21.93 | 4.05 | 4 |
| 22.47 | 3.95 | 16 |
| 22.84 | 3.89 | 23 |
| 24.56 | 3.62 | 4 |
| 26.28 | 3.39 | 6 |
| 27.06 | 3.29 | 3 |
| 27.47 | 3.24 | 3 |
| 29.11 | 3.07 | 6 |

TABLE 17

Main XRPD peaks for Compound (1) Sulphate-Form FS1

| 2θ/° | d/Å | I/% |
|---|---|---|
| 4.79 | 18.45 | 100 |
| 10.02 | 8.82 | 28 |
| 10.68 | 8.28 | 3 |
| 11.28 | 7.84 | 10 |
| 12.89 | 6.86 | 6 |
| 14.38 | 6.15 | 34 |
| 15.27 | 5.80 | 12 |
| 16.91 | 5.24 | 17 |
| 17.64 | 5.02 | 7 |
| 18.29 | 4.85 | 11 |
| 18.86 | 4.70 | 3 |
| 19.28 | 4.60 | 4 |
| 20.12 | 4.41 | 10 |
| 20.82 | 4.26 | 8 |
| 21.21 | 4.19 | 3 |
| 21.76 | 4.08 | 10 |
| 22.32 | 3.98 | 13 |
| 22.89 | 3.88 | 7 |
| 23.83 | 3.73 | 5 |
| 24.22 | 3.67 | 3 |
| 24.42 | 3.64 | 3 |
| 25.13 | 3.54 | 8 |
| 29.04 | 3.07 | 8 |

Compound (1) Sulphate—Form FS2

Form FS2 is unstable on air and transforms to form FS5. If kept at 40° C. and 75% RH, form FS2 transforms to form FS4. Compound (1) was dissolved in 1 mol equivalent of concentrated $H_2SO_4$, precipitated with approximately 4 volumes of acetonitrile and the crystalline mass which formed was filtered. The XRPD pattern for FS2 is shown on FIG. 18 and the main peaks are listed in Table 18.

TABLE 18

Main XRPD peaks for Compound (1) Sulphate-Form FS2

| 2θ/° | d/Å | I/% |
|---|---|---|
| 4.17 | 21.20 | 2 |
| 7.03 | 12.57 | 24 |
| 7.43 | 11.89 | 100 |
| 8.09 | 10.92 | 11 |
| 8.67 | 10.19 | 90 |
| 9.27 | 9.54 | 17 |
| 9.65 | 9.16 | 19 |
| 10.41 | 8.49 | 7 |
| 10.98 | 8.05 | 6 |
| 11.76 | 7.52 | 31 |
| 12.53 | 7.06 | 5 |
| 13.84 | 6.40 | 26 |
| 14.55 | 6.08 | 8 |
| 15.39 | 5.75 | 16 |
| 16.24 | 5.45 | 4 |
| 16.89 | 5.25 | 7 |
| 17.50 | 5.06 | 26 |
| 18.05 | 4.91 | 17 |
| 18.93 | 4.68 | 16 |
| 19.47 | 4.56 | 16 |
| 23.20 | 3.83 | 24 |
| 24.21 | 3.67 | 19 |
| 25.21 | 3.53 | 10 |
| 25.75 | 3.46 | 14 |
| 26.62 | 3.35 | 13 |
| 27.67 | 3.22 | 13 |

Compound (1) Sulphate—Form FS3

Form FS3 is a stable form that was observed as product of form FS1 after ageing in air and the transformation of form FS6 in a warm and humid environment (40° C., 75% RH). The XRPD pattern of a sample of form FS3 that was prepared by allowing form FS1 to dry for 2 days in air is shown in FIG. 19 and the main peaks are listed in Table 19.

TABLE 19

Main XRPD peaks for Compound (1) Sulphate-Form FS3

| 2θ/° | d/Å | I/% |
|---|---|---|
| 4.81 | 18.36 | 17 |
| 5.43 | 16.25 | 100 |
| 10.30 | 8.58 | 48 |
| 11.24 | 7.87 | 24 |
| 12.94 | 6.84 | 5 |
| 13.98 | 6.33 | 7 |
| 14.26 | 6.21 | 26 |
| 14.91 | 5.94 | 33 |
| 15.62 | 5.67 | 12 |
| 16.41 | 5.40 | 56 |
| 17.53 | 5.05 | 26 |
| 18.38 | 4.82 | 28 |
| 18.61 | 4.76 | 40 |
| 19.01 | 4.66 | 22 |
| 19.38 | 4.58 | 10 |
| 19.92 | 4.45 | 30 |
| 20.27 | 4.38 | 13 |
| 20.71 | 4.28 | 6 |
| 21.19 | 4.19 | 9 |
| 21.77 | 4.08 | 31 |
| 22.67 | 3.92 | 20 |
| 23.79 | 3.74 | 19 |
| 24.23 | 3.67 | 27 |
| 25.36 | 3.51 | 21 |
| 27.38 | 3.25 | 6 |
| 28.82 | 3.09 | 9 |

Compound (1) Sulphate—Form FS4

Form FS4 is a stable form that was observed only as a product of the transformation of form FS2 in a warm and humid environment (40° C., 75% RH). An XRPD pattern of a sample of form FS4 that was prepared by incubating form FS2 for several weeks at 40° C. and 75% RH is shown in FIG. 20 and the main peaks are listed in Table 20.

TABLE 20

Main XRPD peaks for Compound (1) Sulphate-Form FS4

| 2θ/° | d/Å | I/% |
|---|---|---|
| 4.64 | 19.03 | 4 |
| 7.16 | 12.34 | 39 |
| 7.48 | 11.80 | 100 |
| 7.97 | 11.08 | 29 |
| 8.42 | 10.49 | 13 |
| 8.82 | 10.02 | 34 |
| 9.09 | 9.73 | 29 |
| 9.37 | 9.43 | 35 |
| 10.45 | 8.46 | 30 |
| 11.77 | 7.51 | 53 |
| 13.25 | 6.68 | 17 |
| 13.54 | 6.54 | 16 |
| 14.36 | 6.16 | 24 |
| 15.03 | 5.89 | 13 |
| 16.21 | 5.46 | 21 |
| 16.99 | 5.22 | 33 |
| 17.28 | 5.13 | 31 |
| 17.59 | 5.04 | 30 |
| 17.96 | 4.93 | 19 |
| 18.90 | 4.69 | 24 |
| 19.43 | 4.57 | 10 |
| 19.83 | 4.47 | 8 |
| 21.36 | 4.16 | 12 |
| 23.13 | 3.84 | 31 |
| 23.68 | 3.75 | 28 |
| 23.96 | 3.71 | 32 |
| 24.77 | 3.59 | 18 |
| 25.64 | 3.47 | 17 |
| 26.19 | 3.40 | 14 |
| 26.73 | 3.33 | 13 |
| 27.70 | 3.28 | 11 |
| 27.76 | 3.21 | 17 |
| 28.64 | 3.11 | 9 |

Compound (1) Sulphate—Form FS5

Form FS53 is a stable form that was observed as a product of the ageing of form FS2 in air and the transformation of form FS4 in a dry environment (20° C., 11% RH). The XRPD pattern of a sample of form FS5 that was prepared by allowing form FS2 to dry for 2 days in air is shown in FIG. 21 and the main peaks are listed in Table 21.

TABLE 21

Main XRPD peaks for Compound (1) Sulphate-Form FS5

| 2θ/° | d/Å | I/% |
|---|---|---|
| 4.70 | 18.80 | 19 |
| 7.11 | 12.42 | 56 |

TABLE 21-continued

Main XRPD peaks for Compound (1) Sulphate-Form FS5

| 2θ/° | d/Å | I/% |
|---|---|---|
| 7.99 | 11.05 | 100 |
| 9.33 | 9.47 | 42 |
| 9.57 | 9.23 | 29 |
| 10.45 | 8.46 | 54 |
| 11.64 | 7.60 | 30 |
| 13.27 | 6.67 | 62 |
| 14.28 | 6.20 | 20 |
| 14.65 | 6.04 | 13 |
| 15.12 | 5.86 | 14 |
| 15.60 | 5.67 | 24 |
| 16.98 | 5.22 | 88 |
| 17.65 | 5.02 | 22 |
| 18.01 | 4.92 | 35 |
| 18.80 | 4.72 | 48 |
| 19.32 | 4.59 | 17 |
| 19.83 | 4.47 | 13 |
| 21.08 | 4.21 | 18 |
| 23.21 | 3.83 | 39 |
| 23.51 | 3.78 | 23 |
| 23.92 | 3.72 | 36 |
| 24.30 | 3.66 | 19 |
| 25.06 | 3.55 | 22 |
| 26.24 | 3.39 | 37 |
| 27.28 | 3.27 | 13 |
| 28.67 | 3.11 | 18 |

Compound (1) Sulphate—Form FS6

Form FS6 was identified in a number of different crystallization experiments during form screening. It is stable in air but, in a warm and humid environment (40° C., 75% RH), it transforms into form FS3.

A saturated solution of the 1:1 sulphate salt of Compound (1) (prepared by dissolving Compound (1) in $H_2SO_4$ and evaporating to dryness) in DMF was prepared at room temperature. Slow precipitation with approximately 4 volumes of toluene gave form FS6. The XRPD pattern for FS6 is shown in FIG. 22 and the main peaks are listed in Table 22.

TABLE 22

Main XRPD peaks for Compound (1) Sulphate-Form FS6

| 2θ/° | d/Å | I/% |
|---|---|---|
| 4.82 | 18.32 | 100 |
| 9.98 | 8.86 | 32 |
| 11.35 | 7.79 | 9 |
| 12.92 | 6.85 | 4 |
| 14.45 | 6.13 | 36 |
| 15.38 | 5.76 | 17 |
| 16.97 | 5.22 | 19 |
| 17.52 | 5.06 | 7 |
| 18.18 | 4.87 | 15 |
| 19.42 | 4.57 | 9 |
| 20.23 | 4.39 | 16 |
| 20.93 | 4.24 | 13 |
| 21.31 | 4.17 | 5 |
| 21.66 | 4.10 | 5 |
| 21.89 | 4.06 | 7 |
| 22.29 | 3.98 | 17 |
| 22.84 | 3.89 | 8 |
| 23.04 | 3.86 | 6 |
| 23.94 | 3.71 | 4 |
| 24.51 | 3.63 | 4 |
| 25.26 | 3.52 | 9 |
| 29.18 | 3.06 | 7 |

Example 11

Determination of Antifungal Activity

The antifungal activity of the compounds of the formula (1) is determined using the following protocol.

The compounds are tested against a panel of fungi including *Candida parapsilosis, Candida tropicalis, Candida albicans*-ATCC 36082 and *Cryptococcus neoformans*. The test organisms are maintained on Sabourahd Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 µg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 µg/ml). Well 1 serves as a sterility control and blank for the spectrophotometric assays. Well 12 serves as a growth control. The microtitre plates are inoculated with 10 µl in each of well 2 to 11 (final inoculum size is 104 organisms/ml). Inoculated plates are incubated for 48 hours at 35° C. The MIC values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The MIC endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourahd Dextrose Agar (SDA) plate, incubating for 1 to 2 days at 35° C. and then checking viability.

Example 12

Methods of Testing for Pain Reducing or Pain Preventing Activity (i) Inflammatory Hyperalgesia Test Mechanical hyperalgesia can be examined in a rat model of inflammatory pain. Paw withdrawal thresholds to an increasing pressure stimulus are measured by the Randal-Sellito technique using an analgesymeter (Ugo Basile, Milan), in naïve animals prior to an intraplantar injection of complete Freund's complete adjuvant (FCA) into the left hind paw. 24 hours later paw withdrawal thresholds are measured again prior to (predose) and then from 10 minutes to 6 hours following drug or vehicle administration. Reversal of hyperalgesia in the ipsilateral paw is calculated according to the formula:

$$\% \text{ reversal} = \frac{\text{postdose threshold} - \text{predose threshold}}{\text{naive threshold} - \text{predose threshold}} \times 100$$

(ii) Neuropathic Hyperalgesia Test

Mechanical hyperalgesia can be examined in a rat model of neuropathic pain induced by partial ligation of the left sciatic nerve. Approximately 14 days following surgery mechanical withdrawal thresholds of both the ligated (ipsilateral) and non-ligated (contralateral) paw are measured prior to (predose) and then from 10 minutes to 6 hours following drug or vehicle administration. Reversal of hyperalgesia at each time point is calculated according to the formula:

$$\% \text{ reversal} = \frac{\text{ipsilateral threshold postdose} - \text{ipsilateral threshold predose}}{\text{contralateral threshold postdose} - \text{ipsilateral threshold predose}} \times 100$$

All experiments are carried out using groups of 6 animals. Stock concentrations of drugs are dissolved in distilled water and subsequent dilutions were made in 0.9% saline for subcutaneous administration in a volume of 4 mlkg-1. All drugs are made up in plastic vials and kept in the dark.

Statistical analysis are carried out on withdrawal threshold readings (g) using ANOVA with repeated measures followed by Tukey's HSD test. Efficacy refers to the maximal reversal of hyperalgesia observed at the doses used.

(iii) Testing the Effects of Compounds of Formula (0) a Rat Model of Bone Cancer Pain Adult female rats are given intra-tibial injections of MRMZ-1 rat mammary gland carcinoma cells (3 µl, 107 cells/ml). The animals typically gradually develop mechanical hyperalgesia, mechanical allodynia (skin sensitivity to non-noxious stimuli) and hind limb sparing, beginning on day 12-14 following cell injection. A compound of formula (0) (e.g. at a dose of 10 and 30 µg/kg s.c.) is administered 3 times a week from the day of cell injection, and the extent of inhibition of hind limb sparing and mechanical allodynia is determined in comparison to vehicle-treated controls.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

What is claimed is:

1. A method for reducing cancer in a mammal, the method comprising administering to the mammal an effective amount of an acid addition salt of a compound of the formula (1):

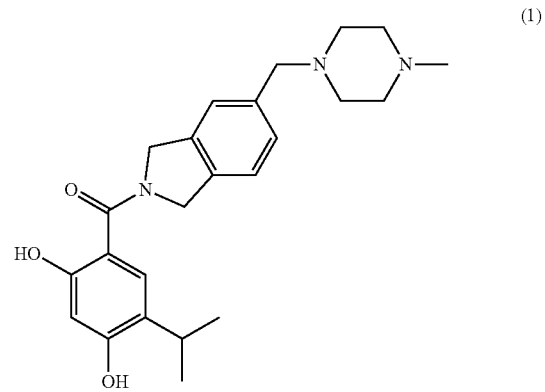 [SMILES: CC(C)c1cc(C(=O)N2Cc3ccc(CN4CCN(C)CC4)cc3C2)c(O)cc1O]

which is a salt formed with lactic acid, wherein said cancer is selected from: carcinoma of the bladder, breast, colon, kidney, epidermis, liver, lung, ovary, pancreas, stomach, thyroid, prostate, gastrointestinal system, skin, a hematopoietic tumor of lymphoid or myeloid lineage, and a tumor of the central or peripheral nervous system.

2. A method of claim 1 wherein the acid addition salt in substantially crystalline form has a crystalline form selected from forms FL1 or FL2.

3. A method for reducing cancer in a mammal, the method comprising administering to the mammal a pharmaceutical composition comprising an effective amount of an acid addition salt of a compound of the formula (1):

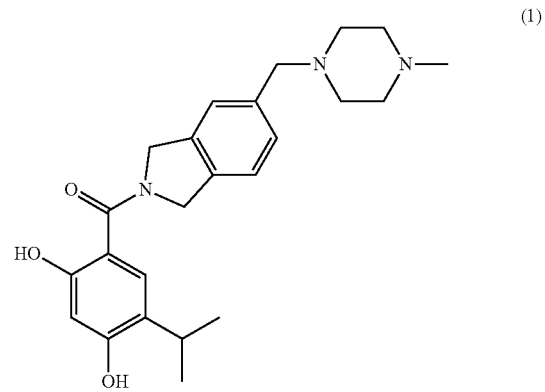 [SMILES: CC(C)c1cc(C(=O)N2Cc3ccc(CN4CCN(C)CC4)cc3C2)c(O)cc1O]

which is a salt formed with lactic acid, and a pharmaceutically acceptable carrier, wherein said cancer is selected from: carcinoma of the bladder, breast, colon, kidney, epidermis, liver, lung, ovary, pancreas, stomach, thyroid, prostate, gastrointestinal system, skin, a hematopoietic tumor of lymphoid or myeloid lineage, and a tumor of the central or peripheral nervous system.

4. A method of claim 3 wherein the acid addition salt in substantially crystalline form has a crystalline form selected from forms FL1 or FL2.

5. A method according to claim 3, wherein said pharmaceutically acceptable carrier is a carrier for intravenous or oral administration.

6. A method according to claim 1 wherein said cancer is selected from: colon adenocarcinoma, colon adenoma, colorectal carcinoma, small cell lung cancer, non-small cell lung carcinoma, exocrine pancreatic carcinoma, gastrointestinal stromal tumors, leukaemia, acute lymphocytic leukaemia, chronic lymphocytic leukaemia, B-cell lymphoma, T-cell lymphoma, Burkett's lymphoma, acute myelogenous leukaemia, chronic myelogenous leukaemia, Imatinib sensitive and refractory chronic myelogenous leukaemia, myeloproliferative disease, melanoma, bortezomib sensitive multiple myeloma, thyroid follicular cancer and glioma.

7. A method according to claim 1 wherein said cancer is selected from: carcinoma of the prostate, gastrointestinal stromal tumors, acute lymphocytic leukaemia, chronic lymphocytic leukaemia, B-cell lymphoma, T-cell lymphoma, Burkett's lymphoma, acute myelogenous leukaemia, chronic myelogenous leukaemia, bortezomib sensitive multiple myeloma, non-small cell lung cancer, thyroid, follicular cancer, melanoma, and ErbB2-positive breast cancer.

8. A method according to claim 3 wherein said cancer is selected from: colon adenocarcinoma, colon adenoma, colorectal carcinoma, small cell lung cancer, non-small cell lung carcinoma, exocrine pancreatic carcinoma, gastrointestinal stromal tumors, leukaemia, acute lymphocytic leukaemia, chronic lymphocytic leukaemia, B-cell lymphoma, T-cell lymphoma, Burkett's lymphoma, acute myelogenous leukaemia, chronic myelogenous leukaemia, Imatinib sensitive and refractory chronic myelogenous leukaemia, myeloproliferative disease, melanoma, bortezomib sensitive multiple myeloma, thyroid follicular cancer and glioma.

9. A method according to claim 1 wherein said cancer is selected from: carcinoma of the prostate, gastrointestinal stromal tumors, acute lymphocytic leukaemia, chronic lymphocytic leukaemia, B-cell lymphoma, T-cell lymphoma, Burkett's lymphoma, acute myelogenous leukaemia, chronic myelogenous leukaemia, bortezomib sensitive multiple myeloma, non-small cell lung cancer, thyroid, follicular cancer, melanoma, and ErbB2-positive breast cancer.

10. A method of claim 1 wherein the lactic acid salt is the L-lactate.

11. A method of claim 3 wherein the lactic acid salt is the L-lactate.

\* \* \* \* \*